(12) United States Patent
Kasai et al.

(10) Patent No.: US 9,505,772 B2
(45) Date of Patent: Nov. 29, 2016

(54) AROMATIC RING COMPOUND

(71) Applicant: TAKEDA PHARMACEUTICAL COMPANY LIMITED, Osaka (JP)

(72) Inventors: Shizuo Kasai, Kanagawa (JP); Hideyuki Igawa, Kanagawa (JP); Masashi Takahashi, Kanagawa (JP); Asato Kina, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/399,396

(22) PCT Filed: May 9, 2013

(86) PCT No.: PCT/JP2013/063030
§ 371 (c)(1),
(2) Date: Nov. 6, 2014

(87) PCT Pub. No.: WO2013/168760
PCT Pub. Date: Nov. 14, 2013

(65) Prior Publication Data
US 2015/0111894 A1    Apr. 23, 2015

Related U.S. Application Data

(60) Provisional application No. 61/645,167, filed on May 10, 2012.

(51) Int. Cl.
*A61K 31/50* (2006.01)
*C07D 491/048* (2006.01)

(52) U.S. Cl.
CPC .................. *C07D 491/048* (2013.01)

(58) Field of Classification Search
None
See application file for complete search history.

(56) References Cited

U.S. PATENT DOCUMENTS

| | | | |
|---|---|---|---|
| 8,101,632 B2 * | 1/2012 | Guzzo | C07D 491/048 514/302 |
| 2004/0077628 A1 | 4/2004 | Ishihara et al. | |
| 2007/0208046 A1 | 9/2007 | Otake et al. | |
| 2008/0255083 A1 | 10/2008 | Stenkamp et al. | |
| 2009/0264426 A1 | 10/2009 | Sakuraba et al. | |
| 2009/0318439 A1 | 12/2009 | Guzzo et al. | |
| 2010/0069362 A1 | 3/2010 | Murata | |

FOREIGN PATENT DOCUMENTS

| | | |
|---|---|---|
| JP | 2010-501518 | 1/2010 |
| JP | 2010-515745 | 5/2010 |
| WO | 01/82925 | 11/2001 |
| WO | 2005/085200 | 9/2005 |
| WO | 2006/118320 | 11/2006 |
| WO | 2007/029847 | 3/2007 |
| WO | 2008/086409 | 7/2008 |
| WO | 2009/076352 | 6/2009 |
| WO | 2010/104830 | 9/2010 |
| WO | 2011/127643 | 10/2011 |
| WO | 2011/130086 | 10/2011 |
| WO | 2013/105676 | 7/2013 |

OTHER PUBLICATIONS

CAPLUS 2010:736395.*
CAPLUS 2012:726033.*
International Search Report issued Jul. 23, 2013 in International (PCT) Application No. PCT/JP2013/063030.
M. D. Surman et al., "5-(Pyridinon-l-yl)indazoles and 5-(furopyridinon-5-yl)indazoles as MCH-1 Antagonists", Bioorganic and Medicinal Chemistry Letters, vol. 20, pp. 7015-7019, 2010.
R. Bergmann et al., "Synthesis and Antihypertensive Activity of 4-(1,2-Dihydro 2-oxo-1-pyridyl)-2H-1-Benzopyrans and Related Compounds, New Potassium Channel Activators", Journal of Medicinal Chemistry, vol. 33, pp. 492-504, 1990.
T. Delaunay et al., "Practical One-Pot Syntheses of Regioisomeric Furan-Fused Pyridinones (and Quinolinones) from Common Precursors", Synthesis, No. 10, pp. 1741-1744, 2010.
CAS Registry No. RN885901-19-9 and RN885901-16-6.

* cited by examiner

*Primary Examiner* — Heidi Reese
(74) *Attorney, Agent, or Firm* — Wenderoth, Lind & Ponack, L.L.P.

(57) ABSTRACT

The present invention provides an aromatic ring compound having a melanin-concentrating hormone receptor antagonistic action and useful as an agent for the prophylaxis or treatment of obesity and the like. The present invention relates to a compound represented by the formula (I)

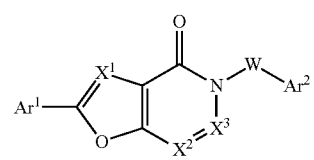

wherein each symbol as defined in the specification, or a salt thereof.

9 Claims, No Drawings

AROMATIC RING COMPOUND

TECHNICAL FIELD

The present invention relates to an aromatic ring compound having melanin-concentrating hormone (hereinafter sometimes abbreviated as MCH) receptor antagonistic action, and useful as an agent for the prophylaxis or treatment of obesity and the like.

BACKGROUND OF THE INVENTION

MCH is a hypothalamus-derived hormone known to have an appetite increasing action. Furthermore, it has been reported that MCH knockout mouse behaves normally but shows a significantly decreased food intake amount and a lighter body weight as compared to normal mouse (Nature, vol. 396, page 670, 1998). Furthermore, MCH receptor-1-deficient mice have been reported to show a lean phenotype (Proc. Natl. Acad. Sci. USA, vol. 99, page 3240, 2002). Therefrom MCH receptor (particularly MCH receptor 1) antagonists are expected to be superior appetite suppressants or anti-obesity agents.

As compounds having a MCH receptor antagonistic action, the following compounds are known.

1) WO2007/029847 (patent document 1) discloses a pyridone derivative represented by the formula:

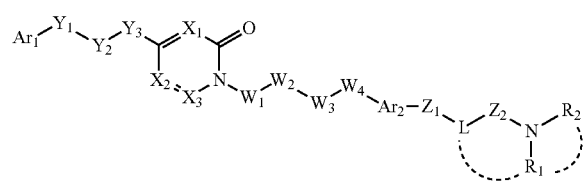
(I)

wherein
$R_1$ and $R_2$ are the same or different and each is a hydrogen atom, a lower alkyl group optionally having substituent(s) or a lower cycloalkyl group optionally having substituent(s), or $R_1$ and $R_2$ form, together with the nitrogen atom bonded thereto, an aliphatic nitrogen-containing heterocycle optionally having substituent(s),
$X_1$, $X_2$ and $X_3$ are the same or different and each is a methine group optionally having substituent(s) or a nitrogen atom, provided that $X_1$, $X_2$ and $X_3$ are not simultaneously nitrogen atoms,
$Y_1$ is a single bond, —O—, —NR—, —S—, —SO— or —SO$_2$—,
$Y_2$ is a lower alkylene group optionally having substituent(s), a lower alkenylene group optionally having substituent(s) or a lower cycloalkylene group optionally having substituent(s),
$Y_3$ is a single bond, —O—, —NR—, —S—, —SO— or —SO$_2$—,
each R is independently a hydrogen atom or a lower alkyl group optionally having substituent(s),
$W_1$, $W_2$, $W_3$ and $W_4$ are the same or different and each is a single bond, a methylene group optionally having substituent(s) or —O—, provided that continuous two or more of $W_1$, $W_2$, $W_3$ and $W_4$ are not simultaneously —O—,
L is a single bond, a methylene group optionally having substituent(s) or an ethylene group optionally having substituent(s), and L optionally forms, together with $Z_2$, $R_1$ and the nitrogen atom bonded to $R_2$, an aliphatic nitrogen-containing heterocycle optionally having substituent(s),
$Z_1$ and $Z_2$ are the same or different, and each is a single bond, a C$_{1-4}$ alkylene group optionally having substituent(s) or —O—,
$Ar_1$ is an aromatic carbocyclic group optionally having substituent(s) or an aromatic heterocyclic group optionally having substituent(s), and
$Ar_2$ is a divalent and bicyclic aromatic carbocyclic group optionally having substituent(s) or a divalent and bicyclic aromatic heterocyclic group optionally having substituent(s), or a pharmaceutically acceptable salt thereof.

2) WO2008/086409 (patent document 2) discloses a compound represented by the following formula:

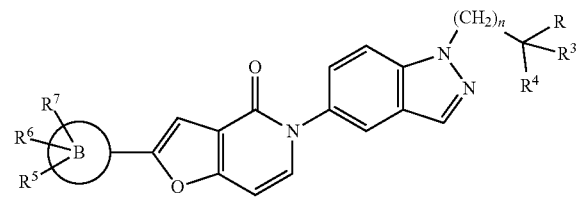

wherein
n is 1 or 2,
R is NR$^1$R$^2$, wherein R$^1$ and R$^2$ are each independently selected from H and optionally substituted alkyl, or R$^1$ and R$^2$ form, together with the adjacent N atom, a 4- to 7-membered optionally substituted heterocycle optionally containing 1 or 2 hetero atoms in addition to the N atom shown,
R$^3$ and R$^4$ are each independently selected from H and alkyl, or
R, R$^3$ and R$^4$ may combine to form an optionally substituted imidazolin-2-yl,
B is aryl or heteroaryl, and
R$^5$, R$^6$ and R$^7$ are each independently selected from H, —OH, —O— alkyl, alkyl, halo, —CF$_3$ and —CN, provided the aforementioned compound is not any of the following

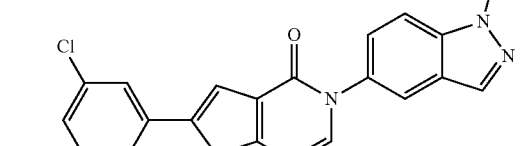

and

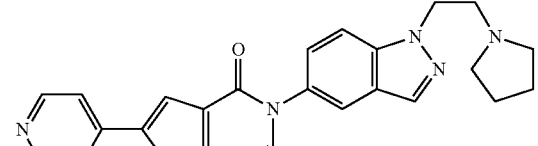

3) Bioorg. Med. Chem. Lett., 20(23), 7015-7019 (2010) (non-patent document 1) discloses a compound represented by the following formula:

wherein R is phenyl, 4-fluorophenyl, 4-chlorophenyl, 2-chlorophenyl, 3-chlorophenyl, 2,4-dichlorophenyl, 4-chloro-2-fluorophenyl, 4-chloro-2-methoxyphenyl, pyridin-2-yl or pyrimidin-2-yl.

4) WO2011/130086 (patent document 3) and WO2011/127643 (patent document 4) disclose a compound represented by the formula:

wherein
$R^1$ and $R^2$ are each independently selected from the group consisting of halogen, hydrogen, —OH, $C_1$-$C_6$ alkyl, —$OC_1$-$C_6$ alkyl, —O-halogen-substituted $C_1$-$C_6$ alkyl and halogen-substituted $C_1$-$C_6$ alkyl;
W is —N— or —CH—;
Q is —O—, —NH— or —C—, or forms heteroaryl together with $R^4$, aromatic ring B and $R^3$;
$R^3$ is halogen, hydrogen, —$OC_1$-$C_6$ alkyl, $C_1$-$C_6$ alkyl, —O-halogen substituted $C_1$-$C_6$ alkyl, halogen-substituted $C_1$-$C_6$ alkyl, cyano, $SO_2C_1$-$C_6$ alkyl or forms a heteroaryl ring together with aromatic ring B, Q and $R^4$;
$R^4$ is hydrogen, oxo, $C_1$-$C_6$ alkyl, halogen-substituted $C_1$-$C_6$ alkyl or forms heteroaryl together with aromatic ring B, $R^3$ and Q, or forms $C_3$-$C_6$ cycloalkyl together with $R^5$;
$R^5$, $R^6$ and $R^7$ are each independently selected from the group consisting of hydrogen, $C_1$-$C_6$ alkyl, halogen-substituted $C_1$-$C_6$ alkyl, $C_3$-$C_6$ cycloalkyl, halogen-substituted $C_3$-$C_6$ cycloalkyl, $C_1$-$C_6$ alkyl $C_3$-$C_6$ cycloalkyl, —OH, $C_1$-$C_6$ alkyl-OH and —$OC_1$-$C_6$ alkyl, or $R^5$ forms oxo group or $C_3$-$C_6$ cycloalkyl together with $R^6$, or $R^5$ forms $C_3$-$C_6$ cycloalkyl together with $R^4$, and at least one of $R^5$, $R^6$ and $R^7$ is not hydrogen, and
n is 1-3,
or a pharmaceutically acceptable salt thereof.

5) WO2010/104830 (patent document 5) discloses a compound represented by the formula or a salt thereof.

6) WO01/82925 (patent document 6) discloses a compound represented by the formula:

wherein
$Ar^1$ is a cyclic group optionally having substituent(s);
X and Y are the same or different and each is a spacer having a main chain of 1 to 6 atoms;
Ar is a fused polycyclic aromatic ring optionally having substituent(s);
$R^1$ and $R^2$ are the same or different and each is a hydrogen atom or a hydrocarbon group optionally having substituent(s), $R^1$ and $R^2$ optionally form, together with the adjacent nitrogen atom, a nitrogen-containing heterocycle optionally having substituent(s), $R^2$ optionally form, together with the adjacent nitrogen atom and Y, a nitrogen-containing heterocycle optionally having substituent(s), or $R^2$ optionally form, together with the adjacent nitrogen atom, Y and Ar, a nitrogen-containing fused ring optionally having substituent(s), or a salt thereof.

7) WO2006/118320 (patent document 7) discloses a compound represented by the formula:

(I)

wherein
Ar is an optionally substituted ring;
A is a spacer having a main chain of 1 to 4 atoms;
B is a bond, a $C_{1-10}$ alkylene group or an oxygen atom;
$R^3$ and $R^5$ are each independently a hydrogen atom or a substituent;

$R^4$ is an optionally substituted cyclic group or an optionally substituted $C_{1-10}$ alkyl group;
$R^1$ and $R^2$ are each independently a hydrogen atom or a substituent, or $R^1$ is bonded to $R^2$ or B to form an optionally substituted nitrogen-containing heterocycle, or $R^1$ is bonded to Ar to form an optionally substituted nitrogen-containing fused heterocycle,
or a salt thereof.

8) As a γ secretase modulator, WO2009/076352 (patent document 8) discloses, for example, a compound represented by the following formula:

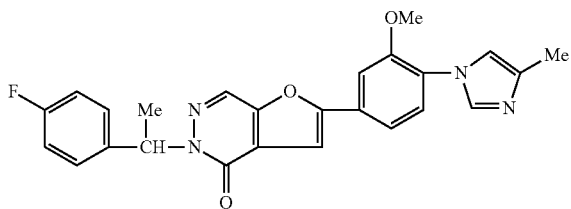 [SMILES: COc1cc(-c2cc3c(=O)n(C(C)c4ccc(F)cc4)ncc3o2)ccc1-n1cnc(C)c1]

9) Also, as a furan fused pyridinone, Synthesis, 2010, 10, 1741-1744 (non-patent document 2) discloses a compound represented by the following formula:

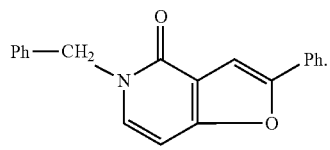 [SMILES: O=c1c2cc(-c3ccccc3)oc2ccn1Cc1ccccc1]

10) Moreover, the following compound A (CAS Registry Number 885901-19-9) and compound B (CAS Registry Number 885901-16-6) are known.

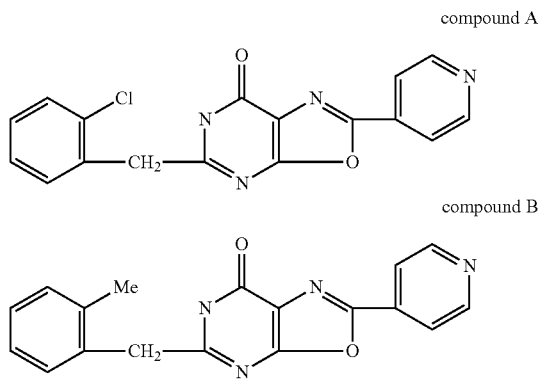

DOCUMENT LIST

Patent Documents patent document 1: WO2007/029847
patent document 2: WO2008/086409
patent document 3: WO2011/130086
patent document 4: WO2011/127643
patent document 5: WO2010/104830
patent document 6: WO01/82925
patent document 7: WO2006/118320
patent document 8: WO2009/076352

Non-Patent Documents non-patent document 1: Bioorg. Med. Chem. Lett., 20(23), 7015-7019 (2010)
non-patent document 2: Synthesis, 2010, 10, 1741-1744

SUMMARY OF THE INVENTION

Problems to be Solved by the Invention

The development of a compound having an MCH receptor antagonistic action and low toxicity, which is useful as an agent for the prophylaxis or treatment of obesity and the like is desired.

Means of Solving the Problems

The present inventors have conducted intensive studies of a compound having an MCH receptor antagonistic action and low toxicity [particularly, cardiotoxicity (e.g., human ether-a-go-go related gene (hERG) inhibitory activity), phospholipidosis (PLsis) inducing potential and the like, which sometimes pose problems in drug discovery], and found that compound (I) explained in the following has a superior MCH receptor antagonistic action and shows low toxicity such as cardiotoxicity (e.g., hERG inhibitory activity), PLsis inducing potential and the like as compared to conventional MCH receptor antagonists, which resulted in the completion of the present invention.

Accordingly, the present invention relates to
[1] a compound represented by the formula:

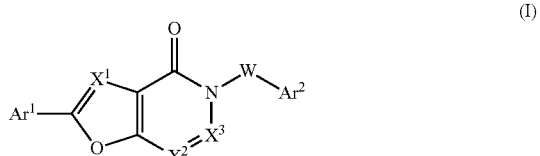

wherein
$Ar^1$ is a 5- or 6-membered aromatic ring group optionally substituted by 1 to 3 substituents selected from (1) a halogen atom, (2) a cyano group, (3) a nitro group, (4) an optionally substituted hydrocarbon group, (5) an optionally substituted nonaromatic heterocyclic group, (6) an optionally substituted hydroxy group, (7) an optionally substituted mercapto group, (8) an optionally substituted amino group, and (9) an acyl group;
$Ar^2$ is a 5- or 6-membered aromatic ring group substituted by 1 to 3 substituents selected from (1) a halogen atom, (2) a cyano group, (3) an optionally substituted hydrocarbon group, (4) an optionally substituted heterocyclic group, (5) an optionally substituted hydroxy group, (6) an optionally substituted mercapto group, (7) a substituted amino group, and (8) an acyl group;
$X^1$ is $CR^1$ or N;
$X^2$ and $X^3$ are each independently CH or N;
wherein two or more of $X^1$, $X^2$ and $X^3$ are not simultaneously N;
W is a bond, an optionally substituted $C_{1-6}$ alkylene group, or an optionally substituted $C_{2-6}$ alkenylene group;
when W is an optionally substituted $C_{1-6}$ alkylene group or an optionally substituted $C_{2-6}$ alkenylene group, it optionally forms an optionally substituted 4- to 7-membered nonaromatic ring together with the substituent of $Ar^2$; and $R^1$ is a hydrogen atom, a halogen atom, an optionally substituted $C_{1-6}$ alkyl group, an optionally substituted $C_{3-10}$ cycloalkyl group or an optionally substituted $C_{1-6}$ alkoxy group, or a salt thereof (hereinafter sometimes to be abbreviated as "compound (I)");

[2] the compound of the aforementioned [1], wherein $Ar^1$ is a 5- or 6-membered aromatic ring group optionally substituted by 1 to 3 substituents selected from (1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms, or a salt thereof;

[3] the compound of the aforementioned [1] or [2], wherein $Ar^2$ is a 5- or 6-membered aromatic ring group substituted by 1 to 3 substituents selected from (1) a halogen atom,
(2) a cyano group,
(3) a $C_{1-6}$ alkyl group optionally substituted by 1 to 3 hydroxy groups,
(4) a $C_{3-10}$ cycloalkyl group,
(5) a hydroxy group,
(6) a $C_{1-6}$ alkoxy group optionally substituted by 1 to 3 substituents selected from
  (a) a hydroxy group,
  (b) a carbamoyl group,
  (c) a $C_{3-10}$ cycloalkyl group optionally substituted by 1 to 3 substituents selected from a halogen atom and a cyano group, and
  (d) a 4- to 6-membered saturated heterocyclic group optionally substituted by 1 to 3 $C_{1-6}$ alkyl groups,
(7) a $C_{1-6}$ alkoxy-carbonyl group, and
(8) a carbamoyl group optionally substituted by a $C_{3-10}$ cycloalkyl-$C_{1-6}$ alkyl group, or a salt thereof;

[4] the compound of the aforementioned [1], [2] or [3], wherein $X^1$ is CH, or a salt thereof;

[5] the compound of the aforementioned [1], [2], [3] or [4], wherein W is a bond or a $C_{1-6}$ alkylene group; and when W is a $C_{1-6}$ alkylene group, it optionally forms a 4- to 7-membered nonaromatic ring together with the substituent of $Ar^2$, or a salt thereof;

[6] the compound of the aforementioned [1], wherein $Ar^1$ is a 5- or 6-membered aromatic ring group optionally substituted by 1 to 3 substituents selected from (1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms;

$Ar^2$ is a 5- or 6-membered aromatic ring group substituted by 1 to 3 substituents selected from (1) a halogen atom,
(2) a cyano group,
(3) a $C_{1-6}$ alkyl group optionally substituted by 1 to 3 hydroxy groups,
(4) a $C_{3-10}$ cycloalkyl group,
(5) a hydroxy group,
(6) a $C_{1-6}$ alkoxy group optionally substituted by 1 to 3 substituents selected from
  (a) a hydroxy group,
  (b) a carbamoyl group,
  (c) a $C_{3-10}$ cycloalkyl group optionally substituted by 1 to 3 substituents selected from a halogen atom and a cyano group, and
  (d) a 4- to 6-membered saturated heterocyclic group optionally substituted by 1 to 3 $C_{1-6}$ alkyl groups,
(7) a $C_{1-6}$ alkoxy-carbonyl group, and
(8) a carbamoyl group optionally substituted by a $C_{3-10}$ cycloalkyl-$C_{1-6}$ alkyl group;

$X^1$ is CH;

$X^2$ and $X^3$ are each CH, $X^2$ is N and $X^3$ is CH, or $X^2$ is CH and $X^3$ is N;

W is a bond or a $C_{1-6}$ alkylene group; and when W is a $C_{1-6}$ alkylene group, it optionally forms a 4- to 7-membered nonaromatic ring together with the substituent of $Ar^2$;

or a salt thereof;

[7] a medicament comprising the compound of the aforementioned [1], [2], [3], [4], [5] or [6], or a salt thereof;

[8] the medicament of the aforementioned [7], which is a melanin-concentrating hormone receptor antagonist;

[9] the medicament of the aforementioned [7], which is an anorexigenic agent;

[10] the medicament of the aforementioned [7], which is a prophylactic or therapeutic agent for obesity;

[11] a method of antagonizing a melanin-concentrating hormone receptor in a mammal, comprising administering an effective amount of the compound of the aforementioned [1], [2], [3], [4], [5] or [6] or a salt thereof to the mammal;

[12] a method of suppressing food intake in a mammal, comprising administering an effective amount of the compound of the aforementioned [1], [2], [3], [4], [5] or [6] or a salt thereof to the mammal;

[13] a method for the prophylaxis or treatment of obesity in a mammal, comprising administering an effective amount of the compound of the aforementioned [1], [2], [3], [4], [5] or [6] or a salt thereof to the mammal;

[14] use of the compound of the aforementioned [1], [2], [3], [4], [5] or [6] or a salt thereof for the production of a melanin-concentrating hormone receptor antagonist;

[15] use of the compound of the aforementioned [1], [2], [3], [4], [5] or [6] or a salt thereof for the production of an anorexigenic agent;

[16] use of the compound of the aforementioned [1], [2], [3], [4], [5] or [6] or a salt thereof for the production of a prophylactic or therapeutic agent for obesity;

[17] the compound of the aforementioned [1], [2], [3], [4], [5] or [6] or a salt thereof for use in antagonizing a melanin-concentrating hormone receptor;

[18] the compound of the aforementioned [1], [2], [3], [4], [5] or [6] or a salt thereof for use in suppressing food intake;

[19] the compound of the aforementioned [1], [2], [3], [4], [5] or [6] or a salt thereof for use in the prophylaxis or treatment of obesity;

and the like.

Compound (I) has a high MCH receptor antagonistic action, and low toxicity such as cardiotoxicity (e.g., hERG inhibitory activity), PLsis inducing potential and the like, as compared to conventional MCH receptor antagonists. Therefore, compound (I) is highly useful as an agent for the prophylaxis or treatment of obesity and the like.

DETAILED DESCRIPTION OF THE INVENTION

The definitions of the symbols and terms used in the present invention are described in detail in the following.

In the present specification, the "halogen atom" means, unless otherwise specified, a fluorine atom, a chlorine atom, a bromine atom or an iodine atom.

In the present specification, the "$C_{1-6}$ alkyl group" means, unless otherwise specified, methyl, ethyl, propyl, isopropyl, n-butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 1,2,2-trimethylpropyl, 3,3-dimethylbutyl, 2-ethylbutyl and the like.

In the present specification, the "$C_{1-6}$ alkyl group" of the "optionally substituted $C_{1-6}$ alkyl group" optionally has 1 to 5 (preferably, 1 to 3) substituents at substitutable position(s). Examples of such substituent include the following substituent group A. When two or more substituents are present, the respective substituents may be the same or different.

Substituent group A:
(1) a $C_{3-10}$ cycloalkyl group (e.g., cyclopropyl, cyclohexyl) optionally substituted by 1 to 3 substituents selected from a halogen atom and a cyano group;
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) a nonaromatic heterocyclic group (e.g., tetrahydrofuryl, morpholinyl, thiomorpholinyl, piperidinyl, pyrrolidinyl, piperazinyl, oxetanyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group (e.g., methylcarbonyl, ethylcarbonyl) optionally substituted by 1 to 3 halogen atoms,
  (c) a $C_{1-6}$ alkoxy-carbonyl group (e.g., methoxycarbonyl, ethoxycarbonyl) optionally substituted by 1 to 3 halogen atoms,
  (d) a carbamoyl group optionally mono- or di-substituted by $C_{1-6}$ alkyl group(s) optionally substituted by 1 to 3 halogen atoms (e.g., methylcarbamoyl, ethylcarbamoyl), and
  (e) a formyl group;
(6) a $C_{1-6}$ alkyl-carbonyl group (e.g., methylcarbonyl, ethylcarbonyl) optionally substituted by 1 to 3 halogen atoms;
(7) a $C_{1-6}$ alkoxy-carbonyl group optionally substituted by 1 to 3 substituents selected from
  (a) a halogen atom, and
  (b) a $C_{1-6}$ alkoxy group;
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_1$ 6 alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group,
  (e) an amino group optionally mono- or di-substituted by substituent(s) selected from a $C_{1-6}$ alkyl group and a $C_{1-6}$ alkoxy-carbonyl group,
  (f) a $C_{6-14}$ aryl group (e.g., phenyl),
  (g) a $C_{3-10}$ cycloalkyl group (e.g., cyclopropyl, cyclobutyl),
  (h) an aromatic heterocyclic group (e.g., thienyl, furyl), and
  (i) a hydroxy group;
(15) a $C_{2-6}$ alkenyloxy group (e.g., ethenyloxy) optionally substituted by 1 to 3 halogen atoms;
(16) a $C_{6-14}$ aryloxy group (e.g., phenyloxy, naphthyloxy);
(17) a $C_{1-6}$ alkyl-carbonyloxy group (e.g., acetyloxy, tert-butylcarbonyloxy);
(18) a $C_{6-14}$ aryl-carbonyl group (e.g., benzoyl) optionally substituted by 1 to 3 substituents selected from
  (a) a halogen atom, and
  (b) a $C_{1-6}$ alkyl group optionally substituted by 1 to 3 halogen atoms;
(19) a nonaromatic heterocyclylcarbonyl group (e.g., pyrrolidinylcarbonyl, morpholinylcarbonyl, 1,1-dioxidothiomorpholinylcarbonyl) optionally substituted by 1 to 3 $C_{1-6}$ alkyl groups optionally substituted by 1 to 3 halogen atoms;
(20) a mercapto group;
(21) a $C_{1-6}$ alkylthio group (e.g., methylthio, ethylthio) optionally substituted by 1 to 3 halogen atoms;
(22) a $C_{7-13}$ aralkylthio group (e.g., benzylthio);
(23) a $C_{6-14}$ arylthio group (e.g., phenylthio, naphthylthio);
(24) a cyano group;
(25) a nitro group;
(26) a halogen atom;
(27) a $C_{1-3}$ alkylenedioxy group;
(28) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 $C_{1-6}$ alkyl groups optionally substituted by 1 to 3 halogen atoms; and
(29) a hydroxyimino group optionally substituted by a $C_{1-6}$ alkyl group optionally substituted by 1 to 3 $C_{6-14}$ aryl groups (e.g., phenyl).

In the present specification, the "$C_{1-6}$ alkoxy group" means, unless otherwise specified, methoxy, ethoxy, propoxy, isopropoxy, butoxy, isobutoxy, sec-butoxy, tert-butoxy and the like.

In the present specification, the "$C_{1-6}$ alkoxy group" of the "optionally substituted $C_{1-6}$ alkoxy group" optionally has 1 to 5 (preferably, 1 to 3) substituents at substitutable position(s). Examples of such substituent include the above-mentioned substituent group A. When two or more substituents are present, the respective substituents may be the same or different.

In the present specification, the "$C_{3-10}$ cycloalkyl group" means, unless otherwise specified, cyclopropyl, cyclobutyl, cyclopentyl, cyclohexyl, cycloheptyl, cyclooctyl, adamantyl and the like.

In the present specification, the "$C_{3-10}$ cycloalkyl group" of the "optionally substituted $C_{3-10}$ cycloalkyl group" optionally has 1 to 5 (preferably, 1 to 3) substituents at substitutable position(s). Examples of such substituent include the following substituent group B. When two or more substituents are present, the respective substituents may be the same or different.

Substituent Group B:
(1) substituent group A;
(2) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group,
    (f) an amino group optionally mono- or di-substituted by $C_{1-6}$ alkyl group(s), and
    (g) a $C_{3-10}$ cycloalkyloxy group (e.g., cyclopropyloxy);
(3) a $C_{2-6}$ alkenyl group (e.g., ethenyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group,
    (f) an amino group optionally mono- or di-substituted by $C_{1-6}$ alkyl group(s), and
    (g) a $C_{3-10}$ cycloalkyl group (e.g., cyclopropyl);
(4) a $C_{2-6}$ alkynyl group (e.g., ethynyl) optionally substituted by 1 to 3 $C_{3-10}$ cycloalkyl groups (e.g., cyclopropyl, cyclobutyl);
(5) a $C_{7-13}$ aralkyl group (e.g., benzyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom; and
(6) an oxo group.

Unless otherwise specified, the "hydrocarbon group" means a $C_{1-6}$ alkyl group, a $C_{2-6}$ alkenyl group, a $C_{2-6}$ alkynyl group, a $C_{7-13}$ aralkyl group, an aromatic hydrocarbon group, a nonaromatic cyclic hydrocarbon group and the like.

Examples of the "$C_{2-6}$ alkenyl group" include vinyl, allyl, isopropenyl, butenyl, pentenyl, hexenyl and the like.

Examples of the "$C_{2-6}$ alkynyl group" include ethynyl, propargyl, butynyl, pentynyl, hexynyl and the like.

Examples of the "$C_{7-13}$ aralkyl group" include benzyl, phenethyl, 1-phenylethyl, 3-phenylpropyl, 1-naphthylmethyl, 2-naphthylmethyl and the like.

Examples of the "aromatic hydrocarbon group" include a $C_{6-14}$ aryl group. Examples of the $C_{6-14}$ aryl group include phenyl, naphthyl, anthracenyl, phenanthrenyl, acenaphthylenyl and the like.

Examples of the "nonaromatic cyclic hydrocarbon group" include a $C_{3-10}$ cycloalkyl group, a $C_{3-10}$ cycloalkenyl group, a $C_{4-10}$ cycloalkadienyl group and the like, each of which is optionally fused with a benzene ring.

Examples of the $C_{3-10}$ cycloalkenyl group include 2-cyclopenten-1-yl, 3-cyclopenten-1-yl, 2-cyclohexen-1-yl, 3-cyclohexen-1-yl and the like.

Examples of the $C_{4-10}$ cycloalkadienyl group include 2,4-cyclopentadien-1-yl, 2,4-cyclohexadien-1-yl, 2,5-cyclohexadien-1-yl and the like.

Each of the above-mentioned $C_{3-10}$ cycloalkyl group, $C_{3-10}$ cycloalkenyl group, and $C_{4-10}$ cycloalkadienyl group is optionally fused with a benzene ring. Examples of the fused ring group include indanyl, dihydronaphthyl, tetrahydronaphthyl, fluorenyl and the like.

The "hydrocarbon group" of the "optionally substituted hydrocarbon group" optionally has 1 to 7 (preferably, 1 to 3) substituents at substitutable position(s). When two or more substituents are present, the respective substituents may be the same or different. When the aforementioned "hydrocarbon group" is a $C_{1-6}$ alkyl group, a $C_{2-6}$ alkenyl group, a $C_{2-6}$ alkynyl group or the like, the substituents thereof are, for example, the above-mentioned substituent group A. When the aforementioned "hydrocarbon group" is a $C_{7-13}$ aralkyl group, an aromatic hydrocarbon group, a nonaromatic cyclic hydrocarbon group or the like, the substituents thereof are, for example, the above-mentioned substituent group B.

The "heterocyclic group" means an aromatic heterocyclic group or a nonaromatic heterocyclic group.

Examples of the "aromatic heterocyclic group" include a 5- to 10-membered monocyclic or bicyclic aromatic heterocyclic group, containing, as a ring-constituting atom besides carbon atom, 1 to 4 hetero atoms selected from an oxygen atom, a sulfur atom and a nitrogen atom.

Preferable examples of the "aromatic heterocyclic group" include 5- or 6-membered monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl, 1,2,4-triazin-5-yl, 1,2,4-triazin-6-yl) and the like;

8- to 10-membered bicyclic aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

Examples of the "nonaromatic heterocyclic group" include a 4- to 12-membered monocyclic or bicyclic nonaromatic heterocyclic group containing, besides carbon atom, 1 to 4 hetero atoms selected from an oxygen atom, a sulfur atom and a nitrogen atom.

Preferable examples of the "nonaromatic heterocyclic group" include
a 4- to 7-membered monocyclic nonaromatic heterocyclic group such as tetrahydrofuranyl (e.g., tetrahydrofuran-2-yl, tetrahydrofuran-3-yl), dihydrooxazolyl (e.g., 4,5-dihydro-1,3-oxazol-2-yl), oxetanyl (e.g., oxetan-3-yl), pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), pyrazolidinyl (e.g., pyrazolidin-1-yl), tetrahydropyrimidinyl and the like;
a 8- to 12-membered bicyclic nonaromatic heterocyclic group such as dihydroindolyl (e.g., 2,3-dihydro-1H-indol-1-yl), dihydroisoindolyl (e.g., 1,3-dihydro-2H-isoindol-2-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), benzazepanyl and the like; and the like.

The "heterocyclic group" of the "optionally substituted heterocyclic group" optionally has 1 to 5 (preferably, 1 to 3) substituents at substitutable position(s). Examples of such substituent include the above-mentioned substituent group B. When two or more substituents are present, the respective substituents may be the same or different.

The "nonaromatic heterocyclic group" of the "optionally substituted nonaromatic heterocyclic group" optionally has 1 to 5 (preferably, 1 to 3) substituents at substitutable position(s). Examples of such substituent include the above-mentioned substituent group B can be mentioned. When two or more substituents are present, the respective substituents may be the same or different.

Examples of the "optionally substituted hydroxy group" include a hydroxy group, an optionally substituted $C_{1-6}$ alkoxy group, an optionally substituted $C_{2-6}$ alkenyloxy group, an optionally substituted $C_{2-6}$ alkynyloxy group, an optionally substituted $C_{6-14}$ aryloxy group, an optionally substituted $C_{3-10}$ cycloalkyloxy group and the like.

Preferable examples of the "optionally substituted hydroxy group" include
a hydroxy group,
a $C_{1-6}$ alkoxy group optionally substituted by 1 to 3 substituents selected from substituent group A,
a $C_{2-6}$ alkenyloxy group optionally substituted by 1 to 3 substituents selected from substituent group A,
a $C_{2-6}$ alkynyloxy group optionally substituted by 1 to 3 substituents selected from substituent group A,
a $C_{6-14}$ aryloxy group optionally substituted by 1 to 3 substituents selected from substituent group B,
a $C_{3-10}$ cycloalkyloxy group optionally substituted by 1 to 3 substituents selected from substituent group B and the like.

Examples of the "optionally substituted mercapto group" include a mercapto group, an optionally substituted $C_{1-6}$ alkylthio group, an optionally substituted $C_{2-6}$ alkenylthio group, an optionally substituted $C_{2-6}$ alkynylthio group, an optionally substituted $C_{6-14}$ arylthio group, an optionally substituted $C_{3-10}$ cycloalkylthio group and the like.

Preferable examples of the "optionally substituted mercapto group" include
a mercapto group,
a $C_{1-6}$ alkylthio group optionally substituted by 1 to 3 substituents selected from substituent group A,
a $C_{2-6}$ alkenylthio group optionally substituted by 1 to 3 substituents selected from substituent group A,
a $C_{2-6}$ alkynylthio group optionally substituted by 1 to 3 substituents selected from substituent group A,
a $C_{6-14}$ arylthio group optionally substituted by 1 to 3 substituents selected from substituent group B,
a $C_{3-10}$ cycloalkylthio group optionally substituted by 1 to 3 substituents selected from substituent group B and the like.

The "optionally substituted amino group" means an amino group optionally substituted by 1 or 2 substituents. Examples of such substituent include (1) to (12), (18), (19) and (28) of the above-mentioned substituent group A, and (2) to (5) of the above-mentioned substituent group B. When two or more substituents are present, the respective substituents may be the same or different.

The "substituted amino group" means an amino group substituted by 1 or 2 substituents. Examples of such substituent include (1) to (12), (18), (19) and (28) of the above-mentioned substituent group A, and (2) to (5) of the above-mentioned substituent group B. When two or more substituents are present, the respective substituents may be the same or different.

The "acyl group" is, for example, a group represented by the formula: —$COR^A$, —CO—$OR^A$, —$SO_3RA$, —$S(O)_2R^A$, —$SOR^A$, —CO—$NR^{A'}R^{B'}$, —CS—$NR^{A'}R'$, —$S(O)_2NR^{A'}R^{B'}$ wherein $R^A$ is a hydrogen atom, an optionally substituted hydrocarbon group, or an optionally substituted heterocyclic group, $R^{A'}$ and $R^{B'}$ are the same or different and each is a hydrogen atom, an optionally substituted hydrocarbon group, or an optionally substituted heterocyclic group, or $R^{A'}$ and $R^{B'}$ optionally form, together with the adjacent nitrogen atom, an optionally substituted nitrogen-containing heterocycle, and the like.

Examples of the "nitrogen-containing heterocycle" of the "optionally substituted nitrogen-containing heterocycle"

formed by $R^{A'}$ and $R^{B'}$ together with the adjacent nitrogen atom include a 5- to 7-membered nitrogen-containing heterocycle containing at least one nitrogen atom as a ring-constituting atom besides carbon atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable position(s). Examples of such substituent include the above-mentioned substituent group B. When the number of the substituents is two or more, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a $C_{3-10}$ cycloalkyl group, a $C_{1-6}$ alkoxy group, a $C_{1-6}$ alkoxy-carbonyl group and a carboxy group, and
  (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a nonaromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms; and the like.

The "5- or 6-membered aromatic ring group" means a phenyl group or a 5- or 6-membered aromatic heterocyclic group.

Examples of the "5- or 6-membered aromatic heterocyclic group" include a 5- or 6-membered aromatic heterocyclic group, containing, as a ring-constituting atom besides carbon atom, 1 to 4 hetero atoms selected from an oxygen atom, a sulfur atom and a nitrogen atom.

Preferable examples of the "5- or 6-membered aromatic heterocyclic group" include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl, 1,2,4-triazin-5-yl, 1,2,4-triazin-6-yl) and the like.

The "$C_{1-6}$ alkylene group" means, unless otherwise specified, —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —CH(CH$_2$CH$_3$)—, —CH(CH(CH$_3$)$_2$)—, —C(CH$_3$)$_2$—, —CH$_2$—CH(CH$_3$)—, —CH(CH$_3$)—CH$_2$—, —(CH(CH$_3$))$_2$—, —(CH$_2$)$_2$—C(CH$_3$)$_2$—, —(CH$_2$)$_3$—C(CH$_3$)$_2$—, —CH(CH$_3$)—(CH$_2$)$_2$— and the like.

The "$C_{1-6}$ alkylene group" of the "optionally substituted $C_{1-6}$ alkylene group" optionally has 1 to 5 (preferably, 1 to 3) substituents at substitutable position(s). Examples of such substituent include the following substituent group C. When two or more substituents are present, the respective substituents may be the same or different.

Substituent Group C:
(1) substituent group A; and
(2) an oxo group.

The "$C_{2-6}$ alkenylene group" means, unless otherwise specified, —CH=CH—, —CH=CH—CH$_2$—, —CH$_2$—CH=CH—, —C(CH$_3$)$_2$—CH=CH—, —CH$_2$—CH=CH—CH$_2$—, —CH$_2$—CH$_2$—CH=CH—, —CH=CH—CH=CH—, —C(CH$_3$)=CH—, —CH=C(CH$_3$)—, —CH=C(CH$_2$CH$_3$)— and the like.

The "$C_{2-6}$ alkenylene group" of the "optionally substituted $C_{2-6}$ alkenylene group" optionally has 1 to 5 (preferably, 1 to 3) substituents at substitutable position(s). Examples of such substituent include the above-mentioned substituent group C. When two or more substituents are present, the respective substituents may be the same or different.

In the above-mentioned formula (I), preferable groups are as described below.

$Ar^1$ is a 5- or 6-membered aromatic ring group optionally substituted by 1 to 3 substituents selected from (1) a halogen atom, (2) a cyano group, (3) a nitro group, (4) an optionally substituted hydrocarbon group, (5) an optionally substituted nonaromatic heterocyclic group, (6) an optionally substituted hydroxy group, (7) an optionally substituted mercapto group, (8) an optionally substituted amino group, and (9) an acyl group.

$Ar^1$ is preferably
a 5- or 6-membered aromatic ring group (preferably, a phenyl group or a 5- or 6-membered aromatic ring group containing, besides carbon atom, 1 to 4 hetero atoms selected from an oxygen atom, a sulfur atom and a nitrogen atom, for example, phenyl, pyridyl, thienyl, thiazolyl, pyrazolyl, pyrimidinyl, furyl) optionally substituted by 1 to 3 substituents selected from
(1) a halogen atom (e.g., a fluorine atom, a chlorine atom),
(2) a cyano group,
(3) a $C_{1-6}$ alkyl group optionally substituted by 1 to 3 halogen atoms (e.g., trifluoromethyl group), and
(4) a $C_{1-6}$ alkoxy group optionally substituted by 1 to 3 halogen atoms (e.g., methoxy, trifluoromethoxy).

$Ar^1$ is more preferably a phenyl group, a pyridyl group (e.g., pyridin-2-yl, pyridin-3-yl, pyridin-4-yl), a thienyl group (e.g., thiophen-2-yl, thiophen-3-yl), a thiazolyl group (e.g., thiazol-2-yl, thiazol-5-yl), a pyrazolyl group (e.g., pyrazol-3-yl), a pyrimidinyl group (e.g., pyrimidin-2-yl) or a furyl group (e.g., furan-2-yl), each of which is optionally substituted by 1 to 3 substituents selected from
(1) a halogen atom (e.g., a fluorine atom, a chlorine atom),
(2) a cyano group,
(3) a $C_{1-6}$ alkyl group optionally substituted by 1 to 3 halogen atoms (e.g., trifluoromethyl group), and
(4) a $C_{1-6}$ alkoxy group optionally substituted by 1 to 3 halogen atoms (e.g., methoxy, trifluoromethoxy).

$Ar^1$ is more preferably a phenyl group, a pyridyl group (e.g., pyridin-2-yl, pyridin-3-yl, pyridin-4-yl), a thienyl group (e.g., thiophen-2-yl, thiophen-3-yl) or a furyl group (e.g., furan-2-yl), each of which is optionally substituted by 1 to 3 substituents selected from
(1) a halogen atom (e.g., a fluorine atom, a chlorine atom),
(2) a cyano group,
(3) a $C_{1-6}$ alkyl group optionally substituted by 1 to 3 halogen atoms (e.g., trifluoromethyl group), and
(4) a $C_{1-6}$ alkoxy group optionally substituted by 1 to 3 halogen atoms (e.g., methoxy, trifluoromethoxy).

$Ar^1$ is furthermore preferably
a 5- or 6-membered aromatic ring group (e.g., phenyl, pyridyl, thienyl) optionally substituted by 1 to 3 substituents selected from
(1) a halogen atom (e.g., a fluorine atom, a chlorine atom),
(2) a $C_{1-6}$ alkyl group optionally substituted by 1 to 3 halogen atoms (e.g., trifluoromethyl group), and
(3) a $C_{1-6}$ alkoxy group optionally substituted by 1 to 3 halogen atoms (e.g., methoxy, trifluoromethoxy).

Particularly preferable examples of $Ar^1$ include phenyl, 4-fluorophenyl, 4-chlorophenyl, 4-methylphenyl, 4-(trifluoromethyl)phenyl, 4-methoxyphenyl, 3-methoxyphenyl, 4-(trifluoromethoxy)phenyl, 4-cyanophenyl, 2-fluorophenyl, 3-fluorophenyl, 2,4-difluorophenyl, 3,4-difluorophenyl, 3,5-difluorophenyl, 4-chloro-3-fluorophenyl, pyridin-2-yl, pyridin-3-yl, pyridin-4-yl, 5-chloropyridin-2-yl, 5-fluoropyridin-2-yl, 5-methylpyridin-2-yl, 5-(trifluoromethyl)pyridin-2-yl, thiophen-2-yl, thiophen-3-yl, 5-chlorothiophen-2-yl, 5-fluorothiophen-2-yl, 5-trifluoromethylthiophen-2-yl, 5-chlorothiophen-3-yl, 5-fluorothiophen-3-yl, 5-trifluoromethylthiophen-3-yl, 4,5-difluorothiophen-2-yl, 4-chloro-5-fluorothiophen-2-yl, 5-chloro-4-fluorothiophen-2-yl, furan-2-yl, 5-chlorofuran-2-yl, 5-trifluoromethylfuran-2-yl and the like.

$Ar^2$ is a 5- or 6-membered aromatic ring group substituted by 1 to 3 substituents selected from (1) a halogen atom, (2) a cyano group, (3) an optionally substituted hydrocarbon group, (4) an optionally substituted heterocyclic group, (5) an optionally substituted hydroxy group, (6) an optionally substituted mercapto group, (7) a substituted amino group, and (8) an acyl group.

$Ar^2$ is preferably a 5- or 6-membered aromatic ring group (preferably, a phenyl group or a 5- or 6-membered aromatic heterocyclic group containing, as a ring-constituting atom besides carbon atom, 1 to 4 hetero atoms selected from an oxygen atom, a sulfur atom and a nitrogen atom, for example, phenyl, pyridyl) substituted by 1 to 3 substituents selected from
(1) a halogen atom,
(2) a cyano group,
(3) a $C_{1-6}$ alkyl group optionally substituted by 1 to 3 substituents selected from substituent group A,
(4) a $C_{3-10}$ cycloalkyl group optionally substituted by 1 to 3 substituents selected from substituent group B,
(5) a hydroxy group,
(6) a $C_{1-6}$ alkoxy group optionally substituted by 1 to 3 substituents selected from substituent group A,
(7) a $C_{1-6}$ alkoxy-carbonyl group optionally substituted by 1 to 3 halogen atoms, and
(8) a carbamoyl group optionally mono- or di-substituted by $C_{1-6}$ alkyl group(s) optionally substituted by 1 to 3 substituents selected from a halogen atom, a $C_{3-10}$ cycloalkyl group, a $C_{1-6}$ alkoxy group, a $C_{1-6}$ alkoxy-carbonyl group and a carboxy group.

$Ar^2$ is more preferably a 5- or 6-membered aromatic ring group (preferably, a phenyl group or a 5- or 6-membered aromatic heterocyclic group containing, as a ring-constituting atom besides carbon atom, 1 to 4 hetero atoms selected from an oxygen atom, a sulfur atom and a nitrogen atom, for example, phenyl, pyridyl) substituted by 1 to 3 substituents selected from
(1) a halogen atom (e.g., a chlorine atom, a bromine atom),
(2) a cyano group,
(3) a $C_{1-6}$ alkyl group optionally substituted by 1 to 3 hydroxy groups,
(4) a $C_{3-10}$ cycloalkyl group (e.g., cyclopentyl, cyclohexyl),
(5) a hydroxy group,
(6) a $C_{1-6}$ alkoxy group optionally substituted by 1 to 3 substituents selected from
  (a) a hydroxy group,
  (b) a carbamoyl group,
  (c) a $C_{3-10}$ cycloalkyl group (e.g., cyclopropyl, cyclopentyl) optionally substituted by 1 to 3 substituents selected from a halogen atom and a cyano group, and
  (d) a 4- to 6-membered saturated heterocyclic group (preferably, a 4- to 6-membered saturated heterocyclic group containing one oxygen atom as a ring-constituting atom besides carbon atom, for example, tetrahydrofuranyl, oxetanyl) optionally substituted by 1 to 3 $C_{1-6}$ alkyl groups,
(7) a $C_{1-6}$ alkoxy-carbonyl group, and
(8) a carbamoyl group optionally substituted by a $C_{3-10}$ cycloalkyl-$C_{1-6}$ alkyl group (e.g., cyclopropylmethyl).

$X^1$ is $CR^1$ or N, and $X^2$ and $X^3$ are independently CH or N, wherein two or more of $X^1$, $X^2$ and $X^3$ are not simultaneously N.

$X^1$ is preferably $CR^1$.

$R^1$ is a hydrogen atom, a halogen atom, an optionally substituted $C_{1-6}$ alkyl group, an optionally substituted $C_{3-10}$ cycloalkyl group, or an optionally substituted $C_{1-6}$ alkoxy group.

$R^1$ is preferably
a hydrogen atom,
a halogen atom,
a $C_{1-6}$ alkyl group optionally substituted by 1 to 3 substituents selected from substituent group A,
a $C_{3-10}$ cycloalkyl group optionally substituted by 1 to 3 substituents selected from substituent group B, or
a $C_{1-6}$ alkoxy group optionally substituted by 1 to 3 substituents selected from substituent group A.

$R^1$ is more preferably
a hydrogen atom, or
a $C_{1-6}$ alkyl group optionally substituted by 1 to 3 substituents selected from a halogen atom, a hydroxy group and a $C_{1-6}$ alkoxy group.

$R^1$ is further preferably a hydrogen atom or a $C_{1-6}$ alkyl group, particularly preferably a hydrogen atom.

$X^1$ is preferably CH.

$X^2$ and $X^3$ are each independently CH or N.
The combination of $X^2$ and $X^3$ is
$X^2$ and $X^3$ each being CH,
$X^2$ being N and $X^3$ being CH, or
$X^2$ being CH and $X^3$ being N.

The combination of $X^2$ and $X^3$ is preferably $X^2$ and $X^3$ each being CH, or $X^2$ being N and $X^3$ being CH.

A group represented by the formula

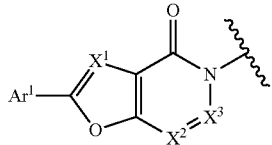

is

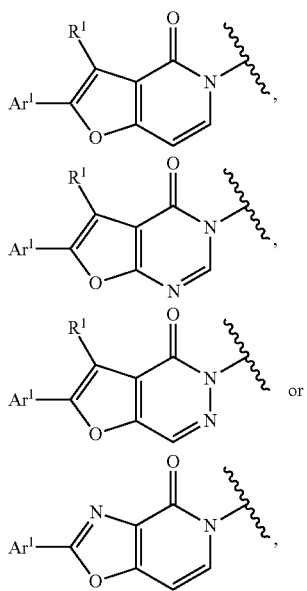

preferably

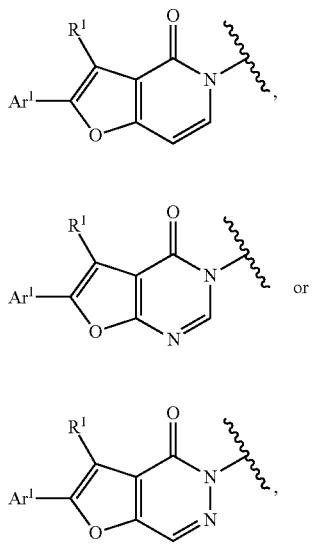

more preferably

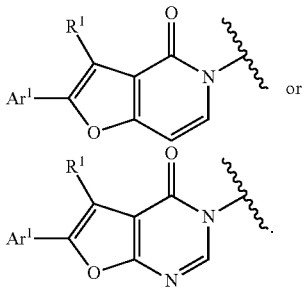

W is a bond, an optionally substituted $C_{1-6}$ alkylene group, or an optionally substituted $C_{2-6}$ alkenylene group, and when W is an optionally substituted $C_{1-6}$ alkylene group, or optionally substituted $C_{2-6}$ alkenylene group, it optionally forms an optionally substituted 4- to 7-membered nonaromatic ring together with the substituent of $Ar^2$.

As the "4- to 7-membered nonaromatic ring" of the "optionally substituted 4- to 7-membered nonaromatic ring", 4- to 7-membered cycloalkene or cycloalkadiene can be mentioned.

Preferable examples of the 4- to 7-membered cycloalkene or cycloalkadiene include cyclobutene, cyclopentene, cyclohexene, cycloheptene, cyclohexadiene, cycloheptadiene and the like.

The "4- to 7-membered nonaromatic ring" of the "optionally substituted 4- to 7-membered nonaromatic ring" optionally has 1 to 5 (preferably, 1 to 3) substituents at substitutable position(s). Examples of such substituent include the above-mentioned substituent group B. When two or more substituents are present, the respective substituents may be the same or different.

W is preferably a bond, a $C_{1-6}$ alkylene group optionally substituted by 1 to 3 substituents selected from substituent group C, or a $C_{2-6}$ alkenylene group optionally substituted by 1 to 3 substituents selected from substituent group C, and when W is an optionally substituted $C_{1-6}$ alkylene group, or an optionally substituted $C_{2-6}$ alkenylene group, it optionally forms, together with the substituent of $Ar^2$, a 4- to 7-membered nonaromatic ring (preferably, 4- to 7-membered cycloalkene or cycloalkadiene) optionally substituted by 1 to 3 substituents selected from substituent group B.

W is more preferably a bond, a $C_{1-6}$ alkylene group optionally substituted by 1 to 3 substituents selected from an oxo group and a hydroxy group, or a $C_{2-6}$ alkenylene group optionally substituted by 1 to 3 substituents selected from an oxo group and a hydroxy group, and when W is an optionally substituted $C_{1-6}$ alkylene group, or an optionally substituted $C_{2-6}$ alkenylene group, it optionally forms, together with the substituent of $Ar^2$, a 4- to 7-membered nonaromatic ring (preferably, 4- to 7-membered cycloalkene or cycloalkadiene) optionally substituted by 1 to 3 substituents selected from an oxo group and a hydroxy group.

W is more preferably a bond or a $C_{1-6}$ alkylene group, and when W is a $C_{1-6}$ alkylene group, it optionally forms a 4- to 7-membered nonaromatic ring (preferably, 4- to 7-membered cycloalkene, for example, cyclohexene), together with the substituent of $Ar^2$.

W is particularly preferably a bond.

Preferable examples of compound (I) include the following compounds.

[Compound (I-A)]

Compound (I) wherein $Ar^1$ is a 5- or 6-membered aromatic ring group (preferably, a phenyl group or a 5- or 6-membered aromatic heterocyclic group containing, as a ring-constituting atom besides carbon atom, 1 to 4 hetero atoms selected from an oxygen atom, a sulfur atom and a nitrogen atom, for example, phenyl, pyridyl, thienyl) optionally substituted by 1 to 3 substituents selected from
(1) a halogen atom (e.g., fluorine atom, chlorine atom),
(2) a $C_{1-6}$ alkyl group optionally substituted by 1 to 3 halogen atoms (e.g., trifluoromethyl), and
(3) a $C_{1-6}$ alkoxy group optionally substituted by 1 to 3 halogen atoms (e.g., methoxy, trifluoromethoxy);

$Ar^2$ is a 5- or 6-membered aromatic ring group (preferably, a phenyl group or a 5- or 6-membered aromatic heterocyclic group containing, as a ring-constituting atom besides carbon atom, 1 to 4 hetero atoms selected from an oxygen atom, a sulfur atom and a nitrogen atom, for example, phenyl, pyridyl) substituted by 1 to 3 substituents selected from
(1) a halogen atom (e.g., chlorine atom, bromine atom),
(2) a cyano group,
(3) a $C_{1-6}$ alkyl group optionally substituted by 1 to 3 hydroxy groups,
(4) a $C_{3-10}$ cycloalkyl group (e.g., cyclopentyl, cyclohexyl),
(5) a hydroxy group,
(6) a $C_{1-6}$ alkoxy group optionally substituted by 1 to 3 substituents selected from
　(a) a hydroxy group,
　(b) a carbamoyl group,
　(c) a $C_{3-10}$ cycloalkyl group (e.g., cyclopropyl, cyclopentyl) optionally substituted by 1 to 3 substituents selected from a halogen atom and a cyano group, and
　(d) a 4- to 6-membered saturated heterocyclic group (preferably, a 4- to 6-membered saturated heterocyclic group containing one oxygen atom as a ring-constituting atom besides carbon atom, for example, tetrahydrofuranyl, oxetanyl) optionally substituted by 1 to 3 $C_{1-6}$ alkyl groups,
(7) a $C_{1-6}$ alkoxy-carbonyl group, and
(8) a carbamoyl group optionally substituted by a $C_{3-10}$ cycloalkyl-$C_{1-6}$ alkyl group (e.g., cyclopropylmethyl);

$X^1$ is CH;
$X^2$ and $X^3$ are each CH,
$X^2$ is N and $X^3$ is CH, or
$X^2$ is CH and $X^3$ is N;
W is a bond or a $C_{1-6}$ alkylene group;
and when W is a $C_{1-6}$ alkylene group, it optionally forms a 4- to 7-membered nonaromatic ring (preferably, 4- to 7-membered cycloalkene, for example, cyclohexene), together with the substituent of $Ar^2$.

[Compound (I-B)]

A compound represented by the formula:

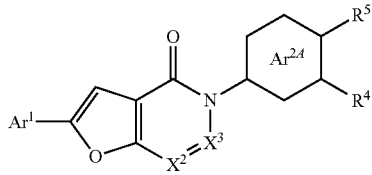

(I-B)

wherein
$Ar^1$ is a 5- or 6-membered aromatic ring group (preferably, a phenyl group or a 5- or 6-membered heterocyclic group containing, besides carbon atom, 1 to 4 hetero atoms selected from an oxygen atom, a sulfur atom and a nitrogen atom, for example, phenyl, thienyl, pyridyl) optionally substituted by 1 to 3 substituents selected from
(1) a halogen atom (e.g., fluorine atom, chlorine atom),
(2) a $C_{1-6}$ alkyl group optionally substituted by 1 to 3 halogen atoms (e.g., trifluoromethyl), and
(3) a $C_{1-6}$ alkoxy group optionally substituted by 1 to 3 halogen atoms (e.g., methoxy, trifluoromethoxy);

$X^2$ and $X^3$ are each CH, or
$X^2$ is N and $X^3$ is CH;
ring $Ar^{2A}$ is a benzene ring or a pyridine ring;
$R^4$ is a halogen atom, a $C_{1-6}$ alkyl group or a $C_{1-6}$ alkoxy group;
$R^5$ is
(1) a hydroxy group,
(2) a $C_{1-6}$ alkoxy group optionally substituted by 1 to 3 substituents selected from a hydroxy group and a carbamoyl group,
(3) a carbamoyl group optionally substituted by a $C_{3-10}$ cycloalkyl-$C_{1-6}$ alkyl group (e.g., cyclopropylmethyl), or
(4) a group represented by the formula —O—CH$_2$—R$^6$ wherein R$^6$ is
(a) a $C_{3-10}$ cycloalkyl group (e.g., cyclopropyl) optionally substituted by 1 to 3 substituents selected from a halogen atom and a cyano group, or
(b) a 4- to 6-membered saturated heterocyclic group (preferably, a 4- to 6-membered saturated heterocyclic group containing one oxygen atom as a ring-constituting atom besides carbon atom, for example, tetrahydrofuranyl, oxetanyl) optionally substituted by 1 to 3 $C_{1-6}$ alkyl groups,
or a salt thereof.

More preferable examples of compound (I) include those described in the following Examples and salts thereof.

When compound (I) is in the form of a salt, concrete examples thereof include pharmaceutically acceptable salts, for example, salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N'-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Compound (I) may be any of an anhydrate or a hydrate. In addition, compound (I) may be any of non-solvate and solvate.

Moreover, compound (I) may be labeled with an isotope (e.g., $^{3}H$, $^{11}C$, $^{14}C$, $^{18}F$, $^{35}S$, $^{125}I$).

Furthermore, compound (I) may also be a deuterium exchange compound wherein $^{1}H$ is converted to $^{2}H(D)$.

Compound (I) labeled with or substituted by an isotope can be used, for example, as a tracer used for Positron Emission Tomography (PET) (PET tracer), and is useful in the field of medical diagnosis and the like.

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity, solubility, stability etc.) at room temperature. The cocrystal and cocrystal salt can be produced according to a cocrystallization method known per se.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se (e.g., a fractional recrystallization method, a chiral column method, a diastereomer method).

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., fractional recrystallization, a chromatography method) and the like, and is subjected to a chemical treatment such as hydrolysis and the like to separate an optically active reagent moiety, whereby an optical isomer is obtained. For example, when compound (I) contains a hydroxy group, or a primary or secondary amino group in a molecule, the compound and an optically active organic acid (e.g., MTPA [α-methoxy-α-(trifluoromethyl) phenylacetic acid], (−)-menthoxyacetic acid) and the like are subjected to condensation reaction to give diastereomers in the ester form or in the amide form, respectively. When compound (I) has a carboxyl group, this compound and an optically active amine or alcohol are subjected to condensation reaction to give diastereomers in the amide form or in the ester form, respectively. The separated diastereomer is converted to an optical isomer of the original compound by acid hydrolysis or base hydrolysis.

Compound (I) may also be a prodrug, and a prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);

a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);

a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like.

Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

The production methods of compound (I) are explained in the following.

Compound (I) can be produced by, for example, a method shown below or a method analogous thereto, though not limited thereto.

In each of the following schemes, each starting compound may form a salt as long as it does not inhibit the reaction and, as the salt, those exemplified as the salt of the compound represented by the aforementioned formula (I) is used.

In each of the following schemes, as the starting compound, unless specific production method is stated, a commercially available one is easily available, or can be produced by a method known per se or a method analogous thereto.

A solvent to be used for the reaction of each of the following schemes is not particularly limited as long as it does not inhibit the reaction and dissolves the starting material to some extent. Examples thereof include aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, 1,2-dimethoxyethane and the like; ketones such as acetone, 2-butanone and the like; nitriles such as acetonitrile, propionitrile and the like; esters such as ethyl acetate, isopropyl acetate, tert-butyl acetate and the like; amides such as N,N-dimethylformamide, N,N-dimethylacetamide, 1-methyl-2-pyrrolidinone and the like; imides such as 1,3-dimethyl-2-imidazolidinone and the like; alcohols such as methanol, ethanol, isopropanol, tert-butanol and the like; halogenated hydrocarbons such as chloroform, dichloromethane, 1,2-dichloroethane, carbon tetrachloride and the like; sulfoxides such as dimethyl sulfoxide and the like; water and the like. These solvents may be mixed and used at an appropriate ratio. The reaction temperature is not higher than the boiling points of the aforementioned solvents, and is generally −100° C. to 250° C. In some cases, pressure-resistant reaction conditions and the like may be employed, and the reaction may be performed at a temperature not lower than the boiling point of the solvent. The reaction time is generally 0.5 hr to 100 hr.

In each of the following reactions, the "room temperature" means 15° C. to 30° C.

Compound (I) can be produced, for example, by reacting compound (2) with compound (3) shown in the following production method 1-1.

[Production Method 1-1]

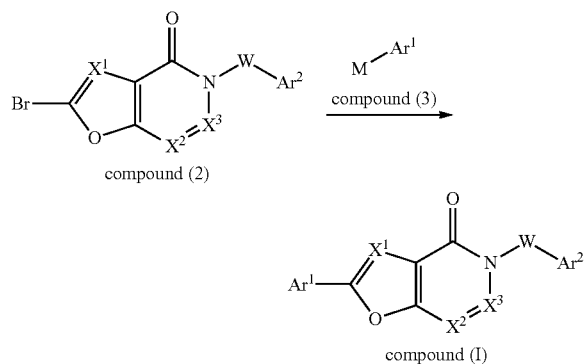

compound (2)

compound (I)

wherein M is a metal (e.g., boric acid, borate, alkyltin, zinc, magnesium halide and the like), and other symbols are each as defined above.

In production method 1-1, compound (I) is obtained using about 1.0 to 10.0 mol, preferably about 1.0 to 5.0 mol, of compound (3), about 1.0 to 10.0 mol, preferably about 1.0 to 5.0 mol, of a base, and about 0.000001 to 5 mol, preferably about 0.0001 to 2 mol, of a metal catalyst, per 1 mol of compound (2).

Examples of the base include inorganic salts such as potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

Examples of the metal catalyst include copper and a salt thereof (e.g., copper(II) acetate, copper(II) iodide and the like), palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, palladium compounds are preferable.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, 1,2-dimethoxyethane and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide, and the like, and the like. Two or more kinds of these solvents may be mixed and used at an appropriate ratio. Furthermore, water may be mixed at an appropriate ratio.

The reaction time is generally 15 min to 60 hr, preferably 30 min to 24 hr. The reaction temperature is from room temperature to 250° C., preferably 50° C. to 200° C. This reaction may be performed in a microwave reactor, for which the reaction time is generally 5 min to 24 hr, preferably 30 min to 2 hr. The reaction temperature is generally room temperature to 250° C., preferably 50° C. to 200° C.

In addition, this reaction may be performed using a ligand. As the ligand, organic amine compounds such as N,N'-dimethylethylenediamine, N,N'-dimethylcyclohexane-1,2-diamine, 2,2'-bipyridyl and the like; organic phosphorus compounds such as triphenylphosphine, tri-tert-butylphosphine, tricyclohexylphosphine, BINAP (2,2'-bis(diphenylphosphino)-1,1'-binaphthyl) and the like can be mentioned. The amount of the ligand to be used is generally about 1.0 to 10.0 mol, preferably about 1.0 to 5.0 mol, relative to the metal catalyst per mol.

The obtained compound (2) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2) can be produced according to the method described in the following production method or a method analogous thereto, or a method known per se.

Compound (3) may be a commercially available reagent, or can be produced by a method known per se.

Compound (Ia) which is compound (I) wherein W is a bond can be produced by, as another method, for example, reacting compound (4) with compound (5) shown in the following production method 1-2.

[Production Method 1-2]

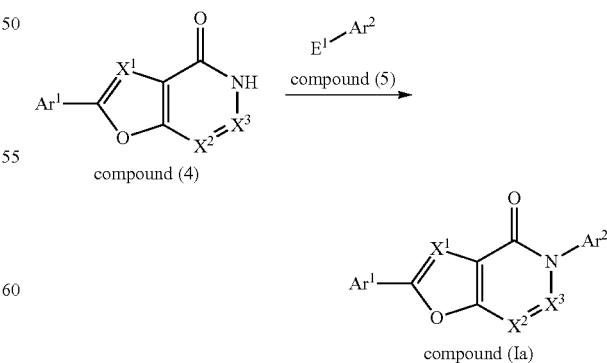

compound (4)

compound (Ia)

wherein $E^1$ is a leaving group (e.g., a halogen atom such as chlorine, bromine, iodine and the like, substituted sulfonic acid ester such as methanesulfonic acid ester, p-toluenesulfonic acid ester and the like, boronic acid etc.), and other symbols are each as defined above.

In production method 1-2, compound (Ia) is obtained using about 1.0 to 10.0 mol, preferably about 1.0 to 5.0 mol, of compound (5), about 1.0 to 10.0 mol, preferably about 1.0 to 5.0 mol, of a base, and about 0.000001 to 5 mol, preferably about 0.0001 to 2 mol, of a metal catalyst, per 1 mol of compound (4).

Examples of the base include inorganic salts such as potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

Examples of the metal catalyst include copper and a salt thereof (e.g., copper(II) acetate, copper(II) iodide and the like), palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, copper and a salt thereof are preferable.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; water and the like. Two or more kinds of these solvents may be mixed and used at an appropriate ratio.

The reaction time is generally 15 min to 60 hr, preferably 30 min to 24 hr. The reaction temperature is from room temperature to 250° C., preferably 50° C. to 200° C. This reaction may be performed in a microwave reactor, for which the reaction time is generally 5 min to 24 hr, preferably 30 min to 2 hr. The reaction temperature is generally room temperature to 250° C., preferably 50° C. to 200° C.

In addition, this reaction may be performed using a ligand. As the ligand, organic amine compounds such as N,N'-dimethylethylenediamine, N,N'-dimethylcyclohexane-1,2-diamine, 2,2-bipyridyl and the like; organic phosphorus compounds such as triphenylphosphine, tri-tert-butylphosphine, tricyclohexylphosphine, BINAP (2,2'-bis(diphenylphosphino)-1,1'-binaphthyl) and the like can be mentioned. The amount of the ligand to be used is generally about 1.0 to 10.0 mol, preferably about 1.0 to 5.0 mol, relative to the metal catalyst per mol.

The obtained compound (Ia) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (4) can be produced according to the method described in the following production method or a method analogous thereto, or a method known per se.

Compound (5) may be a commercially available reagent or can be produced according to the method described in the following production method or a method analogous thereto, or a method known per se.

Compound (Ib) which is compound (I) wherein W is an optionally substituted $C_{1-6}$ alkylene group or an optionally substituted $C_{2-6}$ alkenylene group can be produced by, as another method, for example, reacting compound (4) with compound (6) shown in the following production method 1-3.

[Production Method 1-3]

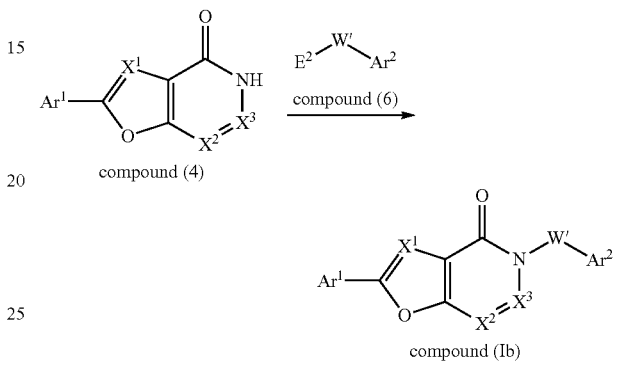

wherein $E^2$ is a leaving group (e.g., a halogen atom such as chlorine, bromine, iodine and the like, substituted sulfonic acid ester such as methanesulfonic acid ester, p-toluenesulfonic acid ester etc., and the like), W' is an optionally substituted $C_{1-6}$ alkylene group or an optionally substituted $C_{2-6}$ alkenylene group, and other symbols are each as defined above.

In production method 1-3, compound (Ib) is obtained by using about 1.0 to 10.0 mol, preferably about 1.0 to 5.0 mol, of compound (6), and about 1.0 to 10.0 mol, preferably about 1.0 to 5.0 mol, of a base, per 1 mol of compound (4).

Examples of the base include inorganic salts such as potassium hydride, sodium hydride, potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene, and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is room temperature to 250° C., preferably 50° C. to 200° C. This reaction may be performed in a microwave reactor. In this case, the reaction time is generally 5 min to 24 hr, preferably 30 min to 2 hr. The reaction temperature is generally room temperature to 250° C., preferably 50° C. to 200° C.

The obtained compound (Ib) can be used directly as a reaction mixture, or as a crude product, for the next reaction.

It can also be isolated from the reaction mixture according to a conventional method, and can be easily purified by a separation means such as washing, recrystallization, distillation, chromatography and the like.

Compound (6) may be a commercially available reagent or can be produced according to a method known per se.

Compound (1d) which is compound (1) wherein $Ar^2$ is a substituted hydroxy group, a substituted mercapto group or a substituted amino group can be produced by, as another method, for example, alkylation reaction of compound (Ic) shown in the following production method 1-4.

[Production Method 1-4]

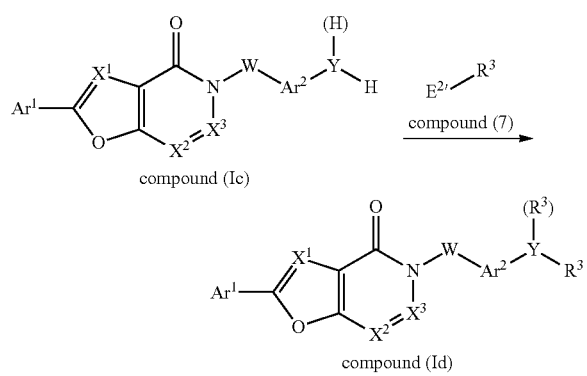

wherein Y is an oxygen atom, a sulfur atom or a nitrogen atom, $E^{2'}$ is a leaving group (e.g., a halogen atom such as chlorine, bromine, iodine and the like, substituted sulfonic acid ester such as methanesulfonic acid ester, p-toluenesulfonic acid ester and the like, and the like), or a hydroxy group, $R^3$ is a substituent, and other symbols are each as defined above. As the substituent for $R^3$, a substituent that affords a substituted hydroxy group, a substituted mercapto group or a substituted amino group for —Y($R^3$)$R^3$ can be mentioned.

When Y is an oxygen atom, a sulfur atom or a nitrogen atom, and $E^{2'}$ is a leaving group, in production method 1-4, compound (Id) is obtained by using about 1.0 to 10.0 mol, preferably about 1.0 to 5.0 mol, of compound (7), and about 1.0 to 10.0 mol, preferably about 1.0 to 5.0 mol, of a base, per 1 mol of compound (Ic).

Examples of the base include inorganic salts such as potassium hydride, sodium hydride, potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene, and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is room temperature to 250° C., preferably 50° C. to 200° C. This reaction may be performed in a microwave reactor. In this case, the reaction time is generally 5 min to 24 hr, preferably 30 min to 2 hr. The reaction temperature is generally room temperature to 250° C., preferably 50° C. to 200° C.

The obtained compound (Id) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (7), a commercially available reagent can be used, or it can be produced by a method known per se.

When Y is an oxygen atom, and $E^{2'}$ is a hydroxyl group, compound (Id) can be produced by the "Mitsunobu reaction" [for example, Synthesis, 1-27, (1981)].

The "Mitsunobu reaction" can be performed using, for example, about 0.5 to 10 mol, preferably about 1 to 2 mol, of compound (7), about 1 to 20 mol, preferably about 1 to 3 mol, of azodicarboxylic acid amide or azodicarboxylate, and about 1-20 mol, preferably about 1 to 3 mol, of trialkylphosphine or triarylphosphine, per 1 mol of compound (Ic).

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

As the "azodicarboxylic acid amide or azodicarboxylate", diisopropyl azodicarboxylate, diethyl azodicarboxylate, 1,1'-(azodicarbonyl)dipiperidine and the like are used.

As the "trialkylphosphine or triarylphosphine", triphenylphosphine, tributylphosphine and the like are used.

The reaction time is generally 30 min to 1 week, preferably 3 hr to 24 hr. The reaction temperature is generally −20° C. to 100° C., preferably 0° C. to 80° C.

The obtained compound (Id) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (7), a commercially available reagent can be used, or it can be produced by a method known per se.

Compound (If) which is compound (I) wherein $Ar^2$ is a cyano group, an optionally substituted hydrocarbon group or an optionally substituted nonaromatic heterocyclic group can be produced, as another method, for example, from compound (Ie) shown in the following production method 1-5.

[Production Method 1-5]

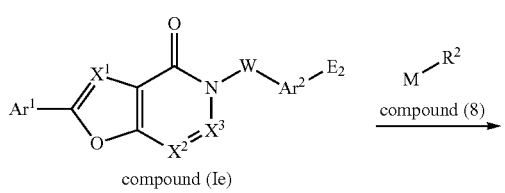

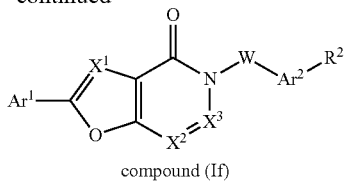

compound (If)

wherein $R^2$ is a cyano group, an optionally substituted hydrocarbon group or an optionally substituted nonaromatic heterocyclic group, and other symbols are each as defined above.

In production method 1-5, compound (If) is obtained using about 1.0 to 10.0 mol, preferably about 1.0 to 5.0 mol, of compound (8), about 1.0 to 10.0 mol, preferably about 1.0 to 5.0 mol, of a base, and about 0.000001 to 5 mol, preferably about 0.0001 to 2 mol, of a metal catalyst, per 1 mol of compound (Ie).

Examples of the base include inorganic salts such as potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

Examples of the metal catalyst include copper and a salt thereof (e.g., copper(II) acetate, copper(II) iodide and the like), palladium compounds (e.g., palladium acetate, palladium chloride, tetrakis(triphenylphosphine)palladium, dichlorobis(triphenylphosphine) palladium, [1,1'-bis(diphenylphosphino) ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, palladium compounds are preferable.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is from room temperature to 250° C., preferably 50° C. to 200° C. This reaction may be performed in a microwave reactor, for which the reaction time is generally 5 min to 24 hr, preferably 30 min to 2 hr. The reaction temperature is generally room temperature to 250° C., preferably 50° C. to 200° C.

In addition, this reaction may be performed using a ligand. As the ligand, organic amine compounds such as N,N'-dimethylethylenediamine, N,N'-dimethylcyclohexane-1,2-diamine, 2,2-bipyridyl and the like; organic phosphorus compounds such as triphenylphosphine, tri-tert-butylphosphine, tricyclohexylphosphine, BINAP (2,2'-bis(diphenylphosphino)-1,1'-binaphthyl) and the like can be mentioned. The amount of the ligand to be used is generally about 1.0 to 10.0 mol, preferably about 1.0 to 5.0 mol, per 1 mol of the metal catalyst.

The obtained compound (If) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (8), a commercially available reagent can be used, or it can be produced by a method known per se.

Compound (Ig) which is compound (I) wherein $X^2$ and $X^3$ are CH can be produced, as another method, for example, from compound (9) shown in the following production method 1-6.

[Production Method 1-6]

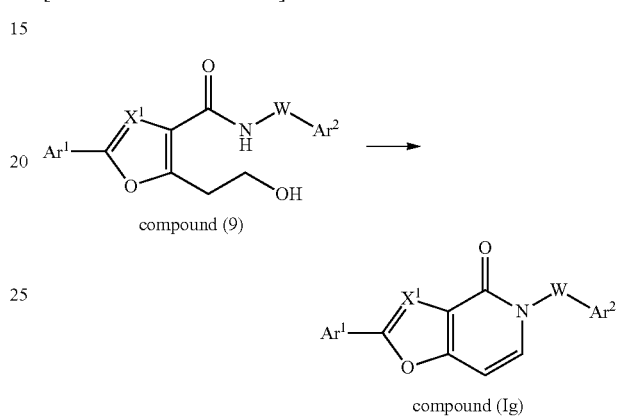

compound (9)

compound (Ig)

wherein each symbol is as defined above.

In production method 1-6, compound (Ig) is obtained by using about 1.0 to 10.0 mol, preferably 1.0 to 5.0 mol, of an oxidizing agent per 1 mol of compound (9).

Examples of the oxidizing agent include 1,1,1-triacetoxy-1,1-dihydro-1,2-benziodoxol-3-(1H)-one (Dess-Martin reagent), 2-iodoxybenzoic acid, sulfur trioxide, pyridinium chlorochromate and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; organic acids such as acetic acid, trifluoroacetic acid and the like, and the like. Two or more kinds of these solvents may be mixed and used at an appropriate ratio.

The reaction time is generally 15 min to 60 hr, preferably 30 min to 24 hr. The reaction temperature is 0° C. to 250° C., preferably room temperature to 100° C.

The obtained compound (Ig) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (9) can be produced according to the method described in the following production method or a method analogous thereto, or a method known per se.

Compound (2) which is a starting compound in production method 1-1 and compound (4) which is a starting compound in production methods 1-2 and 1-3 can be produced, for example, from compound (10) shown in the following production method 2-1.
[Production Method 2-1]

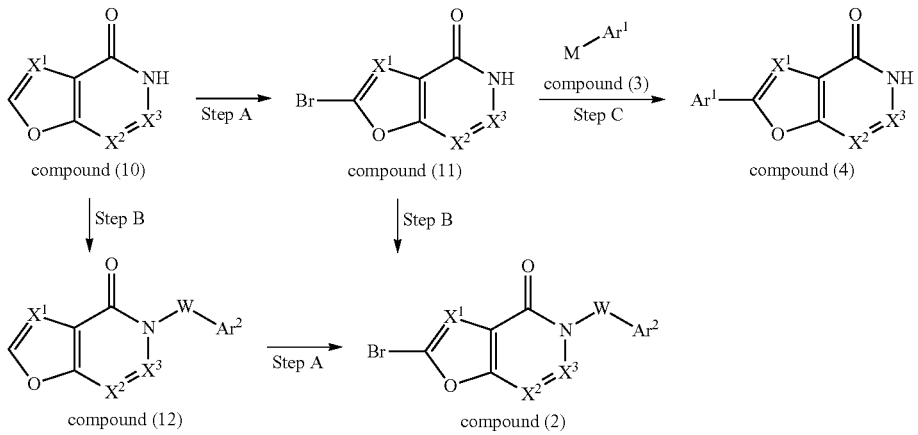

wherein each symbol is as defined above.
<Step A>

In step A, compound (11) or (2) is obtained by brominating compound (10) or (12) with 1.0 to 5.0 mol, preferably 1.0 to 2.0 mol, of a brominating reagent per 1 mol of compound (10) or (12).

Examples of the brominating reagent include bromine, hydrogen bromide, N-bromosuccinimide and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; amides such as N,N-dimethylformamide and the like; sulfoxides such as dimethyl sulfoxide and the like; organic acids such as acetic acid, trifluoroacetic acid and the like, and the like. Two or more kinds of these solvents may be mixed and used at an appropriate ratio.

The reaction time is generally 1 hr to 60 hr, preferably 1 hr to 24 hr. The reaction temperature is generally −50° C. to 150° C., preferably 0° C. to 100° C.

The obtained compound (11) and compound (2) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (10) may be a commercially available reagent, or can be produced according to the method described in the following production method or a method analogous thereto, or a method known per se.
<Step B>

In step B, compound (12) is obtained from compound (10) or compound (2) is obtained from compound (11) by a reaction according to the method described in the above-mentioned production method 1-2 or 1-3 or a method analogous thereto.
<Step C>

In step C, compound (4) is obtained from compound (11) by a reaction according to the method described in the above-mentioned production method 1-1 or a method analogous thereto.

Compound (4a) which is compound (4) wherein $X^2$ and $X^3$ are each CH, which is a starting compound in production method 1-2 and production method 1-3, and compound (11a) which is compound (11) wherein $X^2$ and $X^3$ are each CH, which is an intermediate compound in production method 2-1, can be produced, as another method, for example, from compound (13) shown in the following production method 2-2. Furthermore, compound (10a) which is compound (10) wherein $X^2$ and $X^3$ are each CH, which is a starting compound in production method 2-1, can also be produced in the same manner.
[Production Method 2-2]

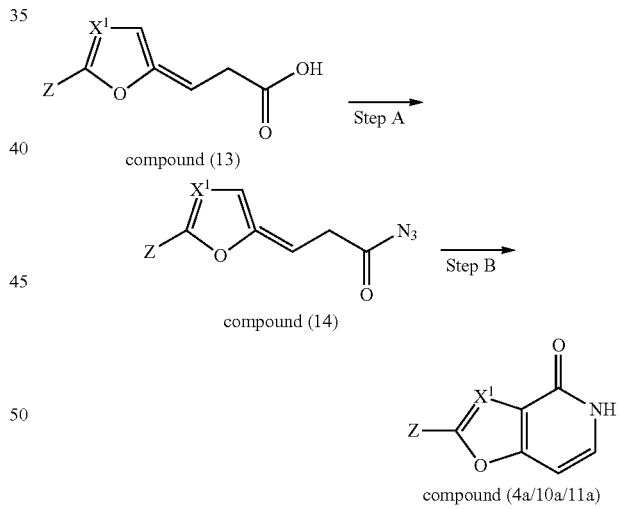

wherein Z is $Ar^1$, a bromine atom or a hydrogen atom, and other symbols are each as defined above.
<Step A>

In step A, compound (14) is obtained by reacting compound (13) with about 1.0 to 100 mol, preferably about 1.0 to 10 mol, of formic acid ester, in the presence of about 1.0 to 100 mol, preferably about 1.0 to 10 mol, of a base per 1 mol of compound (13), and using about 1.0 to 20 mol, preferably about 1.0 to 5 mol, of sodium azide.

Examples of the formic acid ester include methyl chloroformate, ethyl chloroformate, isopropyl chloroformate and the like.

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably 0° C. to 100° C.

The obtained compound (14) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (13), a commercially available reagent can be used, or it can be produced by a method known per se.
<Step B>

In step B, compound (4a/10a/11a) is obtained by using 1 mol of compound (14) and about 1.0 to 100 mol, preferably about 1.0 to 10 mol, of an organic amine compound.

Examples of the organic amine compound include tributylamine, triethylamine and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, diphenyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is room temperature to 250° C., preferably 150° C. to 250° C.

The obtained compounds (4a/10a/11a) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (4b) which is compound (4) wherein $X^1$ is $CR^1$, $X^2$ is N, and $X^3$ is CH, which is a starting compound in production method 1-2 and production method 1-3, can be produced, as another method, for example, from compound (15) shown in the following production method 2-3. Furthermore, compound (10b) which is compound (10) wherein $X^1$ is $CR^1$, $X^2$ is N, and $X^3$ is CH, which is a starting compound in production method 2-1, can also be produced in the same manner.

[Production Method 2-3]

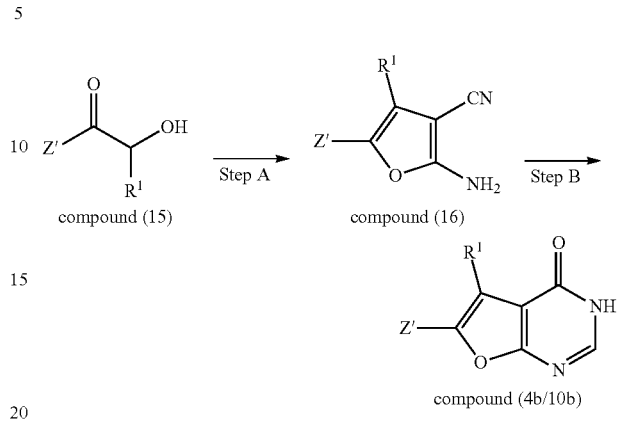

wherein Z' is $Ar^1$ or a hydrogen atom, and other symbols are each as defined above.

<Step A>

Step A is performed by a method known per se, for example, the method described in US2009/0318475 and the like, or a method analogous thereto. That is, compound (16) is obtained by cyclizing 1 mol of compound (15) by using about 1.0 to 100 mol, preferably about 1.0 to 10 mol, of malononitrile and about 1.0 to 100 mol, preferably about 1.0 to 10 mol, of a base.

Examples of the base include amines such as methylamine, ethylamine, diisopropylamine, triethylamine, N,N-dimethylaniline, 1,8-diazabicyclo[5.4.0]undec-7-ene, and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, diphenyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 15 min to 60 hr, preferably 1 hr to 24 hr. The reaction temperature is 0° C. to 250° C., preferably room temperature to 250° C.

The obtained compound (16) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (15), a commercially available reagent can be used, or it can be produced by a method known per se.
<Step B>

Step B is performed by a method known per se, for example, the method described in US2009/0318475 and the like, or a method analogous thereto. That is, compound (4b/10b) is obtained by cyclizing 1 mol of compound (16) with about 1.0 to 100 mol, preferably about 1.0 to 10 mol, of formic acid, and about 1.0 to 100 mol, preferably about 1.0 to 10 mol, of acid anhydride.

Examples of acid anhydride include acetic anhydride, trifluoroacetic anhydride and the like. In addition, these acid anhydrides may be used as solvents.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, diphenyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 15 min to 60 hr, preferably 1 hr to 24 hr. The reaction temperature is 0° C. to 250° C., preferably room temperature to 250° C.

The obtained compounds (4b/10b) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (4c) which is compound (4) wherein $X^1$ is $CR^1$, $X^2$ is CH and $X^3$ is N, which is a starting compound in production method 1-2, can be produced, as another method, for example, from compound (17) shown in the following production method 2-4. Furthermore, compound (10c) which is compound (10) wherein $X^1$ is $CR^1$, $X^2$ is CH and $X^3$ is N, which is a starting compound in production method 2-1, can also be produced in the same manner.

[Production Method 2-4]

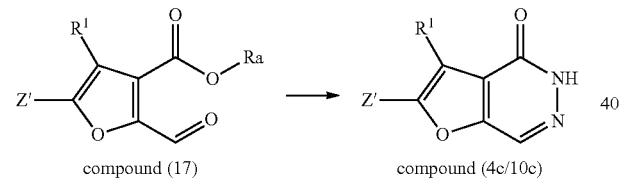

compound (17)    compound (4c/10c)

wherein Ra is a $C_{1-6}$ alkyl group, Z' is $Ar^1$ or a hydrogen atom, and other symbols are each as defined above.

In production method 2-4, compound (4c/10c) is obtained by reacting compound (17) (1 mol) with about 1.0 to 10.0 mol, preferably about 1.0 to 5.0 mol, of hydrazine or a hydrate thereof in the presence of an acid. The amount of the acid to be used is about 0.01 to 100 mol, preferably about 0.1 to 50 mol, relative to 1 mol of compound (17).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide, and the like, and the like. In addition, these acids may also be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide and the like, and the like. Two or more kinds of these solvents may be mixed and used at an appropriate ratio.

The reaction time is generally 15 min to 60 hr, preferably 15 min to 24 hr. The reaction temperature is 0° C. to 250° C., preferably room temperature to 250° C. This reaction may be performed in a microwave reactor. In this case, the reaction time is generally 5 min to 24 hr, preferably 30 min to 2 hr. The reaction temperature is generally room temperature to 250° C., preferably 50° C. to 200° C.

The obtained compounds (4c/10c) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (17), a commercially available reagent can be used, or it can be produced by a method known per se.

Compound (9), which is a starting compound in production method 1-6, can be produced from compound (18) via compound (19), compound (20) and compound (21), shown in the following production method 2-5.

[Production Method 2-5]

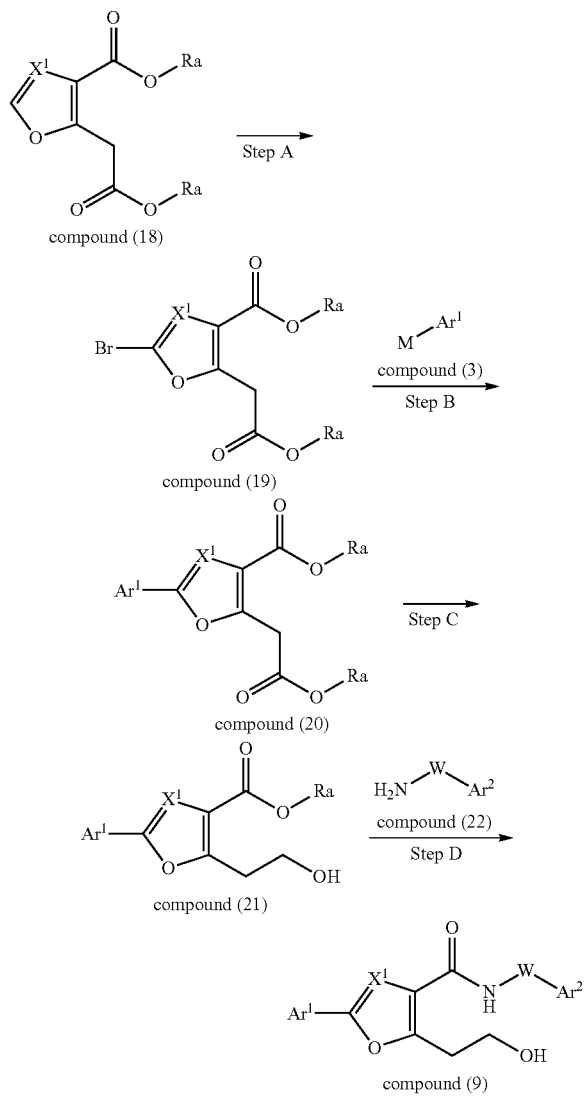

wherein each symbol is as defined above.

<Step A>

In step A, compound (19) is obtained from compound (18) by a reaction according to the method of production method 2-1, step A, or a method analogous thereto.

As compound (18), a commercially available reagent can be used, or it can be produced by a method known per se.

<Step B>

In step B, compound (20) is obtained from compound (19) by a reaction according to the method of production method 1-1, or a method analogous thereto.

<Step C>

In step C, compound (21) is obtained by using about 1.0 to 100 mol, preferably 1.0 to 10 mol, of a reducing agent per 1 mol of compound (20).

Examples of the reducing agent include sodium borohydride, lithium borohydride, diisobutylaluminum hydride, sodium bis(2-methoxyethoxy)aluminum hydride and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, diphenyl ether and the like; alcohols such as methanol, ethanol, isopropanol and the like; halogenated hydrocarbons such as chloroform, dichloromethane and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 15 min to 60 hr, preferably 30 min to 24 hr. The reaction temperature is −78° C. to 250° C., preferably 0° C. to 100° C.

The obtained compound (21) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step D>

In step D, compound (9) is obtained by treating compound (22) with trimethylaluminum, and then reacting same with compound (21). The amount of the reagents to be used is about 1.0 to 10.00 mol, preferably about 1.0 to 5.0 mol, of compound (22) and about 1.0 to 10.0 mol, preferably about 1.0 to 5.0 mol, of trimethylaluminum, per 1 mol of compound (21).

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane, and the like, and the like. Two or more kinds of these solvents may be mixed and used at an appropriate ratio.

The reaction time is generally 15 min to 60 hr, preferably 30 min to 24 hr. The reaction temperature is 0° C. to 250° C., preferably room temperature to 100° C. This reaction may be performed in a microwave reactor. In this case, the reaction time is generally 5 min to 24 hr, preferably 30 min to 2 hr. The reaction temperature is generally room temperature to 250° C., preferably 50° C. to 200° C.

The obtained compound (9) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (22), a commercially available reagent can be used, or it can be produced by a method known per se.

Compound (5a) which is compound (5) (starting compound in production method 1-2), wherein $Ar^2$ is a substituted hydroxy group, a substituted mercapto group or a substituted amino group, can be produced by, as another method, for example, alkylation reaction of compound (23) shown in the following production method 3-1.

[Production Method 3-1]

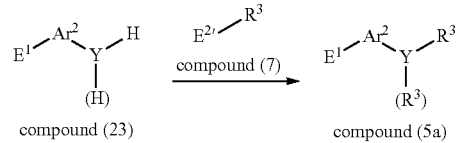

wherein each symbol is as defined above.

In production method 3-1, compound (5a) is obtained from compound (23) by a reaction according to the method described in the above-mentioned production method 1-4 or a method analogous thereto.

Compound (23) may be a commercially available reagent, or can be produced by a method known per se.

In each reaction of the aforementioned schemes, when a starting compound has hydroxy, amino (including —NH—, —NH$_2$), carboxy, carbonyl or mercapto as a substituent, a protecting group generally used in the peptide chemistry and the like may be introduced into these groups. By removing the protecting group as necessary after the reaction, the objective compound can be obtained.

Examples of the hydroxyl-protecting group include $C_{1-6}$ alkyl (e.g., methyl, ethyl, propyl, isopropyl, butyl, tert-butyl), phenyl, trityl, $C_{7-10}$ aralkyl (e.g., benzyl), formyl, $C_{1-6}$ alkyl-carbonyl (e.g., acetyl, propionyl), benzoyl, $C_{7-10}$ aralkyl-carbonyl (e.g., benzylcarbonyl), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkyl (e.g., methyl, ethyl, propyl), $C_{1-6}$ alkoxy (e.g., methoxy, ethoxy, propoxy), nitro and the like.

Examples of the amino-protecting group include formyl, $C_{1-6}$ alkyl-carbonyl (e.g., acetyl, propionyl), $C_{1-6}$ alkoxy-carbonyl (e.g., methoxycarbonyl, ethoxycarbonyl, tert-butoxycarbonyl), benzoyl, $C_{7-10}$ aralkyl-carbonyl (e.g., benzylcarbonyl), $C_{7-14}$ aralkyloxy-carbonyl (e.g., benzyloxycarbonyl, 9-fluorenylmethoxycarbonyl), $C_{7-10}$ aralkyl (e.g., benzyl, 4-methoxybenzyl), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

Examples of the carboxy-protecting group include $C_{1-6}$ alkyl (e.g., methyl, ethyl, propyl, isopropyl, butyl, tert-butyl), $C_{7-11}$ aralkyl (e.g., benzyl), phenyl, trityl, silyl (e.g., trimethylsilyl, triethylsilyl, dimethylphenylsilyl, tert-butyldimethylsilyl, tert-butyldiethylsilyl, tert-butyldiphenylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

Examples of the carbonyl-protecting group include cyclic acetal (e.g., 1,3-dioxane), acyclic acetal (e.g., di-$C_{1-6}$ alkyl acetal) and the like.

Examples of the mercapto-protecting group include $C_{1-6}$ alkyl, phenyl, trityl, $C_{7-10}$ aralkyl (e.g., benzyl), $C_{1-6}$ alkylcarbonyl, benzoyl, $C_{7-10}$ aralkyl-carbonyl (e.g., benzylcarbonyl), $C_{1-6}$ alkoxy-carbonyl, $C_{6-14}$ aryloxy-carbonyl (e.g., phenyloxycarbonyl), $C_{7-14}$ aralkyloxy-carbonyl (e.g., benzyloxycarbonyl, 9-fluorenylmethoxycarbonyl), 2-tetrahydropyranyl, $C_{1-6}$ alkylamino-carbonyl (e.g., methylaminocarbonyl, ethylaminocarbonyl) and the like. These groups are optionally substituted by 1 to 3 substituents selected from a halogen atom, $C_{1-6}$ alkyl, $C_{1-6}$ alkoxy, nitro and the like.

The above-mentioned protecting groups can be removed by a method known per se, for example, the method described in Protective Groups in Organic Synthesis, John Wiley & Sons, Inc. (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) and the like, a reduction method and the like are used.

As compound (I) and a prodrug thereof (hereinafter abbreviated as the compound of the present invention) has a superior MCH receptor (particularly, MCH receptor 1) antagonistic action, it is useful as an agent for the prophylaxis or treatment of diseases caused by MCH.

In addition, the compound of the present invention also shows low toxicity (e.g., cardiac toxicity (e.g., hERG inhibitory activity), PLsis inducing potential, acute toxicity, chronic toxicity, genetic toxicity, reproductive toxicity, drug interaction, carcinogenicity, phototoxicity).

Moreover, the compound of the present invention is superior in oral absorbability.

Furthermore, the compound of the present invention is superior in brain transfer function.

Accordingly, the compound of the present invention is safely administered as an agent for the prophylaxis or treatment of diseases caused by MCH, and the like to mammals (e.g., rat, mouse, guinea pig, rabbit, sheep, horse, pig, cow, monkey, human).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as a drug for the prophylaxis or treatment of a lifestyle-related diseases such as diabetes (e.g., type 1 diabetes, type 2 diabetes, gestational diabetes, obese diabetes, borderline diabetes), impaired glucose tolerance (IGT), diabetic complications (e.g., diabetic retinopathy, diabetic neuropathy, diabetic nephropathy), hyperlipidemia (e.g., hypertriglyceridemia, hypercholesterolemia, high LDL-cholesterolemia, low HDL-cholesterolemia, postprandial hyperlipemia), arteriosclerosis, arthritis in knee, metabolic syndrome and the like.

Moreover, the compound of the present invention is also useful as an anorexigenic agent.

The compound of the present invention can also be concurrently used with diet therapy (e.g., diet therapy for diabetes), or an exercise therapy.

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of pigmentation due to chloasma, ephelides, sunburn and the like; and further, hyperpigmentation or hypopigmentation for cosmetic purposes.

The compound of the present invention is used as it is or as a pharmaceutical composition (in the present specification, sometimes to be abbreviated as "the medicament of the present invention") formulated as a preparation together with a pharmacologically acceptable carrier by a method known per se, for example, the method described in the Japanese Pharmacopoeia.

Examples of the pharmacologically acceptable carrier include various organic or inorganic carrier substances conventionally used as a preparation material and, for example, excipient, lubricant, binder and disintegrant for solid preparations; solvent, solubilizing agent, suspending agent, isotonic agent, buffer and soothing agent for liquid preparations and the like can be mentioned. Where necessary, additives such as preservatives, antioxidizing agents, colorants, sweetening agents, adsorbent, wetting agent and the like can be used during formulation of a preparation.

Examples of the excipient include lactose, sucrose, D-mannitol, starch, cornstarch, crystalline cellulose and light anhydrous silicic acid.

Examples of the lubricant include magnesium stearate, calcium stearate, talc and colloidal silica.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose and sodium carboxymethylcellulose.

Examples of the disintegrant include starch, carboxymethylcellulose, calcium carboxymethylcellulose, croscarmellose sodium, sodium carboxymethylstarch and low-substituted hydroxypropylcellulose (L-HPC).

Examples of the solvent include water for injection, alcohol, propylene glycol, macrogol, sesame oil and corn oil.

Examples of the solubilizing agent include polyethylene glycol, propylene glycol, D-mannitol, benzyl benzoate, ethanol, trisaminomethane, cholesterol, triethanolamine, sodium carbonate and sodium citrate.

Examples of the suspending agent include surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of the isotonic agent include glucose, D-sorbitol, sodium chloride, glycerol and D-mannitol.

Examples of the buffer include buffers such as phosphate, acetate, carbonate, citrate and the like.

Examples of the soothing agent include benzyl alcohol.

Examples of the preservative include p-hydroxybenzoates, chlorobutanol, benzyl alcohol, phenethyl alcohol, dehydroacetic acid and sorbic acid.

Examples of the antioxidizing agent include sulfite and ascorbic acid.

Examples of the colorant include water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), and natural dye (e.g., β-carotene, chlorophyll, ferric oxide red).

Examples of the sweetening agent include saccharin sodium, dipotassium glycyrrhizinate, aspartame and stevia.

Examples of the adsorbent include porous starch, calcium silicate (trade name: Florite RE), magnesium aluminometasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylene lauryl ether.

Examples of the dosage form of the medicament of the present invention include tablet (including sugar-coated tablet, film-coated tablet, sublingual tablet, orally disintegrating tablet, buccal tablet etc.), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, film (e.g., orally disintegrable film, oral mucosal patch film), injection (e.g., subcutaneous injection, intravenous injection, intramuscular injection, intraperitoneal injection, drip infusion), transdermal absorption type preparation, ointment, lotion, adhesive preparation, suppository (e.g., rectal suppository, vaginal suppository), pellet, nasal preparation, pulmonary preparation (inhalant), eye drop and the like, and they can be administered safely by oral or parenteral administration (e.g., intravenous, intramuscular, subcutaneous, intraorgan, intranasal, intradermal, ocular instillation, intracerebral, rectal, vaginal, intraperitoneal and intratumor administrations, administration to the vicinity of tumor etc. and direct administration to the lesion).

The content of the compound in the medicament of the present invention in the pharmaceutical composition is, for example, about 0.1 to 100 wt % of the entire medicament of the present invention.

The dose of the compound of the present invention is appropriately determined according to the subject of administration, administration route, disease and the like.

For example, the daily dose of the compound of the present invention for oral administration to an adult patient (body weight about 60 kg) with obesity is about 0.1 to about 500 mg, preferably about 1 to about 100 mg, more preferably about 5 to about 100 mg. This amount can be administered at once or in several portions (e.g., 1-3 times) for one day.

In an attempt to enhance the action (therapeutic effect for obesity, diabetes, depression, anxiety etc.) of the compound of the present invention and decrease the amount of the compound of the present invention to be used and the like, as well as prevent or treat complications and improve prognosis, for example, the compound of the present invention can be used in combination with a pharmaceutically active ingredient (hereinafter sometimes to be referred to as "concomitant drug") that does not adversely influence the compound of the present invention. Examples of such concomitant drug include "therapeutic agent for diabetes", "therapeutic agent for diabetic complications", "anti-obesity agent", "therapeutic agent for hypertension", "therapeutic agent for hyperlipidemia", "antiarteriosclerotic agent", "antithrombotic agent", "diuretic agent", "therapeutic agent for arthritis", "antianxiety agent", "antidepressant", "psychoneurotic agent", "sleep-inducing agent" and the like. These concomitant drugs may be low-molecular-weight compounds, or high-molecular-weight proteins, polypeptides, antibodies, vaccines or the like.

Examples of the above-mentioned "therapeutic agent for diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like.

Examples of the above-mentioned "therapeutic agent for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxyl)propyl]oxazole), the compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-noradrenaline reuptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NF-κB inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the above-mentioned "therapeutic agent for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), β blockers (e.g., metoprolol, atenolol, propranolol, carvedilol, pindolol), clonidine and the like.

Examples of the above-mentioned "therapeutic agent for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic agent" include acyl coenzyme A cholesterol acyltransferase (ACAT) inhibitors (e.g., K-604), LpPLA2 inhibitors (e.g., darapladib, rilapladib), FLAP inhibitors (e.g., AM103, AM803 and the like), 5LO inhibitors (e.g., VIA-2291), sPLA2 inhibitors (e.g., A-002), apoAI mimetic peptides (e.g., D4F), HDL preparations (e.g., CSL-111) and the like.

Examples of the above-mentioned "antithrombotic agent" include heparin (e.g., heparin sodium, heparin calcium, enoxaparin sodium, dalteparin sodium), warfarin (e.g., warfarin potassium), anti-thrombin drugs (e.g., argatroban, dabigatran), FXa inhibitors (e.g., rivaroxaban, apixaban, edoxaban, YM150, the compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic agent for arthritis" include ibuprofen and the like.

Examples of the above-mentioned "antianxiety agent" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, setiptiline), selective serotonin uptake inhibitors (e.g., fluoxetine, fluvoxamine, paroxetine, sertraline, escitalopram), serotonin-noradrenaline uptake inhibitors (e.g., milnacipran, duloxetine, venlafaxine), trazodone, mirtazapine, moclobemide and the like.

Examples of the above-mentioned "psychoneurotic agent" include typical antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing agent" include Ramelteon, GABAergic hypnotics (e.g., brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:

1) administration of a single preparation obtained by simultaneously processing the compound of the present invention and the concomitant drug,
2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

EXAMPLES

The present invention is explained in more detail in the following by referring to Examples, Experimental Examples and Preparation Examples, which are not to be construed as limitative, and can be modified without substantially departing from the scope of the present invention.

In the following Examples, the "room temperature" means generally about 1° C. to about 30° C. In addition, % means weight % unless otherwise indicated.

In the $^1$H NMR (proton nuclear magnetic resonance spectrum), the chemical shift is expressed in δ value (ppm) and the coupling constant is expressed in Hz.

In the case of a mixed solvent, the ratio is a volume ratio unless otherwise indicated. In addition, % of a solution means the number of grams in 100 mL of the solution.

The abbreviations mentioned below are used in the following Examples.

s: singlet
d: doublet
t: triplet
q: quartet
dd: double doublet
dt: double triplet
m: multiplet
br: broad
J: coupling constant
DMSO-$d_6$: dimethyl sulfoxide-$d_6$
$^1$H NMR: proton nuclear magnetic resonance
MS(ESI): mass spectrometry (electrospray ionization)
MeOH: methanol
EtOH: ethanol
IPA, iPrOH: isopropanol
AcOEt: ethyl acetate
CH$_3$CN: acetonitrile
DMSO: dimethyl sulfoxide
IPE: diisopropyl ether
THF: tetrahydrofuran
DCM: dichloromethane
DME: 1,2-dimethoxyethane
DMF: N,N-dimethylformamide
DMA: N,N-dimethylacetamide
K$_2$CO$_3$: potassium carbonate
NaHCO$_3$: sodium hydrogen carbonate
Et$_3$N: triethylamine
Na$_2$SO$_4$: sodium sulfate
MgSO$_4$: magnesium sulfate
TBAF: tetrabutylammonium fluoride
NaBH$_4$: sodium borohydride
HATU: O-(7-azabenzotriazol-1-yl)-N,N,N',N'-tetramethyluronium hexafluorophosphate
NH$_4$Cl: ammonium chloride
AcOH: acetic acid
TFA: trifluoroacetic acid
Ar: argon
N$_2$: nitrogen
MS-4A: molecular sieves 4A
Pd(Ph$_3$P)$_4$: tetrakis(triphenylphosphine)palladium(0)
DEAD: diethyl azodicarboxylate
Dess-Martin periodinane: 1,1,1-triacetoxy-1,1-dihydro-1,2-benziodoxol-3(1H)-one
HPLC: high performance liquid chromatography Example 1

6-(4-Chlorophenyl)-3-(3,4-dimethoxyphenyl)furo[2,3-d]pyrimidin-4(3H)-one

A)
6-(4-Chlorophenyl)furo[2,3-d]pyrimidin-4(3H)-one

To acetic anhydride (160 mL) was added formic acid (77 mL) at 0° C. After stirring for 30 min, 2-amino-5-(4- chlorophenyl)furan-3-carbonitrile (14.8 g) was added, and the mixture was further stirred at 80° C. for 3 hr and at 110° C. overnight. The reaction mixture was allowed to cool to room temperature, and IPE (150 mL) was added. The resulting precipitate was collected by filtration, and washed with IPE to give the title compound (7.70 g) as a brown solid.
$^1$H NMR (300 MHz, DMSO-$d_6$) δ 7.49-7.60 (3H, m), 7.83-7.93 (2H, m), 8.16 (1H, s), 12.67 (1H, brs).

B) 6-(4-Chlorophenyl)-3-(3,4-dimethoxyphenyl)furo[2,3-d]pyrimidin-4(3H)-one

A mixture of 6-(4-chlorophenyl)furo[2,3-d]pyrimidin-4(3H)-one (200 mg), (3,4-dimethoxyphenyl)boronic acid (295 mg), copper(II) acetate (295 mg), MS-4A (400 mg), triethylamine (0.20 mL), pyridine (0.40 mL) and THF (2.0 mL) was stirred at room temperature for 4 hr. The reaction mixture was diluted with ethyl acetate, filtered through celite, and concentrated. The resulting residue was purified by silica gel column chromatography (ethyl acetate/hexane) to give the title compound (40.0 mg).
$^1$H NMR (300 MHz, DMSO-$d_6$) δ 3.77 (3H, s), 3.83 (3H, s), 6.99-7.19 (3H, m), 7.57 (2H, d, J=8.7 Hz), 7.66 (1H, s), 7.92 (2H, d, J=8.7 Hz), 8.43 (1H, s).
MS (ESI+): [M+H]+ 383.1.

Example 2

2-(4-Chlorophenyl)-5-(3,4-dimethoxyphenyl)furo[3,2-c]pyridin-4(5H)-one

A mixture of 2-(4-chlorophenyl)furo[3,2-c]pyridin-4(5H)-one (200 mg), (3,4-dimethoxyphenyl)boronic acid (296 mg), copper(II) acetate (9.98 mg), MS-4A (98 mg), pyridine (0.13 mL) and DMF (4.0 mL) was stirred at room temperature for 4 hr and at 50° C. overnight. After filtration of the reaction mixture through celite, the obtained filtrate was poured into 1 N hydrochloric acid, and the mixture was extracted with ethyl acetate. The resulting organic layer was washed with saturated aqueous sodium hydrogen carbonate solution and brine, dried over magnesium sulfate and concentrated in vacuo. The resulting residue was purified by silica gel column chromatography (ethyl acetate/hexane) to give the title compound (35 mg) as a white solid.
$^1$H NMR (300 MHz, DMSO-$d_6$) δ 3.77 (3H, s), 3.82 (3H, s), 6.86 (1H, d, J=8.3 Hz), 6.95 (1H, dd, J=8.5, 2.5 Hz), 7.02-7.11 (2H, m), 7.56 (2H, d, J=8.7 Hz), 7.59-7.64 (2H, m), 7.91 (2H, d, J=8.7 Hz).
MS (ESI+): [M+H]+ 382.1.

Example 3

4-(2-(2-(4-Chlorophenyl)-4-oxofuro[3,2-c]pyridin-5(4H)-yl)ethyl)benzonitrile

The title compound was obtained in an analogous manner to Example 42 using 5-(2-(4-bromophenyl)ethyl)-2-(4-chlorophenyl)furo[3,2-c]pyridin-4(5H)-one.
MS (ESI+): [M+H]+ 375.1.

Example 4

2-(4-Chlorophenyl)-5-(4-methoxyphenyl)furo[3,2-c]pyridin-4(5H)-one

The title compound was obtained in an analogous manner to Example 2 using (4-methoxyphenyl)boronic acid.
MS (ESI+): [M+H]+ 352.1.

Example 5

1-((4-(2-(4-Chlorophenyl)-4-oxofuro[3,2-c]pyridin-5(4H)-yl)-2-methoxyphenoxy)methyl)cyclopropanecarbonitrile Thionyl chloride (0.13 mL) was added to a solution of 1-(hydroxymethyl)cyclopropanecarbonitrile (87 mg) in toluene (2.0 mL) at room temperature. The reaction mixture was stirred at 80° C. for 2 hr, and the solvent was evaporated. The resulting residue was dissolved in DMF (2.0 mL), and 2-(4-chlorophenyl)-5-(4-hydroxy-3-methoxyphenyl)furo[3,2-c]pyridin-4(5H)-one (110 mg) and potassium carbonate (165 mg) were added. The reaction mixture was stirred at 80° C. for 3 hr. To the reaction mixture was added saturated aqueous sodium hydrogen carbonate solution, and the mixture was extracted with ethyl acetate. The resulting organic layer was dried over magnesium sulfate and concentrated in vacuo. The resulting residue was purified by silica gel column chromatography (NH, ethyl acetate/hexane) and recrystallized from ethanol/2-propanol to give the title compound (56.5 mg) as a pale yellow solid.
1H NMR (400 MHz, CHLOROFORM-d): δ 1.11-1.18 (2H, m), 1.35-1.44 (2H, m), 3.88 (3H, s), 4.07 (2H, s), 6.65 (1H, d, J=7.4 Hz), 6.90 (1H, d, J=8.4 Hz), 6.98 (1H, d, J=1.8 Hz), 7.05 (1H, d, J=8.3 Hz), 7.21-7.33 (2H, m), 7.42 (2H, d, J=8.4 Hz), 7.71 (2H, d, J=8.3 Hz).
MS (ESI+): [M+H]+ 447.1.

Example 6

1-((4-(6-(4-Chlorophenyl)-4-oxofuro[2,3-d]pyrimidin-3(4H)-yl)-2-methoxyphenoxy)methyl)cyclopropanecarbonitrile A) 3-(4-((tert-Butyl(dimethyl)silyl)oxy)-3-methoxyphenyl)-6-(4-chlorophenyl)furo[2,3-d]pyrimidin-4(3H)-one A mixture of 6-(4-chlorophenyl)furo[2,3-d]pyrimidin-4(3H)-one (500 mg), (4-((tert-butyl(dimethyl)silyl)oxy)-3-methoxyphenyl)boronic acid (858 mg), copper(II) acetate (552 mg), MS-4A (1 g), triethylamine (0.50 mL), pyridine (1.0 mL) and THF (30 mL) was stirred at room temperature overnight. The reaction mixture was diluted with ethyl acetate, and filtered through NH silica gel. The obtained filtrate was concentrated in vacuo to give the title compound (625 mg) as a light brown solid.
MS (ESI+): [M+H]+ 483.2.

B) 6-(4-Chlorophenyl)-3-(4-hydroxy-3-methoxyphenyl)furo[2,3-d]pyrimidin-4(3H)-one To a solution of 3-(4-((tert-butyl(dimethyl)silyl)oxy)-3-methoxyphenyl)-6-(4-chlorophenyl)furo[2,3-d]pyrimidin-4(3H)-one (625 mg) in THF (20 mL) was added TBAF (1.0 M solution in THF, 1.6 mL), and the mixture was stirred at room temperature for 3 hr. The mixture was poured into 1 N hydrochloric acid, and extracted with a mixed solvent of ethyl acetate and THF. The resulting organic layer was washed with saturated aqueous sodium hydrogen carbonate solution, dried over magnesium sulfate, and concentrated in vacuo to give the title compound (474 mg) as a white solid.
MS (ESI+): [M+H]+ 369.0.

C) 1-((4-(6-(4-Chlorophenyl)-4-oxofuro[2,3-d]pyrimidin-3(4H)-yl)-2-methoxyphenoxy)methyl)cyclopropanecarbonitrile Thionyl chloride (0.13 mL) was added to a solution of 1-(hydroxymethyl)cyclopropanecarbonitrile (87 mg) in toluene (2.0 mL) at room temperature. The reaction mixture was stirred at 80° C. for 2 hr, and the solvent was evaporated. The resulting residue was dissolved in DMF (2.0 mL), and 6-(4-chlorophenyl)-3-(4-hydroxy-3-methoxyphenyl)furo[2,3-d]pyrimidin-4(3H)-one (110 mg) and potassium carbonate (165 mg) were added. The mixture was stirred at 80° C. for 3 hr. To the reaction mixture was added saturated aqueous sodium hydrogen carbonate solution, and the mixture was extracted with ethyl acetate. The resulting organic layer was dried over magnesium sulfate and concentrated in vacuo. The resulting residue was purified by silica gel column chromatography (NH, ethyl acetate/hexane) and recrystallized from acetonitrile to give the title compound (52.2 mg) as a pale yellow solid.

$^1$H NMR (400 MHz, CHLOROFORM-d) δ 1.16 (2H, brs), 1.43 (2H, brs), 3.90 (3H, s), 4.08 (2H, s), 6.87-7.00 (2H, m), 7.07 (1H, d, J=8.5 Hz), 7.16 (1H, s), 7.44 (2H, d, J=8.2 Hz), 7.74 (2H, d, J=8.2 Hz), 8.07 (1H, s).

MS (ESI+): [M+H]+ 448.1.

Example 7

2-(4-Chlorophenyl)-5-(4-(2-hydroxy-2-methylpropoxy)-3-methoxyphenyl)furo[3,2-c]pyridin-4(5H)-one A mixture of 2-(4-chlorophenyl)-5-(4-hydroxy-3-methoxyphenyl)furo[3,2-c]pyridin-4(5H)-one (110 mg), potassium carbonate (207 mg), isobutylene oxide (0.13 mL) and DMSO (2 mL) was stirred at 170° C. for 1 hr under microwave irradiation. The reaction mixture was purified by silica gel column chromatography (NH, ethyl acetate/hexane) and recrystallized from 2-propanol to give the title compound (82 mg) as a white solid.

$^1$H NMR (400 MHz, CHLOROFORM-d) δ 1.37 (6H, s), 2.61 (1H, s), 3.87 (5H, s), 6.64 (1H, d, J=7.5 Hz), 6.86-6.92 (1H, m), 6.95 (1H, d, J=2.0 Hz), 6.99 (1H, d, J=8.4 Hz), 7.20-7.34 (2H, m), 7.42 (2H, d, J=8.4 Hz), 7.71 (2H, d, J=8.5 Hz).

MS (ESI+): [M+H]+ 440.1.

Example 8

1-((2-Chloro-4-(2-(4-chlorophenyl)-4-oxofuro[3,2-c]pyridin-5(4H)-yl)phenoxy)methyl)cyclopropanecarbonitrile A) 1-((4-Bromo-2-chlorophenoxy)methyl)cyclopropanecarbonitrile Thionyl chloride (0.92 mL) was added to a solution of 1-(hydroxymethyl)cyclopropanecarbonitrile (0.609 g) in toluene (10 mL) at room temperature. The reaction mixture was stirred at 80° C. for 2 hr, and the solvent was evaporated. The resulting residue was dissolved in DMF (10 mL), and 4-bromo-2-chlorophenol (1.0 g) and potassium carbonate (2.0 g) were added. The mixture was stirred at 80° C. overnight. To the reaction mixture was added saturated aqueous sodium hydrogen carbonate solution, and the mixture was extracted with ethyl acetate. The resulting organic layer was dried over magnesium sulfate and concentrated in vacuo. The resulting residue was purified by silica gel column chromatography (ethyl acetate/hexane) to give the title compound (1.24 g) as a colorless oil.

$^1$H NMR (400 MHz, CHLOROFORM-d) δ 1.16-1.24 (2H, m), 1.33-1.46 (2H, m), 4.04 (2H, s), 6.81 (1H, d, J=8.7 Hz), 7.33 (1H, d, J=8.7 Hz), 7.53 (1H, s).

B) 1-((2-Chloro-4-(2-(4-chlorophenyl)-4-oxofuro[3,2-c]pyridin-5(4H)-yl)phenoxy)methyl)cyclopropanecarbonitrile A mixture of 2-(4-chlorophenyl)furo[3,2-c]pyridin-4(5H)-one (100 mg), 1-((4-bromo-2-chlorophenoxy)methyl)cyclopropanecarbonitrile (175 mg), N,N'-dimethylethylenediamine (0.065 mL), copper(I) iodide (116 mg), potassium carbonate (169 mg) and DMSO (3.0 mL) was stirred at 200° C. for 1 hr under microwave irradiation. The reaction mixture was purified by silica gel column chromatography (ethyl acetate/hexane) and recrystallized from THF/2-propanol to give the title compound (44.9 mg) as a pale yellow solid.

$^1$H NMR (400 MHz, CHLOROFORM-d) δ 1.20-1.28 (2H, m), 1.42-1.47 (2H, m), 4.12 (2H, s), 6.66 (1H, d, J=7.4 Hz), 7.03 (1H, d, J=8.7 Hz), 7.18-7.33 (3H, m), 7.42 (2H, d, J=8.4 Hz), 7.47 (1H, d, J=2.1 Hz), 7.71 (2H, d, J=8.3 Hz).

MS (ESI+): [M+H]+ 451.1.

Example 9

1-(((3-Chloro-5-(2-(4-chlorophenyl)-4-oxofuro[3,2-c]pyridin-5(4H)-yl)pyridin-2-yl)oxy)methyl)cyclopropanecarbonitrile A) 1-(((5-Bromo-3-chloropyridin-2-yl)oxy)methyl)cyclopropanecarbonitrile Sodium hydride (60% oil dispersion, 0.25 g) was added to a solution of 1-(hydroxymethyl)cyclopropanecarbonitrile (0.56 g) in THF (15 mL) at 0° C., and the mixture was stirred at 0° C. under nitrogen atmosphere for 10 min. 5-Bromo-2,3-dichloropyridine (1.0 g) and DMF (2.0 mL) were added to the reaction mixture at 0° C., and the mixture was stirred at 40° C. overnight. To the reaction mixture was added saturated aqueous sodium hydrogen carbonate solution, and the mixture was extracted with ethyl acetate. The resulting organic layer was washed with saturated aqueous sodium hydrogen carbonate solution, dried over magnesium sulfate and concentrated in vacuo. The resulting residue was purified by silica gel column chromatography (ethyl acetate/hexane) to give the title compound (1.1 g) as a white solid.

MS (ESI+): [M+H]+ 287.0.

B) 1-(((3-Chloro-5-(2-(4-chlorophenyl)-4-oxofuro[3,2-c]pyridin-5(4H)-yl)pyridin-2-yl)oxy)methyl)cyclopropanecarbonitrile The title compound was obtained in an analogous manner to step B in Example 8 using 1-(((5-bromo-3-chloropyridin-2-yl)oxy)methyl)cyclopropanecarbonitrile.

MS (ESI+): [M+H]+ 452.1.

Example 10

1-((4-(2-(4-Fluorophenyl)-4-oxofuro[3,2-c]pyridin-5 (4H)-yl)-2-methoxyphenoxy)methyl)cyclopropanecarbonitrile

A) 3-(5-Bromo-2-furyl)acryloyl azide

To a mixture of 3-(5-bromo-2-furyl)acrylic acid (41.5 g) in acetone (200 mL) were added triethylamine (23.0 g) and ethyl chloroformate (26.1 g), and the mixture was stirred at room temperature for 30 min. To the resulting reaction mixture was added a solution of sodium azide (18.7 g) in water (saturated) at 0° C. The mixture was warmed to room temperature and stirred for 5 hr. The reaction mixture was filtered, and the resulting solid was washed with water and recrystallized from DCM to give the title compound (20.7 g) as a white powder.
$^1$H NMR (400 MHz, DMSO-d$_6$) δ 6.23 (1H, d, J=15.2 Hz), 6.82 (1H, d, J=3.2 Hz), 7.13 (1H, d, J=3.6 Hz), 7.51 (1H, d, J=15.6 Hz).

B) 2-Bromofuro[3,2-c]pyridin-4(5H)-one

A solution of 3-(5-bromo-2-furyl)acryloyl azide (20.7 g) and tributylamine (16 mL) in diphenyl ether (200 mL) was stirred at 220-230° C. for 30 min under nitrogen atmosphere. The reaction mixture was cooled to room temperature, and tert-butyl methyl ether (200 mL) was added thereto. The resulting solid was collected by filtration. The collected solid was purified by silica gel column chromatography (ethyl acetate/hexane), followed by HPLC (C18, mobile phase: water/acetonitrile (including 0.1% TFA)). To the obtained fraction was added saturated aqueous sodium hydrogen carbonate solution, and the mixture was extracted with ethyl acetate. The extract was dried over anhydrous magnesium sulfate, concentrated in vacuo, and recrystallized from ethyl acetate to give the title compound (7.00 g) as a white powder.
MS (ESI+): [M+H]+ 213.8.

C) 2-Bromo-5-(4-((tert-butyl(dimethyl)silyl)oxy)-3-methoxyphenyl)furo[3,2-c]pyridin-4(5H)-one A mixture of 2-bromofuro[3,2-c]pyridin-4(5H)-one (1.64 g), (4-((tert-butyl(dimethyl)silyl)oxy)-3-methoxyphenyl)boronic acid (3.24 g), copper(II) acetate (2.09 g), MS-4A (4.0 g), triethylamine (4.0 mL), pyridine (8.0 mL) and THF (40 mL) was stirred at room temperature overnight. The reaction mixture was diluted with ethyl acetate, and filtered through celite. The obtained filtrate was concentrated in vacuo. The resulting residue was purified by silica gel column chromatography (ethyl acetate/hexane) to give the title compound (3.59 g) as a light brown solid.
MS (ESI+): [M+H]+ 450.1.

D) 2-Bromo-5-(4-hydroxy-3-methoxyphenyl)furo[3,2-c]pyridin-4(5H)-one

TBAF (1.0 M solution in THF, 9.6 mL) was added to a solution of 2-bromo-5-(4-((tert-butyl(dimethyl)silyl)oxy)-3-methoxyphenyl)furo[3,2-c]pyridin-4(5H)-one (3.59 g) in THF (50 mL) at room temperature, and the mixture was stirred at room temperature for 20 min. To the reaction mixture was added saturated aqueous ammonium chloride solution, and the mixture was extracted with ethyl acetate twice. The resulting organic layer was dried over anhydrous magnesium sulfate and concentrated in vacuo. The resulting residue was purified by silica gel column chromatography (ethyl acetate/hexane) to give the title compound (2.45 g) as a white solid.
MS (ESI+): [M+H]+ 335.9.

E) 1-((4-(2-Bromo-4-oxofuro[3,2-c]pyridin-5(4H)-yl)-2-methoxyphenoxy)methyl)cyclopropanecarbonitrile Thionyl chloride (1.6 mL) was added to a solution of 1-(hydroxymethyl)cyclopropanecarbonitrile (1.42 g) in toluene (20 mL) at room temperature. The reaction mixture was stirred at 80° C. for 2 hr, and the solvent was evaporated. The resulting residue was dissolved in DMF (20 mL), and 2-bromo-5-(4-hydroxy-3-methoxyphenyl)furo[3,2-c]pyridin-4(5H)-one (2.45 g) and potassium carbonate (4.03 g) were added. The mixture was stirred at 80° C. overnight. To the reaction mixture was added saturated aqueous ammonium chloride solution, and the mixture was extracted with ethyl acetate three times. The resulting organic layer was dried over magnesium sulfate and concentrated in vacuo, and the resulting residue was filtered through NH silica gel. The filtrate was concentrated in vacuo, and the resulting solid was washed with IPE to give the title compound (2.80 g) as a white solid.
MS (ESI+): [M+H]+ 416.1.

F) 1-((4-(2-(4-Fluorophenyl)-4-oxofuro[3,2-c]pyridin-5(4H)-yl)-2-methoxyphenoxy)methyl)cyclopropanecarbonitrile A mixture of 1-((4-(2-bromo-4-oxofuro[3,2-c]pyridin-5 (4H)-yl)-2-methoxyphenoxy)methyl)cyclopropanecarbonitrile (100 mg), (4-fluorophenyl)boronic acid (50.5 mg), Pd(Ph$_3$P)$_4$ (13.9 mg), potassium carbonate (49.9 mg), DME (1.5 mL) and water (0.30 mL) was stirred at 130° C. for 30 min under microwave irradiation. The reaction mixture was purified by silica gel column chromatography (NH, ethyl acetate/hexane) and recrystallized from 2-propanol to give the title compound (59.6 mg) as a white solid.
$^1$H NMR (400 MHz, CHLOROFORM-d) δ 1.10-1.25 (2H, m), 1.36-1.44 (2H, m), 3.88 (3H, s), 4.07 (2H, s), 6.65 (1H, d, J=7.3 Hz), 6.90 (1H, d, J=8.3 Hz), 6.98 (1H, s), 7.05 (1H, d, J=8.4 Hz), 7.10-7.21 (3H, m), 7.23-7.32 (1H, m), 7.70-7.80 (2H, m).
MS (ESI+): [M+H]+ 431.1.

Example 11

1-((4-(2-(3-Fluorophenyl)-4-oxofuro[3,2-c]pyridin-5 (4H)-yl)-2-methoxyphenoxy)methyl)cyclopropanecarbonitrile The title compound was obtained in an analogous manner to step F in Example 10 using (3-fluorophenyl)boronic acid.
MS (ESI+): [M+H]+ 431.1.

Example 12

1-((4-(2-(5-Chloro-2-thienyl)-4-oxofuro[3,2-c]pyridin-5(4H)-yl)-2-methoxyphenoxy)methyl)cyclopropanecarbonitrile A mixture of 1-((4-(2-bromo-4-oxofuro[3,2-c]pyridin-5 (4H)-yl)-2-methoxyphenoxy)methyl)cyclopropanecarbonitrile (100 mg), (5-chloro-2-thiophene)boronic acid (78.0 mg), Pd(Ph₃P)₄ (27.8 mg), potassium carbonate (49.9 mg), DME (1.5 mL) and water (0.30 mL) was stirred under microwave irradiation at 130° C. for 30 min, and at 150° C. for 30 min. The reaction mixture was purified by silica gel column chromatography (NH, ethyl acetate/hexane) and recrystallized from ethanol to give the title compound (33.1 mg) as a white solid.

$^1$H NMR (400 MHz, CHLOROFORM-d) δ 1.11-1.19 (2H, m), 1.37-1.46 (2H, m), 3.88 (3H, s), 4.07 (2H, s), 6.61 (1H, d, J=7.4 Hz), 6.88 (1H, dd, J=8.5, 2.1 Hz), 6.91 (1H, d, J=4.0 Hz), 6.96 (1H, d, J=1.9 Hz), 7.00-7.06 (2H, m), 7.17 (1H, d, J=3.9 Hz), 7.25-7.30 (1H, m).

MS (ESI+): [M+H]+ 453.0.

Example 13

1-((2-Methoxy-4-(4-oxo-2-(3-thienyl)furo[3,2-c]pyridin-5(4H)-yl) phenoxy)methyl)cyclopropanecarbonitrile The title compound was obtained in an analogous manner to step F in Example 10 using (3-thiophene)boronic acid.

MS (ESI+): [M+H]+ 419.1.

Example 14

1-((2-Methoxy-4-(4-oxo-2-(2-thienyl)furo[3,2-c]pyridin-5(4H)-yl)phenoxy)methyl)cyclopropanecarbonitrile The title compound was obtained in an analogous manner to step F in Example 10 using (2-thiophene)boronic acid.

MS (ESI+): [M+H]+ 419.1.

Example 15

1-((4-(2-(2-Fluorophenyl)-4-oxofuro[3,2-c]pyridin-5(4H)-yl)-2-methoxyphenoxy)methyl)cyclopropanecarbonitrile A mixture of 1-((4-(2-bromo-4-oxofuro[3,2-c]pyridin-5(4H)-yl)-2-methoxyphenoxy)methyl)cyclopropanecarbonitrile (100 mg), (2-fluorophenyl)boronic acid (67.4 mg), Pd(Ph₃P)₄ (13.9 mg), potassium carbonate (49.9 mg), DME (1.5 mL) and water (0.30 mL) was stirred at 130° C. for 30 min under microwave irradiation. The mixture was purified by silica gel column chromatography (NH, ethyl acetate/hexane) and the solid was recrystallized from ethanol to give the title compound (84.0 mg) as a white solid.

$^1$H NMR (400 MHz, CHLOROFORM-d) δ 1.10-1.19 (2H, m), 1.37-1.47 (2H, m), 3.88 (3H, s), 4.07 (2H, s), 6.66 (1H, d, J=7.4 Hz), 6.90 (1H, d, J=8.4 Hz), 6.99 (1H, d, J=1.9 Hz), 7.05 (1H, d, J=8.4 Hz), 7.14-7.37 (4H, m), 7.44 (1H, d, J=2.9 Hz), 7.92 (1H, t, J=7.1 Hz).

MS (ESI+): [M+H]+ 431.1.

Example 16

1-((2-Methoxy-4-(2-(4-methoxyphenyl)-4-oxofuro[3,2-c]pyridin-5(4H)-yl)phenoxy)methyl)cyclopropanecarbonitrile A mixture of 1-((4-(2-bromo-4-oxofuro[3,2-c]pyridin-5(4H)-yl)-2-methoxyphenoxy)methyl)cyclopropanecarbonitrile (100 mg), (4-methoxyphenyl)boronic acid (54.9 mg), Pd(Ph₃P)₄ (13.9 mg), potassium carbonate (49.9 mg), DME (1.5 mL) and water (0.30 mL) was stirred at 130° C. for 30 min under microwave irradiation. The mixture was purified by silica gel column chromatography (NH, ethyl acetate/hexane) and the solid was recrystallized from methanol to give the title compound (57.4 mg) as a white solid.

$^1$H NMR (400 MHz, CHLOROFORM-d) δ 1.11-1.19 (2H, m), 1.35-1.44 (2H, m), 3.86 (3H, s), 3.88 (3H, s), 4.07 (2H, s), 6.64 (1H, d, J=7.4 Hz), 6.90 (1H, d, J=8.4 Hz), 6.95-7.01 (3H, m), 7.04 (1H, d, J=8.4 Hz), 7.10 (1H, s), 7.24 (1H, d, J=7.5 Hz), 7.72 (2H, d, J=8.5 Hz).

MS (ESI+): [M+H]+ 443.1.

Example 17

1-((2-Methoxy-4-(2-(3-methoxyphenyl)-4-oxofuro[3,2-c]pyridin-5(4H)-yl)phenoxy)methyl)cyclopropanecarbonitrile The title compound was obtained in an analogous manner to step F in Example 10 using (3-methoxyphenyl)boronic acid.

MS (ESI+): [M+H]+ 443.1.

Example 18

1-((4-(2-(3,4-Difluorophenyl)-4-oxofuro[3,2-c]pyridin-5(4H)-yl)-2-methoxyphenoxy)methyl)cyclopropanecarbonitrile The title compound was obtained in an analogous manner to step F in Example 10 using (3,4-difluorophenyl)boronic acid.

MS (ESI+): [M+H]+ 449.1.

Example 19

1-((4-(2-(5-Chloropyridin-2-yl)-4-oxofuro[3,2-c]pyridin-5(4H)-yl)-2-methoxyphenoxy)methyl)cyclopropanecarbonitrile A mixture of 1-((4-(2-bromo-4-oxofuro[3,2-c]pyridin-5(4H)-yl)-2-methoxyphenoxy)methyl)cyclopropanecarbonitrile (100 mg), lithium 1-(5-chloropyridin-2-yl)-4-methyl-2,6,7-trioxa-1-borabicyclo[2.2.2]octan-1-uide (119 mg), Pd(Ph₃P)₄ (27.8 mg), copper(I) iodide (92 mg) and DMA (2.0 mL) was stirred at 200° C. for 30 min under microwave irradiation. The reaction mixture was purified by silica gel column chromatography (NH, ethyl acetate/hexane) and the solid was recrystallized from ethanol to give the title compound (71.0 mg) as a white solid.

$^1$H NMR (400 MHz, CHLOROFORM-d) δ 1.11-1.19 (2H, m), 1.36-1.43 (2H, m), 3.88 (3H, s), 4.07 (2H, s), 6.68 (1H, d, J=7.5 Hz), 6.90 (1H, d, J=8.4 Hz), 6.98 (1H, s), 7.05 (1H, d, J=8.4 Hz), 7.33 (1H, d, J=7.5 Hz), 7.59 (1H, s), 7.67-7.79 (2H, m), 8.62 (1H, s).

MS (ESI+): [M+H]+ 448.1.

Example 20

1-((2-Methoxy-4-(4-oxo-2-phenylfuro[3,2-c]pyridin-5(4H)-yl)phenoxy)methyl)cyclopropanecarbonitrile A mixture of 1-((4-(2-bromo-4-oxofuro[3,2-c]pyridin-5(4H)-yl)-2-methoxyphenoxy)methyl)cyclopropanecarbonitrile (100 mg), phenylboronic acid (44.0 mg), Pd(Ph₃P)₄ (13.9 mg), potassium carbonate (49.9 mg), DME (1.5 mL) and water (0.30 mL) was stirred at 130° C. for 30 min under microwave irradiation. The reaction mixture was purified by silica gel column chromatography (NH, ethyl acetate/hexane) and the solid was recrystallized from ethanol to give the title compound (57.4 mg) as a white solid.

$^1$H NMR (400 MHz, CHLOROFORM-d) δ 1.12-1.21 (2H, m), 1.36-1.44 (2H, m), 3.88 (3H, s), 4.07 (2H, s), 6.66 (1H, d, J=7.4 Hz), 6.90 (1H, d, J=8.5 Hz), 6.99 (1H, s), 7.05 (1H, d, J=8.4 Hz), 7.21-7.30 (2H, m), 7.32-7.39 (1H, m), 7.45 (2H, t, J=7.5 Hz), 7.79 (2H, d, J=7.5 Hz).

MS (ESI+): [M+H]+ 413.1.

Example 21

1-((4-(2-(5-Fluoropyridin-2-yl)-4-oxofuro[3,2-c]pyridin-5(4H)-yl)-2-methoxyphenoxy)methyl)cyclopropanecarbonitrile A mixture of 1-((4-(2-bromo-4-oxofuro[3,2-c]pyridin-5(4H)-yl)-2-methoxyphenoxy)methyl)cyclopropanecarbonitrile (100 mg), lithium 1-(5-fluoropyridin-2-yl)-4-methyl-2,6,7-trioxa-1-borabicyclo[2.2.2]octan-1-uide (111 mg), Pd(Ph$_3$P)$_4$ (27.8 mg), copper(I) iodide (92 mg) and DMA (2.0 mL) was stirred at 200° C. for 30 min under microwave irradiation. The reaction mixture was purified by silica gel column chromatography (NH, ethyl acetate/hexane) and the solid was recrystallized from ethanol to give the title compound (33.5 mg) as a white solid.

$^1$H NMR (400 MHz, CHLOROFORM-d) δ 1.11-1.19 (2H, m), 1.36-1.43 (2H, m), 3.88 (3H, s), 4.07 (2H, s), 6.68 (1H, d, J=7.4 Hz), 6.90 (1H, d, J=8.5 Hz), 6.98 (1H, s), 7.05 (1H, d, J=8.5 Hz), 7.32 (1H, d, J=7.4 Hz), 7.46-7.57 (2H, m), 7.79 (1H, dd, J=8.5, 4.2 Hz), 8.54 (1H, s).

MS (ESI+): [M+H]+ 432.1.

Example 22

5-(4-Bromo-3-methoxyphenyl)-2-(4-chlorophenyl)furo[3,2-c]pyridin-4(5H)-one

The title compound was obtained in an analogous manner to Example 2 using (4-bromo-3-methoxyphenyl)boronic acid.

MS (ESI+): [M+H]+ 430.0.

Example 23

1-(((5-(2-(4-Chlorophenyl)-4-oxofuro[3,2-c]pyridin-5(4H)-yl)-3-methoxypyridin-2-yl)oxy)methyl)cyclopropanecarbonitrile A) 5-Bromo-2-chloropyridin-3-ol An aqueous sodium hypochlorite solution (5% chlorine, 43 mL) was added to a solution of 5-bromopyridin-3-ol (5.0 g) and sodium hydroxide (1.3 g) in water (50 mL) at room temperature, and the mixture was stirred overnight. After addition of an additional aqueous sodium hypochlorite solution (5% chlorine, 10 mL), the mixture was stirred at room temperature for 3 hr. The reaction mixture was neutralized with acetic acid, and the resulting precipitate was collected by filtration to give the title compound (4.54 g) as a light brown solid, which included 5-bromo-2,4-dichloropyridin-3-ol as a byproduct. The solid was subjected to the next reaction without further purification.

$^1$H NMR (400 MHz, CHLOROFORM-d) δ 7.49 (1H, s), 8.06 (1H, s).

B) 5-Bromo-2-chloro-3-methoxypyridine

Potassium carbonate (1.0 g) was added to a mixture of 5-bromo-2-chloropyridin-3-ol (1.0 g), iodomethane (0.45 mL), THF (20 mL) and DMF (5.0 mL) at room temperature, and the mixture was stirred overnight. To the reaction mixture was added brine, and the mixture was extracted with ethyl acetate twice. The resulting organic layer was washed with brine, dried over magnesium sulfate and concentrated in vacuo. The resulting residue was purified by silica gel column chromatography (ethyl acetate/hexane) to give the title compound (0.80 g) as a pale yellow solid, which included 5-bromo-2,4-dichloro-3-methoxypyridine as a byproduct. The solid was subjected to the next reaction without further purification.

$^1$H NMR (400 MHz, CHLOROFORM-d) δ 3.93 (3H, s), 7.33 (1H, s), 8.07 (1H, s).

C) 1-(((5-Bromo-3-methoxypyridin-2-yl)oxy)methyl)cyclopropanecarbonitrile

Sodium hydride (60% oil dispersion, 76 mg) was added to a solution of 1-(hydroxymethyl)cyclopropanecarbonitrile (170 mg) in THF (5 mL) at 0° C., and the mixture was stirred under nitrogen atmosphere for 10 min. A solution of 5-bromo-2-chloro-3-methoxypyridine (300 mg) in DMF (1.0 mL) was added to the mixture at 0° C. The resulting mixture was stirred at 40° C. under nitrogen atmosphere overnight. To the reaction mixture was added brine, and the mixture was extracted with ethyl acetate. The resulting organic layer was washed with brine, dried over magnesium sulfate and concentrated in vacuo. The resulting residue was purified by silica gel column chromatography (ethyl acetate/hexane) to give the title compound (155 mg) as a white solid, which included 1-(((5-bromo-4-chloro-3-methoxypyridin-2-yl)oxy)methyl)cyclopropanecarbonitrile as a byproduct. The solid was subjected to the next reaction without further purification.

$^1$H NMR (400 MHz, CHLOROFORM-d) δ 1.14-1.23 (2H, m), 1.36-1.45 (2H, m), 3.88 (3H, s), 4.35 (2H, s), 7.18 (1H, s), 7.72 (1H, s).

D) 1-(((5-(2-(4-Chlorophenyl)-4-oxofuro[3,2-c]pyridin-5(4H)-yl)-3-methoxypyridin-2-yl)oxy)methyl)cyclopropanecarbonitrile A mixture of 2-(4-chlorophenyl)furo[3,2-c]pyridin-4(5H)-one (100 mg), 1-(((5-bromo-3-methoxypyridin-2-yl)oxy)methyl)cyclopropanecarbonitrile (155 mg), N,N'-dimethylethylenediamine (0.043 mL), copper(I) iodide (78 mg), potassium carbonate (113 mg) and DMSO (3 mL) was stirred at 190° C. for 1 hr under microwave irradiation. The reaction mixture was purified by silica gel column chromatography (NH, ethyl acetate/hexane) and the resulting solid was recrystallized from ethanol to give the title compound (12.60 mg) as a pale yellow solid.

$^1$H NMR (400 MHz, CHLOROFORM-d) δ 1.15-1.24 (2H, m), 1.39-1.45 (2H, m), 3.91 (3H, s), 4.46 (2H, s), 6.69 (1H, d, J=7.3 Hz), 7.24-7.30 (3H, m), 7.43 (2H, d, J=8.4 Hz), 7.66-7.75 (3H, m).

MS (ESI+): [M+H]+ 448.1.

Example 24

Methyl 4-(2-(4-chlorophenyl)-4-oxofuro[3,2-c]pyridin-5(4H)-yl)-2-methoxybenzoate A mixture of 2-(4-chlorophenyl)furo[3,2-c]pyridin-4(5H)-one (1.8 g), (3-methoxy-4-(methoxycarbonyl)phenyl)boronic acid (2.0 g), copper(II) acetate (1.7 g), MS-4A (1.0 g), triethylamine (3.0 mL), pyridine (6.0 mL) and THF (30 mL) was stirred at room temperature overnight. The reaction mixture was diluted with ethyl acetate, and filtered through celite. The filtrate was concentrated and purified by silica gel column chromatography (NH, ethyl acetate/hexane) to give the title compound (0.078 g) as a light brown solid.

$^1$H NMR (400 MHz, CHLOROFORM-d) δ 3.92 (3H, s), 3.94 (3H, s), 6.69 (1H, d, J=7.4 Hz), 7.01 (1H, dd, J=8.2, 1.7 Hz), 7.10 (1H, d, J=1.4 Hz), 7.22-7.30 (2H, m), 7.43 (2H, d, J=8.5 Hz), 7.72 (2H, d, J=8.5 Hz), 7.94 (1H, d, J=8.2 Hz).

MS (ESI+): [M+H]+ 410.0.

Example 25

2-(4-Chlorophenyl)-5-(4-ethyl-3-methoxyphenyl)furo[3,2-c]pyridin-4(5H)-one

Ethylmagnesium bromide (1 M solution in THF, 0.93 mL) was added to a solution of 5-(4-bromo-3-methoxyphenyl)-2-(4-chlorophenyl)furo[3,2-c]pyridin-4(5H)-one (100 mg) and (bis(diphenylphosphino) ferrocene)dichloropalladium (II) (dichloromethane complex, 9.48 mg) in THF (3.0 mL) at room temperature. The mixture was stirred at 50° C. under nitrogen atmosphere for 3 hr. To the reaction mixture was added saturated aqueous ammonium chloride solution, and the mixture was extracted with ethyl acetate. The resulting organic layer was washed with brine, dried over magnesium sulfate and concentrated in vacuo. The resulting residue was purified by silica gel column chromatography (NH, ethyl acetate/hexane) and the solid was recrystallized from ethanol to give the title compound (10.8 mg) as a light brown solid.

MS (ESI+): [M+H]+ 380.1.

Example 26

2-(4-Chlorophenyl)-5-(4-hydroxyphenyl)furo[3,2-c]pyridin-4(5H)-one

A) 5-(4-((tert-Butyl(dimethyl)silyl)oxy)phenyl)-2-(4-chlorophenyl)furo[3,2-c]pyridin-4(5H)-one The title compound was obtained in an analogous manner to Example 2 using (4-((tert-butyl(dimethyl) silyl)oxy)phenyl) boronic acid.

MS (ESI+): [M+H]+ 452.1.

B) 2-(4-Chlorophenyl)-5-(4-hydroxyphenyl)furo[3,2-c]pyridin-4(5H)-one

The title compound was obtained in an analogous manner to step B in Example 6 using 5-(4-((tert-butyl(dimethyl)silyl)oxy)phenyl)-2-(4-chlorophenyl)furo[3,2-c]pyridin-4(5H)-one.

MS (ESI+): [M+H]+ 338.0.

Example 27

1-((2-Methoxy-4-(4-oxo-2-(4-(trifluoromethyl)phenyl)furo[3,2-c]pyridin-5(4H)-yl)phenoxy)methyl)cyclopropanecarbonitrile A mixture of 1-((4-(2-bromo-4-oxofuro[3,2-c]pyridin-5(4H)-yl)-2-methoxyphenoxy)methyl)cyclopropanecarbonitrile (100 mg), (4-trifluoromethylphenyl)boronic acid (68.6 mg), tetrakis(triphenylphosphine)palladium (13.9 mg), potassium carbonate (49.9 mg), DME (1.5 mL) and water (0.30 mL) was heated at 130° C. for 30 min under microwave irradiation. The resulting mixture was purified by silica gel column chromatography (NH, ethyl acetate/hexane) and the solid was recrystallized from ethanol to give the title compound (91.9 mg) as a white solid.

$^1$H NMR (400 MHz, CHLOROFORM-d) δ 1.11-1.20 (2H, m), 1.37-1.45 (2H, m), 3.89 (3H, s), 4.07 (2H, s), 6.67 (1H, d, J=7.3 Hz), 6.88-6.94 (1H, m), 6.98 (1H, d, J=1.9 Hz), 7.05 (1H, d, J=8.4 Hz), 7.32 (1H, d, J=7.5 Hz), 7.36 (1H, s), 7.70 (2H, d, J=8.2 Hz), 7.89 (2H, d, J=8.0 Hz).

MS (ESI+): [M+H]+ 481.1.

Example 28

1-((2-Methoxy-4-(4-oxo-2-(4-(trifluoromethoxy)phenyl)furo[3,2-c]pyridin-5(4H)-yl)phenoxy)methyl)cyclopropanecarbonitrile A mixture of 1-((4-(2-bromo-4-oxofuro[3,2-c]pyridin-5(4H)-yl)-2-methoxyphenoxy)methyl)cyclopropanecarbonitrile (100 mg), (4-(trifluoromethoxy)phenyl)boronic acid (74.4 mg), tetrakis(triphenylphosphine)palladium (13.9 mg), potassium carbonate (49.9 mg), DME (1.5 mL) and water (0.30 mL) was heated at 130° C. for 30 min under microwave irradiation. The resulting mixture was purified by silica gel column chromatography (NH, ethyl acetate/hexane) and the solid was recrystallized from ethanol to give the title compound (90.4 mg) as a white solid.

$^1$H NMR (400 MHz, CHLOROFORM-d) δ 1.09-1.20 (2H, m), 1.38-1.44 (2H, m), 3.88 (3H, s), 4.07 (2H, s), 6.66 (1H, d, J=7.3 Hz), 6.90 (1H, dd, J=8.4, 2.3 Hz), 6.98 (1H, d, J=2.0 Hz), 7.05 (1H, d, J=8.4 Hz), 7.25 (1H, s), 7.30 (3H, d, J=7.4 Hz), 7.81 (2H, d, J=8.7 Hz).

MS (ESI+): [M+H]+ 497.2.

Example 29

2-(4-Chlorophenyl)-5-(4-cyclopentyl-3-methoxyphenyl)furo[3,2-c]pyridin-4(5H)-one Cyclopentylmagnesium bromide (1 M solution in THF, 1.4 mL) was added to a solution of zinc chloride (190 mg) in THF (4.0 mL) at room temperature, and then 5-(4-bromo-3-methoxyphenyl)-2-(4-chlorophenyl)furo[3,2-c]pyridin-4(5H)-one (100 mg) and (bis(diphenylphosphino)ferrocene)dichloropalladium(II) (dichloromethane complex, 9.48 mg) were added. The resulting mixture was stirred at 50° C. under nitrogen atmosphere for 1 hr. To the resulting mixture was added saturated aqueous ammonium chloride solution, and the mixture was extracted with ethyl acetate. The resulting organic layer was washed with brine, dried over magnesium sulfate, filtered through silica gel pad and concentrated in vacuo. The resulting residue was purified by HPLC (C18, mobile phase: water/acetonitrile (including 0.1% TFA)). To the obtained fraction was added saturated aqueous sodium hydrogen carbonate solution, and the mixture was extracted with ethyl acetate. The extract was dried over anhydrous magnesium sulfate and concentrated in vacuo, and the solid was recrystallized from ethanol to give the title compound (20.3 mg) as a light brown solid.

MS (ESI+): [M+H]+ 420.1.

Example 30

2-(4-Chlorophenyl)-5-(4-hydroxy-3-methoxyphenyl)furo[3,2-c]pyridin-4(5H)-one

A) 5-(4-((tert-Butyl(dimethyl)silyl)oxy)-3-methoxyphenyl)-2-(4-chlorophenyl)furo[3,2-c]pyridin-4(5H)-one A mixture of 2-(4-chlorophenyl)furo[3,2-c]pyridin-4(5H)-one (500 mg), (4-((tert-butyl(dimethyl)silyl)oxy)-3- methoxyphenyl)boronic acid (862 mg), copper(II) acetate (555 mg), MS-4A (1.0 g), triethylamine (0.50 mL), pyridine (1.0 mL) and THF (30 mL) was stirred at room temperature overnight. The resulting mixture was diluted with ethyl acetate, and filtered through NH silica gel pad. The filtrate was concentrated and purified by silica gel column chromatography (NH, ethyl acetate/hexane) to give the title compound (409 mg) as a white solid.

MS (ESI+): [M+H]+ 482.2.

B) 2-(4-Chlorophenyl)-5-(4-hydroxy-3-methoxyphenyl)furo[3,2-c]pyridin-4(5H)-one To a solution of 5-(4-((tert-butyl(dimethyl)silyl)oxy)-3-methoxyphenyl)-2-(4-chlorophenyl)furo[3,2-c]pyridin-4 (5H)-one (408 mg) in THF (10 mL) was added TBAF (1.0 M solution in THF, 1.0 mL), and the mixture was stirred at room temperature for 3 hr. The resulting mixture was poured into 1 N hydrochloric acid, and extracted with ethyl acetate/THF. The resulting organic layer was washed with brine, dried over magnesium sulfate and concentrated in vacuo to give the title compound (305 mg) as a white solid.

$^1$H NMR (400 MHz, CHLOROFORM-d) δ 3.92 (3H, s), 5.78 (1H, s), 6.63 (1H, d, J=7.4 Hz), 6.85 (1H, dd, J=8.3, 2.1 Hz), 6.95 (1H, d, J=2.0 Hz), 7.01 (1H, d, J=8.4 Hz), 7.21-7.31 (2H, m), 7.42 (2H, d, J=8.5 Hz), 7.71 (2H, d, J=8.5 Hz).

MS (ESI+): [M+H]+ 368.1.

Example 31

2-(4-Chlorophenyl)-5-(3-hydroxyphenyl)furo[3,2-c]pyridin-4(5H)-one

A) 5-(3-((tert-Butyl(dimethyl)silyl)oxy)phenyl)-2-(4-chlorophenyl)furo[3,2-c]pyridin-4(5H)-one The title compound was obtained in an analogous manner to Example 2 using (3-((tert-butyl(dimethyl) silyl)oxy)phenyl)boronic acid.

MS (ESI+): [M+H]+ 452.1.

B) 2-(4-Chlorophenyl)-5-(3-hydroxyphenyl)furo[3,2-c]pyridin-4 (5H)-one

The title compound was obtained in an analogous manner to step B in Example 6 using 5-(3-((tert-butyl(dimethyl)silyl)oxy)phenyl)-2-(4-chlorophenyl)furo[3,2-c]pyridin-4(5H)-one.

MS (ESI+): [M+H]+ 338.0.

Example 32

2-(4-Chlorophenyl)-5-(4-cyclohexyl-3-methoxyphenyl)furo[3,2-c]pyridin-4(5H)-one The title compound was obtained in an analogous manner to Example 29 using cyclohexylmagnesium bromide (1 M solution in THF).

MS (ESI+): [M+H]+ 434.2.

Example 33

1-((4-(2-(4-Chlorophenyl)-4-oxofuro[3,2-c]pyridin-5 (4H)-yl)-2-methylphenoxy)methyl)cyclopropanecarbonitrile

A) 1-((4-Bromo-2-methylphenoxy)methyl)cyclopropanecarbonitrile

Thionyl chloride (0.59 mL) was added to a solution of 1-(hydroxymethyl)cyclopropanecarbonitrile (0.727 g) in toluene (30 mL) at room temperature. The resulting mixture was stirred at 80° C. for 2 hr. The reaction mixture was concentrated in vacuo, and the resulting residue was diluted with DMF (30 mL). 4-Bromo-2-methylphenol (1.00 g) and potassium carbonate (1.48 g) were added, and the mixture was stirred at 80° C. for 5 hr. The resulting mixture was purified by silica gel column chromatography (ethyl acetate/hexane) to give the title compound (1.10 g) as a colorless oil, which included a byproduct. The oil was subjected to the next reaction without further purification.

$^1$H NMR (400 MHz, CHLOROFORM-d) δ 1.38-1.43 (2H, m), 1.43-1.48 (2H, m), 2.25 (3H, s), 3.93 (2H, s), 6.59 (1H, d, J=8.7 Hz), 7.24 (1H, s), 7.28 (1H, s).

B) 1-((4-(2-(4-Chlorophenyl)-4-oxofuro[3,2-c]pyridin-5(4H)-yl)-2-methylphenoxy)methyl)cyclopropanecarbonitrile A mixture of 2-(4-chlorophenyl)furo[3,2-c]pyridin-4(5H)-one (200 mg), 1-((4-bromo-2-methylphenoxy)methyl)cyclopropanecarbonitrile (325 mg), N,N'-dimethylethylenediamine (0.087 ml), copper(I) iodide (155 mg), potassium carbonate (225 mg) and DMSO (3.0 mL) was heated at 190° C. for 1 hr under microwave irradiation. The resulting mixture was purified by silica gel column chromatography (NH, ethyl acetate/hexane) and the solid was recrystallized from ethanol to give the title compound (9.30 mg) as a pale yellow solid.

$^1$H NMR (400 MHz, DMSO-d$_6$) δ 1.38-1.43 (2H, m), 1.35-1.43 (2H, m), 2.27 (3H, s), 4.11 (2H, s), 6.85 (1H, d, J=7.3 Hz), 7.01 (1H, d, J=8.4 Hz), 7.22 (1H, d, J=8.4 Hz), 7.26 (1H, brs), 7.52-7.63 (4H, m), 7.91 (2H, d, J=8.4 Hz).

MS (ESI+): [M+H]+ 431.1.

Example 34

1-((3-(2-(4-Chlorophenyl)-4-oxofuro[3,2-c]pyridin-5 (4H)-yl) phenoxy)methyl)cyclopropanecarbonitrile The title compound was obtained in an analogous manner to Example 5 using 2-(4-chlorophenyl)-5-(3-hydroxyphenyl)furo[3,2-c]pyridin-4(5H)-one.

MS (ESI+): [M+H]+ 417.1.

Example 35

2-(4-Chlorophenyl)-5-(3-(3,3-dimethylbutoxy)phenyl)furo[3,2-c]pyridin-4(5H)-one Potassium carbonate (300 mg) was added to a mixture of 2-(4-chlorophenyl)-5-(3-hydroxyphenyl)furo[3,2-c]pyridin-4(5H)-one (110 mg), 1-bromo-3,3-dimethylbutane (161 mg) and DMF (1.0 mL) at room temperature, and the mixture was stirred at 80° C. for 3 hr. The resulting mixture was purified by silica gel column chromatography (ethyl acetate/hexane), and the solid was recrystallized from 2-propanol to give the title compound (69.6 mg) as a white solid.
MS (ESI+): [M+H]+ 422.1.

Example 36

2-(4-Chlorophenyl)-5-(3-methoxy-4-(tetrahydrofuran-2-ylmethoxy)phenyl)furo[3,2-c]pyridin-4(5H)-one Potassium carbonate (300 mg) was added to a mixture of 2-(4-chlorophenyl)-5-(4-hydroxy-3-methoxyphenyl)furo[3,2-c]pyridin-4(5H)-one (110 mg), 2-(chloromethyl)tetrahydrofuran (161 mg) and DMF (1.0 mL), and the mixture was stirred at 120° C. overnight. The resulting mixture was purified by silica gel column chromatography (NH, ethyl acetate/hexane), and the solid was recrystallized from ethanol to give the title compound (45.6 mg) as a white solid.
$^1$H NMR (400 MHz, CHLOROFORM-d) δ 1.76-1.87 (1H, m), 1.89-2.04 (2H, m), 2.06-2.16 (1H, m), 3.79-3.89 (4H, m), 3.95 (1H, q, J=7.0 Hz), 4.00-4.06 (1H, m), 4.06-4.13 (1H, m), 4.20-4.40 (1H, m), 6.63 (1H, d, J=7.4 Hz), 6.89 (1H, d, J=8.3 Hz), 6.93 (1H, s), 7.01 (1H, d, J=8.4 Hz), 7.23 (1H, s), 7.29 (1H, d, J=7.5 Hz), 7.42 (2H, d, J=8.2 Hz), 7.71 (2H, d, J=8.3 Hz).
MS (ESI+): [M+H]+ 452.4.

Example 37

5-(6-Bromo-1,2,3,4-tetrahydronaphthalen-2-yl)-2-(4-chlorophenyl)furo[3,2-c]pyridin-4(5H)-one A) Methyl 5-bromo-2-(2-methoxy-2-oxoethyl)-3-furoate N-Bromosuccinimide (8.90 g) was added portionwise to a solution of methyl 2-(2-methoxy-2-oxoethyl)-3-furoate (7.08 g) in DMF (80 mL) at room temperature, and the mixture was stirred at 50° C. overnight. To the resulting mixture was dropwise added brine, and the mixture was extracted with ethyl acetate four times. The resulting organic layer was washed with brine, dried over magnesium sulfate and concentrated in vacuo. The resulting residue was purified by silica gel column chromatography (ethyl acetate/hexane) to give the title compound (5.26 g) as a colorless oil.
$^1$H NMR (400 MHz, CHLOROFORM-d) δ 3.73 (3H, s), 3.82 (3H, s), 4.05 (2H, s), 6.62 (1H, s).

B) Methyl 5-(4-chlorophenyl)-2-(2-methoxy-2-oxoethyl)-3-furoate

A mixture of methyl 5-bromo-2-(2-methoxy-2-oxoethyl)-3-furoate (5.26 g), (4-chlorophenyl)boronic acid (5.94 g), potassium carbonate (5.25 g), (bis(diphenylphosphino) ferrocene)dichloropalladium(II) (0.139 g), toluene (100 mL) and water (10 mL) was stirred at 100° C. under argon atmosphere for 3 hr. The organic layer was separated and filtered through silica gel pad (NH), and the filtrate was concentrated in vacuo. The resulting residue was purified by silica gel column chromatography (ethyl acetate/hexane) to give the title compound (4.73 g) as a colorless oil.
$^1$H NMR (400 MHz, CHLOROFORM-d) δ 3.75 (3H, s), 3.85 (3H, s), 4.13 (2H, s), 6.92 (1H, s), 7.36 (2H, d, J=8.5 Hz), 7.58 (2H, d, J=8.5 Hz).

C) Methyl 5-(4-chlorophenyl)-2-(2-hydroxyethyl)-3-furoate

Sodium borohydride (1.2 g) was added to a mixture of methyl 5-(4-chlorophenyl)-2-(2-methoxy-2-oxoethyl)-3-furoate (4.73 g), methanol (100 mL) and THF (50 mL) at 50° C., and the mixture was stirred at 50° C. for 3 hr. Subsequently, sodium borohydride (1.2 g) was added three times every 20 min. To the resulting mixture was dropwise added brine, and the mixture was extracted with ethyl acetate twice. The resulting organic layer was washed with brine, dried over magnesium sulfate and concentrated in vacuo. The resulting residue was purified by silica gel column chromatography (ethyl acetate/hexane) to give the title compound (2.76 g) as a white amorphous solid.
MS (ESI+): [M+H]+ 281.0.

D) N-(6-Bromo-1,2,3,4-tetrahydronaphthalen-2-yl)-5-(4-chlorophenyl)-2-(2-hydroxyethyl)-3-furamide Triethylaluminum (1.8 M solution in toluene, 2.2 mL) was added to a solution of 6-bromo-1,2,3,4-tetrahydronaphthalen-2-amine (580 mg) in toluene (10 mL) at room temperature, and the mixture was stirred under nitrogen atmosphere for 2 hr. Methyl 5-(4-chlorophenyl)-2-(2-hydroxyethyl)-3-furoate (720 mg) was added to the resulting mixture at room temperature, and the mixture was stirred at 80° C. under nitrogen atmosphere for 2 hr. To the resulting mixture was dropwise added 1 N hydrochloric acid, and the mixture was extracted with ethyl acetate/THF twice. The resulting organic layer was washed with brine, dried over magnesium sulfate and concentrated in vacuo. The resulting residue was purified by silica gel column chromatography (NH, ethyl acetate/hexane) to give the title compound (780 mg) as a white solid.
MS (ESI+): [M+H]+ 474.0.

E) 5-(6-Bromo-1,2,3,4-tetrahydronaphthalen-2-yl)-2-(4-chlorophenyl)furo[3,2-c]pyridin-4(5H)-one Dess-Martin periodinane (179 mg) was added to a solution of N-(6-bromo-1,2,3,4-tetrahydronaphthalen-2-yl)-5-(4-chlorophenyl)-2-(2-hydroxyethyl)-3-furamide (100 mg) in acetonitrile (2 mL) at 0° C., and the mixture was stirred at room temperature under nitrogen stream overnight. To the resulting mixture was added saturated sodium hydrogen carbonate, and the mixture was extracted with ethyl acetate. The resulting organic layer was washed with brine, dried over magnesium sulfate and concentrated in vacuo. The resulting residue was purified by silica gel column chromatography (NH, ethyl acetate/hexane), and the solid was recrystallized from ethanol to give the title compound (7.80 mg) as a green solid.
MS (ESI+): [M+H]+ 454.0.

Example 38

2-(4-Chlorophenyl)-5-(4-(cyclopentylmethoxy)-3-methoxyphenyl)furo[3,2-c]pyridin-4(5H)-one The title compound was obtained in an analogous manner to Example 35 using 2-(4-chlorophenyl)-5-(4-hydroxy-3-methoxyphenyl)furo[3,2-c]pyridin-4(5H)-one and (bromomethyl)cyclopentane.
MS (ESI+): [M+H]+ 450.1.

Example 39

2-(4-Chlorophenyl)-5-(3-methoxy-4-(tetrahydrofuran-3-ylmethoxy)phenyl)furo[3,2-c]pyridin-4(5H)-one Potassium carbonate (60.1 mg) was added to a mixture of 2-(4-chlorophenyl)-5-(4-hydroxy-3-methoxyphenyl)furo[3,2-c]pyridin-4(5H)-one (80 mg), 3-(bromomethyl)tetrahydrofuran (53.8 mg) and DMF (1.5 mL) at room temperature, and the mixture was stirred at 80° C. for 2 hr. To the resulting mixture was dropwise added brine, and the mixture was extracted with ethyl acetate. The resulting organic layer was dried over magnesium sulfate and concentrated in vacuo. The resulting residue was purified by silica gel column chromatography (ethyl acetate/hexane), and the solid was recrystallized from ethanol to give the title compound (35.8 mg) as a white solid.

$^1$H NMR (400 MHz, CHLOROFORM-d) δ 1.70-1.87 (1H, m), 2.02-2.21 (1H, m), 2.67-2.97 (1H, m), 3.71-3.84 (2H, m), 3.85-3.89 (3H, m), 3.90-4.05 (4H, m), 6.64 (1H, d, J=7.5 Hz), 6.81-7.03 (3H, m), 7.16-7.33 (2H, m), 7.42 (2H, d, J=8.4 Hz), 7.71 (2H, d, J=8.5 Hz).

MS (ESI+): [M+H]+ 452.1.

Example 40

2-(4-Chlorophenyl)-5-(3-methoxy-4-(oxetan-3-ylmethoxy)phenyl)furo[3,2-c]pyridin-4(5H)-one DEAD (2.2 M solution in toluene, 0.13 mL) was added dropwise to a mixture of 2-(4-chlorophenyl)-5-(4-hydroxy-3-methoxyphenyl)furo[3,2-c]pyridin-4(5H)-one (80.0 mg), triphenylphosphine (74.2 mg), oxetan-3-ylmethanol (24.9 mg) and THF (1.5 mL) at room temperature, and the mixture was stirred overnight. To the resulting mixture was added brine, and the mixture was extracted with ethyl acetate twice. The resulting organic layer was washed with brine, dried over magnesium sulfate and concentrated in vacuo. The resulting residue was purified by silica gel column chromatography (NH, ethyl acetate/hexane), and the solid was recrystallized from ethanol to give the title compound (31.0 mg) as a white solid.

$^1$H NMR (400 MHz, CHLOROFORM-d) δ 3.52 (1H, dt, J=13.7, 6.7 Hz), 3.87 (3H, s), 4.32 (2H, d, J=7.0 Hz), 4.57 (2H, t, J=6.0 Hz), 4.92 (2H, t, J=7.0 Hz), 6.62-6.69 (1H, m), 6.89-6.93 (1H, m), 6.95 (1H, s), 7.00 (1H, d, J=8.3 Hz), 7.23 (1H, s), 7.29 (1H, d, J=7.5 Hz), 7.42 (2H, d, J=8.3 Hz), 7.71 (2H, d, J=8.2 Hz).

MS (ESI+): [M+H]+ 438.1.

Example 41

2-(4-Chlorophenyl)-5-(3-methoxy-4-((3-methyloxetan-3-yl)methoxy)phenyl)furo[3,2-c]pyridin-4(5H)-one DEAD (2.2 M solution in toluene, 0.13 mL) was added dropwise to a mixture of 2-(4-chlorophenyl)-5-(4-hydroxy-3-methoxyphenyl)furo[3,2-c]pyridin-4(5H)-one (80.0 mg), triphenylphosphine (74.2 mg), (3-methyloxetan-3-yl)methanol (28.9 mg) and THF (1.5 ml) at room temperature, and the mixture was stirred overnight. To the resulting mixture was added brine, and the mixture was extracted with ethyl acetate twice. The resulting organic layer was washed with brine, dried over magnesium sulfate and concentrated in vacuo. The resulting residue was purified by silica gel column chromatography (NH, ethyl acetate/hexane), followed by HPLC (C18, mobile phase: water/acetonitrile (including 0.1% TFA)). To the obtained fraction was added saturated aqueous sodium hydrogen carbonate solution, and the mixture was extracted with ethyl acetate. The extract was dried over anhydrous magnesium sulfate and concentrated in vacuo, and the solid was recrystallized from methanol to give the title compound (13.6 mg) as a white solid.

$^1$H NMR (400 MHz, CHLOROFORM-d) δ 1.49 (3H, s), 3.86 (3H, s), 4.12 (2H, s), 4.49 (2H, d, J=5.9 Hz), 4.66 (2H, d, J=5.9 Hz), 6.64 (1H, d, J=7.4 Hz), 6.89-6.94 (1H, m), 6.95 (1H, d, J=2.0 Hz), 7.02 (1H, d, J=8.4 Hz), 7.23 (1H, s), 7.29 (1H, d, J=7.5 Hz), 7.42 (2H, d, J=8.4 Hz), 7.71 (2H, d, J=8.4 Hz).

MS (ESI+): [M+H]+ 452.1.

Example 42

6-(2-(4-Chlorophenyl)-4-oxofuro[3,2-c]pyridin-5(4H)-yl)-5,6,7,8-tetrahydronaphthalene-2-carbonitrile Copper(I) cyanide (29.5 mg) was added to a mixture of 5-(6-bromo-1,2,3,4-tetrahydronaphthalen-2-yl)-2-(4-chlorophenyl)furo[3,2-c]pyridin-4(5H)-one (50.0 mg) and DMA (1.0 mL) at room temperature, and the mixture was heated at 210° C. for 1 hr under microwave irradiation. The resulting mixture was purified by silica gel column chromatography (NH, ethyl acetate/hexane) to give the title compound (11.2 mg) as a brown solid.

$^1$H NMR (400 MHz, CHLOROFORM-d) δ 2.10-2.28 (2H, m), 2.92-3.18 (3H, m), 3.33 (1H, dd, J=17.0, 5.2 Hz), 5.43 (1H, dq, J=10.3, 5.1 Hz), 6.64 (1H, d, J=7.5 Hz), 7.18-7.24 (3H, m), 7.38-7.49 (4H, m), 7.70 (2H, d, J=8.4 Hz).

MS (ESI+): [M+H]+ 401.1.

Example 43

2-(4-Chlorophenyl)-5-(3-methoxy-4-(oxetan-2-ylmethoxy)phenyl)furo[3,2-c]pyridin-4(5H)-one DEAD (2.2 M solution in toluene, 0.13 mL) was added dropwise to a mixture of 2-(4-chlorophenyl)-5-(4-hydroxy-3-methoxyphenyl)furo[3,2-c]pyridin-4(5H)-one (80.0 mg), triphenylphosphine (74.2 mg), oxetan-2-ylmethanol (24.9 mg) and THF (2.0 mL) at room temperature, and the mixture was stirred overnight. The resulting precipitate was collected by filtration and washed with THF to give the title compound (57.8 mg) as a white solid.

$^1$H NMR (400 MHz, CHLOROFORM-d) δ 2.64-2.91 (2H, m), 3.88 (3H, s), 4.25 (2H, d, J=4.3 Hz), 4.61-4.79 (2H, m), 5.11-5.27 (1H, m), 6.63 (1H, d, J=7.5 Hz), 6.90 (1H, d, J=8.2 Hz), 6.95 (1H, d, J=2.1 Hz), 7.07 (1H, d, J=8.5 Hz), 7.21-7.32 (2H, m), 7.42 (2H, d, J=8.4 Hz), 7.71 (2H, d, J=8.5 Hz).

MS (ESI+): [M+H]+ 438.1.

Example 44

2-(4-Chlorophenyl)-5-(4-((2,2-difluorocyclopropyl)methoxy)-3-methoxyphenyl)furo[3,2-c]pyridin-4(5H)-one Potassium carbonate (60.1 mg) was added to a mixture of 2-(4-chlorophenyl)-5-(4-hydroxy-3-methoxyphenyl)furo[3,2-c]pyridin-4(5H)-one (80.0 mg), 2-(bromomethyl)-1,1-difluorocyclopropane (74.4 mg) and DMF (2.0 mL) at room temperature, and the mixture was stirred at 80° C. for 3 hr. The resulting mixture was purified by silica gel column chromatography (NH, ethyl acetate/hexane), and the solid was recrystallized from ethanol to give the title compound (40.2 mg) as a white solid.

$^1$H NMR (400 MHz, CHLOROFORM-d) δ 1.27-1.39 (1H, m), 1.57-1.68 (1H, m), 2.00-2.25 (1H, m), 3.89 (3H, s), 4.08 (1H, brs), 4.21 (1H, d, J=7.7 Hz), 6.64 (1H, d, J=7.5 Hz), 6.87-6.93 (1H, m), 6.95-7.00 (2H, m), 7.23 (1H, s), 7.29 (1H, d, J=7.4 Hz), 7.42 (2H, d, J=8.4 Hz), 7.71 (2H, d, J=8.5 Hz).

MS (ESI+): [M+H]+ 458.1.

Example 45

4-(2-(4-Chlorophenyl)-4-oxofuro[3,2-c]pyridin-5 (4H)-yl)-N-(cyclopropylmethyl)-2-methoxybenzamide A)
4-Bromo-N-(cyclopropylmethyl)-2-methoxybenzamide To a solution of 4-bromo-2-methoxybenzoic acid (1.0 g) in dichloromethane (10 mL) were added HATU (2.5 g) and N,N'-diisopropylethylamine (1.9 mL) at 0° C., and the mixture was stirred at room temperature for 30 min. To the resulting mixture was added 1-cyclopropylmethanamine (0.38 mL), and the mixture was stirred at room temperature for 18 hr. The reaction mixture was concentrated, and the residue was dissolved in dichloromethane. The solution was successively washed with saturated aqueous ammonium chloride solution, saturated aqueous sodium hydrogen carbonate solution, water and brine, dried over sodium sulfate and concentrated in vacuo to give the title compound (1.1 g) as a pale yellow solid.

MS (ESI+): [M+H]+ 283.8.

B) 4-(2-(4-Chlorophenyl)-4-oxofuro[3,2-c]pyridin-5 (4H)-yl)-N-(cyclopropylmethyl)-2-methoxybenzamide To a mixture of 4-bromo-N-(cyclopropylmethyl)-2-methoxybenzamide (145 mg), 2-(4-chlorophenyl)furo[3,2-c]pyridin-4(5H)-one (100 mg), potassium carbonate (169 mg) and dioxane (2.0 mL) were added copper(I) iodide (31.0 mg) and trans-N,N'-dimethylcyclohexane-1,2-diamine (23.0 mg). The mixture was stirred in a sealed tube at 110° C. for 16 hr. The reaction mixture was cooled and concentrated. The resulting residue was diluted with dichloromethane, and the solution was washed with brine, dried over sodium sulfate and concentrated in vacuo. The resulting residue was purified by silica gel column chromatography (methanol/dichloromethane) to give the title compound (20.0 mg) as a white solid.

$^1$H NMR (400 MHz, DMSO-d$_6$): δ 0.25 (2H, d, J=6.8 Hz), 0.43 (2H, d, J=6.8 Hz), 1.05 (1H, m), 3.17-3.20 (2H, m), 3.91 (3H, s), 6.92 (1H, d, J=7.1 Hz), 7.10 (1H, d, J=8.0 Hz), 7.26 (1H, s), 7.55-7.68 (4H, m), 7.80-7.92 (3H, m), 8.31 (1H, m).

MS (ESI+): [M+H]+ 449.0.

Example 46

2-(4-Chlorophenyl)-5-(4-(1-hydroxyethyl)-3-methoxyphenyl)furo[3,2-c]pyridin-4(5H)-one A) 1-(4-Bromo-2-methoxyphenyl)ethanol To a mixture of 4-bromo-2-methoxybenzaldehyde (250 mg) and THF (10 mL) was added methylmagnesium bromide (3.0 M solution in diethyl ether, 1.1 mL) at 0° C., and the mixture was stirred for 1 hr. To the resulting mixture was dropwise added saturated aqueous ammonium chloride solution at 0° C., and the mixture was extracted with ethyl acetate. The resulting organic layer was washed with brine, dried over sodium sulfate and concentrated in vacuo to give the title compound (250 mg) as a pale yellow oil, which was used for the next step without further purification.

$^1$H NMR (400 MHz, DMSO-d$_6$) δ 1.22 (3H, d, J=6.4 Hz), 3.79 (3H, s), 4.91 (1H, m), 5.05 (1H, d, J=4.4 Hz), 7.10-7.13 (2H, m), 7.35 (1H, d, J=7.9 Hz).

B) 2-(4-Chlorophenyl)-5-(4-(1-hydroxyethyl)-3-methoxyphenyl)furo[3,2-c]pyridin-4(5H)-one The title compound was obtained in an analogous manner to step B in Example 8 using 1-(4-bromo-2-methoxyphenyl) ethanol.

MS (ESI+): [M+H]+ 396.2.

Example 47

1-((4-(2-(4-Chlorophenyl)-4-oxofuro[3,2-c]pyridin-5 (4H)-yl)-2-ethylphenoxy)methyl)cyclopropanecarbonitrile A) 1-((4-Bromo-2-ethylphenoxy)methyl)cyclopropanecarbonitrile To a mixture of 4-bromo-2-ethylphenol (300 mg), (1-cyanocyclopropyl)methyl 4-methylbenzenesulfonate (374 mg) and DMF (5.0 mL) was added potassium carbonate (616 mg) at room temperature, and the mixture was stirred at 120° C. for 16 hr. The reaction mixture was then cooled to room temperature and filtered through celite. The obtained filtrate was diluted with water and the mixture was extracted with dichloromethane. The organic layer was washed with brine, dried over sodium sulfate and concentrated in vacuo. The resulting residue was purified by silica gel column chromatography (ethyl acetate/hexane) to give the title compound (210 mg) as a white solid.

$^1$H NMR (400 MHz, DMSO-d$_6$) δ 1.13-1.18 (5H, m), 1.35-1.38 (2H, m), 2.58-2.64 (2H, m), 4.02 (2H, s), 6.85 (1H, d, J=8.3 Hz), 7.31 (1H, d, J=2.4 Hz), 7.33 (1H, s).

B) 1-((4-(2-(4-Chlorophenyl)-4-oxofuro[3,2-c]pyridin-5(4H)-yl)-2-ethylphenoxy)methyl)cyclopropanecarbonitrile To a mixture of 1-((4-bromo-2-ethylphenoxy)methyl)cyclopropanecarbonitrile (250 mg), 2-(4-chlorophenyl)furo[3,2-c]pyridin-4(5H)-one (174 mg), potassium carbonate (369 mg) and dioxane (10 mL) were added copper(I) iodide (67.0 mg) and trans-N,N'-dimethylcyclohexane-1,2-diamine (50.0 mg). The mixture was heated in a sealed tube at 110° C. for 16 hr. The reaction mixture was concentrated, and the residue was diluted with dichloromethane (150 ml), washed with brine, dried over sodium sulfate and concentrated in vacuo. The resulting residue was purified by silica gel column chromatography (methanol/dichloromethane) to give the title compound (35.0 mg) as brown solid.

$^1$H NMR (400 MHz, DMSO-d$_6$) δ 1.17-1.23 (5H, m), 1.39-1.42 (2H, m), 2.67-2.69 (2H, m), 4.10 (2H, s), 6.84 (1H, d, J=7.4 Hz), 7.01 (1H, d, J=8.9 Hz), 7.21-7.23 (2H, m), 7.55 (2H, d, J=8.5 Hz), 7.59-7.60 (2H, m), 7.90 (2H, d, J=8.6 Hz).

MS (ESI+): [M+H]+ 445.2.

Example 48

2-(4-Chlorophenyl)-5-(4-((3-ethyloxetan-3-yl)methoxy)-3-methoxyphenyl)furo[3,2-c]pyridin-4(5H)-one DEAD (2.2 M solution in toluene, 0.20 mL) was added dropwise to a mixture of 2-(4-chlorophenyl)-5-(4-hydroxy-3-methoxyphenyl)furo[3,2-c]pyridin-4(5H)-one (80.0 mg), triphenylphosphine (114 mg), (3-ethyloxetan-3-yl)methanol (50.5 mg) and THF (2.0 mL) at room temperature, and the mixture was stirred at room temperature overnight. The resulting precipitate was collected by filtration and washed with THF to give the title compound (91.7 mg) as a white solid.

$^1$H NMR (400 MHz, CHLOROFORM-d) δ 0.97 (3H, t, J=7.4 Hz), 1.94 (2H, q, J=7.3 Hz), 3.86 (3H, s), 4.18 (2H, s), 4.52 (2H, d, J=6.1 Hz), 4.61 (2H, d, J=6.0 Hz), 6.64 (1H, d, J=7.3 Hz), 6.84-6.97 (2H, m), 7.03 (1H, d, J=8.4 Hz), 7.20-7.31 (2H, m), 7.42 (2H, d, J=8.5 Hz), 7.71 (2H, d, J=8.4 Hz).

MS (ESI+): [M+H]+ 466.1.

Example 49

5-(2-(4-Bromophenyl)ethyl)-2-(4-chlorophenyl)furo[3,2-c]pyridin-4(5H)-one

Cesium carbonate (133 mg) was added to a mixture of 4-bromophenethyl 4-methylbenzenesulfonate (94.0 mg), 2-(4-chlorophenyl)furo[3,2-c]pyridin-4(5H)-one (50.0 mg) and DMF (2.0 mL) at 80° C., and the mixture was stirred overnight. The resulting mixture was purified by silica gel column chromatography (NH, ethyl acetate/hexane), and the solid was recrystallized from ethanol to give the title compound (44.3 mg) as a white solid.

$^1$H NMR (400 MHz, CHLOROFORM-d) δ 3.05 (2H, t, J=7.0 Hz), 4.22 (2H, t, J=7.0 Hz), 6.43 (1H, d, J=7.3 Hz), 6.84 (1H, d, J=7.4 Hz), 7.03 (2H, d, J=8.3 Hz), 7.20 (1H, s), 7.36-7.44 (4H, m), 7.69 (2H, d, J=8.4 Hz).

MS (ESI+): [M+H]+ 428.0.

Example 50

2-(4-(2-(4-Chlorophenyl)-4-oxofuro[3,2-c]pyridin-5(4H)-yl)-2-methoxyphenoxy)acetamide A) 2-(4-Bromo-2-methoxyphenoxy)acetamide To a mixture of 4-bromo-2-methoxyphenol (500 mg), 2-bromoacetamide (425 mg) and acetone (5.0 mL) was added potassium carbonate (1.02 g) at room temperature, and the mixture was heated at 60° C. for 6 hr. The reaction mixture was concentrated in vacuo. The residue was diluted with water and extracted with ethyl acetate. The resulting organic layer was washed with brine, dried over sodium sulfate and concentrated in vacuo to give the title compound (600 mg) as a white solid, which was used for the next step without further purification.

MS (ESI+): [M+H]+ 260.2.

B) 2-(4-(2-(4-Chlorophenyl)-4-oxofuro[3,2-c]pyridin-5(4H)-yl)-2-methoxyphenoxy)acetamide To a mixture of 2-(4-chlorophenyl)furo[3,2-c]pyridin-4(5H)-one (200 mg), 2-(4-bromo-2-methoxyphenoxy) acetamide (214 mg), potassium carbonate (338 mg) and dioxane (5 mL) were added copper(I) iodide (62 mg) and trans-N,N'-dimethylcyclohexane-1,2-diamine (46.0 mg). The mixture was heated in a sealed tube at 110° C. for 16 hr. The reaction mixture was concentrated. The residue was diluted with dichloromethane, and the organic layer was washed with brine, dried over sodium sulfate and concentrated in vacuo. The resulting residue was purified by HPLC (C18, mobile phase: water/acetocnitrile (including 0.1% TFA)). To the obtained fraction was added saturated aqueous sodium hydrogen carbonate solution, and the mixture was extracted with ethyl acetate. The extract was dried over anhydrous magnesium sulfate and concentrated in vacuo to give the title compound (25.0 mg) as a light brown solid.

$^1$H NMR (400 MHz, DMSO-d$_6$) δ 3.81 (3H, s), 4.50 (2H, s), 6.85 (1H, d, J=7.4 Hz), 6.93 (1H, dd, J=2.2, 8.5 Hz), 7.01 (1H, d, J=8.5 Hz), 7.09 (1H, d, J=2.2 Hz), 7.38 (1H, brs), 7.42 (1H, brs), 7.55 (2H, d, J=8.6 Hz), 7.61-7.62 (2H, m), 7.90 (2H, d, J=8.6 Hz).

(ESI+): [M+H]+ 425.0.

Example 51

4-(4-(2-(4-Chlorophenyl)-4-oxofuro[3,2-c]pyridin-5(4H)-yl)-2-methoxyphenoxy)butanamide A) Ethyl 4-(4-bromo-2-methoxyphenoxy)butanoate To a mixture of 4-bromo-2-methoxyphenol (500 mg), ethyl 4-bromobutanoate (480 mg) and acetone (5.0 mL) was added potassium carbonate (1.02 g) at room temperature, and the mixture was stirred at 60° C. for 6 hr. The reaction mixture was concentrated. The residue was diluted with water and extracted with ethyl acetate. The resulting organic layer was washed with brine, dried over sodium sulfate and concentrated in vacuo to give the title compound (500 mg) as a white solid, which was used for the next step without further purification.

MS (ESI+): [M+H]+ 317.4.

B) 4-(4-Bromo-2-methoxyphenoxy)butanoic acid

To a mixture of ethyl 4-(4-bromo-2-methoxyphenoxy)butanoate (800 mg), THF (3.0 mL), methanol (2.0 mL) and water (1.0 mL) was added lithium hydroxide monohydrate (317 mg), and the mixture was stirred at room temperature for 3 hr. The reaction mixture was concentrated, and the aqueous layer was washed with ethyl acetate, diluted with water (10 mL) and neutralized with 2 N hydrochloric acid. The resulting precipitate was collected by filtration to give the title compound (650 mg), which was used for the next step without further purification.

MS (ESI−): [M−H]− 286.8.

C) 4-(4-Bromo-2-methoxyphenoxy)butanamide

The title compound was obtained in an analogous manner to step B in Example 45 using 4-(4-bromo-2-methoxyphenoxy)butanoic acid and ammonium chloride.

MS (ESI+): [M+H]+ 289.2.

D) 4-(4-(2-(4-Chlorophenyl)-4-oxofuro[3,2-c]pyridin-5(4H)-yl)-2-methoxyphenoxy)butanamide To a mixture of 4-(4-bromo-2-methoxyphenoxy)butanamide (178 mg), 2-(4-chlorophenyl)furo[3,2-c]pyridin-4(5H)-one (150 mg) and potassium carbonate (253 mg) in dioxane (5 mL) were added copper(I) iodide (47.0 mg) and trans-N,N'-dimethylcyclohexane-1,2-diamine (71.0 mg). The mixture was stirred in a sealed tube at 110° C. for 16 hr. The resulting mixture was allowed to cool to room temperature and concentrated in vacuo. The resulting residue was diluted with dichloromethane, washed with brine, dried over sodium sulfate and concentrated in vacuo. The resulting residue was purified by silica gel column chromatography (methanol/dichloromethane), followed by HPLC (C18, mobile phase: water/acetonitrile (including 0.1% TFA)). To the obtained fraction was added saturated aqueous sodium hydrogen carbonate solution, and the mixture was extracted with ethyl acetate. The extract was dried over anhydrous magnesium sulfate and concentrated in vacuo to give the title compound (10 mg) as a light brown solid.

$^1$H NMR (400 MHz, DMSO-$d_6$) δ 1.94 (2H, t, J=7.1 Hz), 2.24 (2H, t, J=7.3 Hz), 3.78 (3H, s), 4.02 (2H, t, J=6.3 Hz), 6.77 (1H, brs), 6.85 (1H, d, J=7.5 Hz), 6.91 (1H, dd, J=2.2, 8.5 Hz), 7.04-7.07 (2H, m), 7.33 (1H, brs), 7.55 (2H, d, J=8.6 Hz), 7.61-7.62 (2H, m), 7.90 (2H, d, J=8.6 Hz).

MS (ESI+): [M+H]+ 453.2.

Example 52

1-((4-(2-(4-Chlorophenyl)-4-oxofuro[2,3-d]pyridazin-5(4H)-yl)-2-methoxyphenoxy)methyl)cyclopropanecarbonitrile A) 1-((4-Bromo-2-methoxyphenoxy)methyl)cyclopropanecarbonitrile Thionyl chloride (0.23 mL) was added to a solution of 4-bromo-2-methoxyphenol (209 mg) in toluene (2.0 mL) at room temperature, and the mixture was stirred at 80° C. for 2 hr. The reaction mixture was concentrated and diluted with DMF (2.0 mL). 4-Bromo-2-methoxyphenol (209 mg) and potassium carbonate (356 mg) were added, and the mixture was stirred at 80° C. overnight. To the resulting mixture was added brine, and the mixture was extracted with ethyl acetate, dried over magnesium sulfate and concentrated in vacuo. The resulting residue was purified by silica gel column chromatography (ethyl acetate/hexane) to give the title compound (165 mg) as a colorless oil.

$^1$H NMR (400 MHz, CHLOROFORM-d) δ 1.06-1.13 (2H, m), 1.31-1.41 (2H, m), 3.85 (3H, s), 3.98 (2H, s), 6.76-6.89 (1H, m), 6.98-7.04 (2H, m).

B) 2-(4-Chlorophenyl)furo[2,3-d]pyridazin-4(5H)-one

Hydrazine monohydrate (0.044 mL) was added to a mixture of 5-(4-chlorophenyl)-2-formyl-3-furoic acid (250 mg) and acetic acid (3.0 mL) at room temperature, and the mixture was stirred at 200° C. for 30 min under microwave irradiation. The resulting precipitate was collected by filtration and washed with acetic acid to give the title compound (189 mg) as a pale red solid.

$^1$H NMR (300 MHz, methanol-$d_4$): δ 7.45 (1H, s), 7.52-7.58 (2H, m), 7.95 (2H, d, J=8.8 Hz), 8.49 (1H, s).

C) 1-((4-(2-(4-Chlorophenyl)-4-oxofuro[2,3-d]pyridazin-5(4H)-yl)-2-methoxyphenoxy)methyl)cyclopropanecarbonitrile A mixture of 2-(4-chlorophenyl)furo[2,3-d]pyridazin-4(5H)-one (25.0 mg), 1-((4-bromo-2-methoxyphenoxy)methyl)cyclopropanecarbonitrile (57.2 mg), N,N'-dimethylethylenediamine (0.032 mL), copper(I) iodide (57.9 mg), potassium carbonate (42.0 mg) and DMSO (1.0 mL) was heated at 200° C. for 1 hr under microwave irradiation. The resulting mixture was purified by silica gel column chromatography (ethyl acetate/hexane), and the solid was recrystallized from ethanol to give the title compound (4.90 mg) as a white solid.

$^1$H NMR (400 MHz, CHLOROFORM-d) δ 1.03-1.15 (2H, m), 1.29-1.41 (2H, m), 3.90 (3H, s), 4.01 (2H, s), 6.86-6.90 (1H, m), 6.92 (1H, s), 6.98 (1H, d, J=8.7 Hz), 7.40 (2H, d, J=8.5 Hz), 7.51-7.55 (1H, m), 7.63 (2H, d, J=8.4 Hz), 8.03 (1H, s).

TABLE 1

| Ex. | IUPAC name | Structure | MS |
|---|---|---|---|
| 1 | 6-(4-chlorophenyl)-3-(3,4-dimethoxyphenyl)-furo[2,3-d]pyrimidin-4(3H)-one | 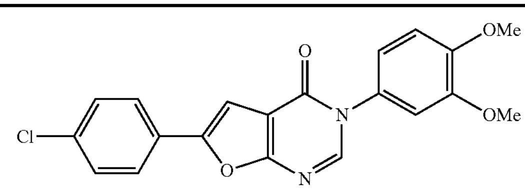 | 383.1 |
| 2 | 2-(4-chlorophenyl)-5-(3,4-dimethoxyphenyl)-furo[3,2-c]pyridin-4(5H)-one | 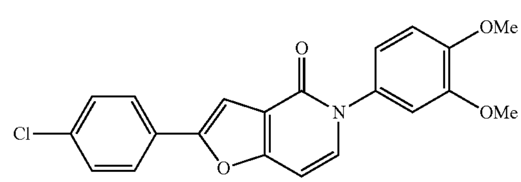 | 382.1 |
| 3 | 4-(2-(2-(4-chlorophenyl)-4-oxofuro[3,2-c]pyridin-5(4H)-yl)ethyl)-benzonitrile | 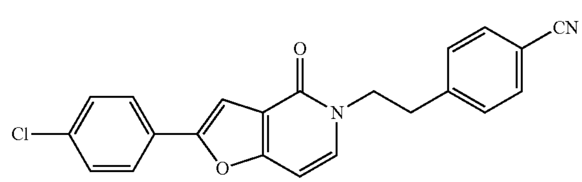 [SMILES: N#Cc1ccc(CCn2ccc3oc(-c4ccc(Cl)cc4)cc3c2=O)cc1] | 375.1 |

TABLE 1-continued

| Ex. | IUPAC name | Structure | MS |
|---|---|---|---|
| 4 | 2-(4-chlorophenyl)-5-(4-methoxyphenyl)furo[3,2-c]pyridin-4(5H)-one | 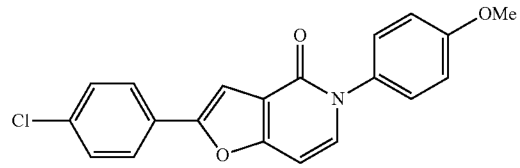 [SMILES: COc1ccc(-n2ccc3oc(-c4ccc(Cl)cc4)cc3c2=O)cc1] | 352.1 |
| 5 | 1-((4-(2-(4-chlorophenyl)-4-oxofuro[3,2-c]pyridin-5(4H)-yl)-2-methoxyphenoxy)methyl)-cyclopropanecarbonitrile | 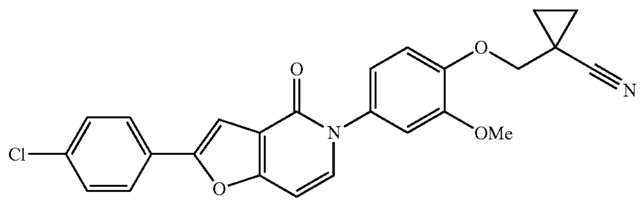 [SMILES: COc1cc(-n2ccc3oc(-c4ccc(Cl)cc4)cc3c2=O)ccc1OCC1(C#N)CC1] | 447.1 |
| 6 | 1-((4-(6-(4-chlorophenyl)-4-oxofuro[2,3-d]pyrimidin-3(4H)-yl)-2-methoxyphenoxy)methyl)-cyclopropanecarbonitrile | 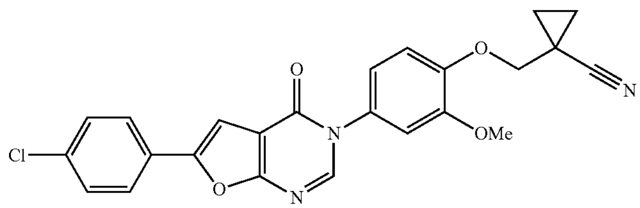 [SMILES: COc1cc(-n2cnc3oc(-c4ccc(Cl)cc4)cc3c2=O)ccc1OCC1(C#N)CC1] | 448.1 |
| 7 | 2-(4-chlorophenyl)-5-(4-(2-hydroxy-2-methylpropoxy)-3-methoxyphenyl)furo[3,2-c]pyridin-4(5H)-one | 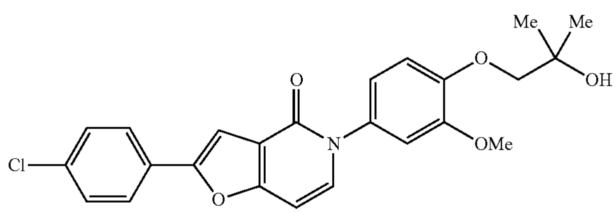 [SMILES: COc1cc(-n2ccc3oc(-c4ccc(Cl)cc4)cc3c2=O)ccc1OCC(C)(C)O] | 440.1 |
| 8 | 1-((2-chloro-4-(2-(4-chlorophenyl)-4-oxofuro[3,2-c]pyridin-5(4H)-yl)-phenoxy)methyl)-cyclopropanecarbonitrile | 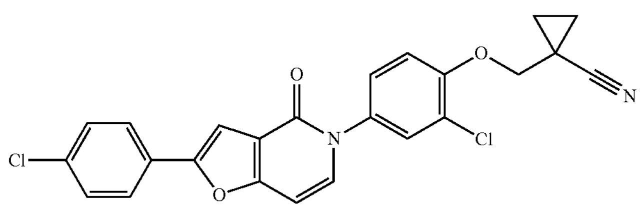 [SMILES: N#CC1(COc2ccc(-n3ccc4oc(-c5ccc(Cl)cc5)cc4c3=O)cc2Cl)CC1] | 451.1 |
| 9 | 1-(((3-chloro-5-(2-(4-chlorophenyl)-4-oxofuro[3,2-c]pyridin-5(4H)-yl)pyridin-2-yl)oxy)methyl)-cyclopropanecarbonitrile | 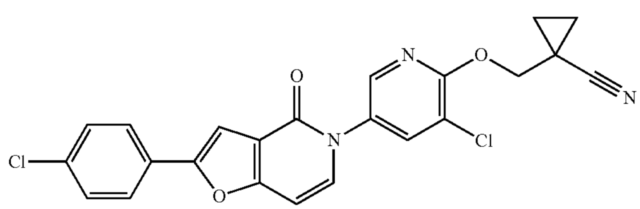 [SMILES: N#CC1(COc2ncc(-n3ccc4oc(-c5ccc(Cl)cc5)cc4c3=O)cc2Cl)CC1] | 452.1 |
| 10 | 1-((4-(2-(4-fluorophenyl)-4-oxofuro[3,2-c]pyridin-5(4H)-yl)-2-methoxyphenoxy)methyl)-cyclopropanecarbonitrile | 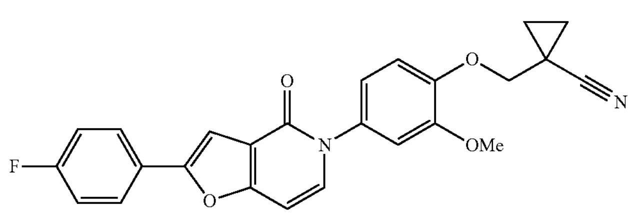 [SMILES: COc1cc(-n2ccc3oc(-c4ccc(F)cc4)cc3c2=O)ccc1OCC1(C#N)CC1] | 431.1 |

TABLE 1-continued

| Ex. | IUPAC name | Structure | MS |
|---|---|---|---|
| 11 | 1-((4-(2-(3-fluorophenyl)-4-oxofuro[3,2-c]pyridin-5(4H)-yl)-2-methoxyphenoxy)methyl)-cyclopropanecarbonitrile | 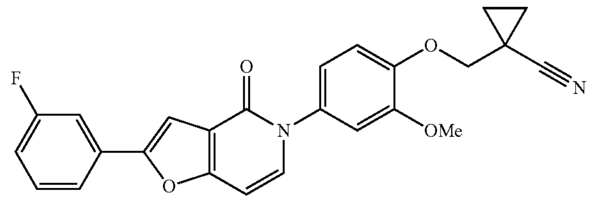 [SMILES: COc1cc(-n2ccc3oc(-c4cccc(F)c4)cc3c2=O)ccc1OCC1(C#N)CC1] | 431.1 |
| 12 | 1-((4-(2-(5-chloro-2-thienyl)-4-oxofuro[3,2-c]pyridin-5(4H)-yl)-2-methoxyphenoxy)methyl)-cyclopropanecarbonitrile | 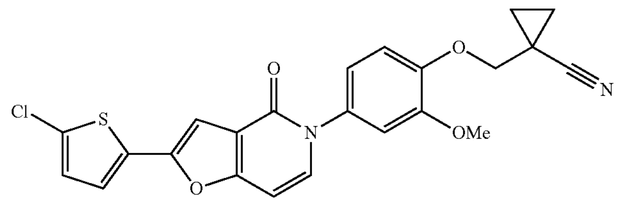 [SMILES: COc1cc(-n2ccc3oc(-c4ccc(Cl)s4)cc3c2=O)ccc1OCC1(C#N)CC1] | 453 |
| 13 | 1-((2-methoxy-4-(4-oxo-2-(3-thienyl)furo[3,2-c]pyridin-5(4H)-yl)phenoxy)methyl)-cyclopropanecarbonitrile | 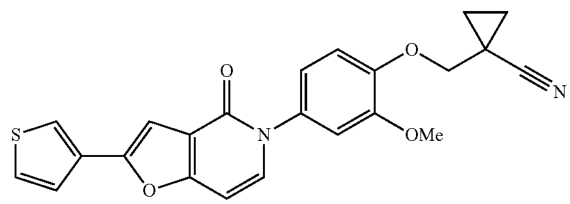 [SMILES: COc1cc(-n2ccc3oc(-c4ccsc4)cc3c2=O)ccc1OCC1(C#N)CC1] | 419.1 |
| 14 | 1-((2-methoxy-4-(4-oxo-2-(2-thienyl)furo[3,2-c]pyridin-5(4H)-yl)phenoxy)methyl)-cyclopropanecarbonitrile | 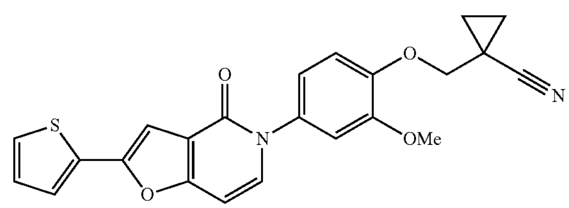 [SMILES: COc1cc(-n2ccc3oc(-c4cccs4)cc3c2=O)ccc1OCC1(C#N)CC1] | 419.1 |
| 15 | 1-((4-(2-(2-fluorophenyl)-4-oxofuro[3,2-c]pyridin-5(4H)-yl)-2-methoxyphenoxy)methyl)-cyclopropanecarbonitrile | 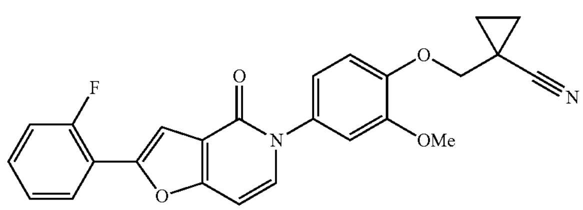 [SMILES: COc1cc(-n2ccc3oc(-c4ccccc4F)cc3c2=O)ccc1OCC1(C#N)CC1] | 431.1 |
| 16 | 1-((2-methoxy-4-(2-(4-methoxyphenyl)-4-oxofuro[3,2-c]pyridin-5(4H)-yl)-phenoxy)methyl)-cyclopropanecarbonitrile | 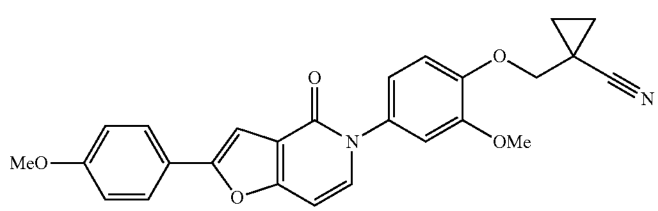 [SMILES: COc1ccc(-c2cc3c(=O)n(-c4ccc(OCC5(C#N)CC5)c(OC)c4)ccc3o2)cc1] | 443.1 |
| 17 | 1-((2-methoxy-4-(2-(3-methoxyphenyl)-4-oxofuro[3,2-c]pyridin-5(4H)-yl)-phenoxy)methyl)-cyclopropanecarbonitrile | 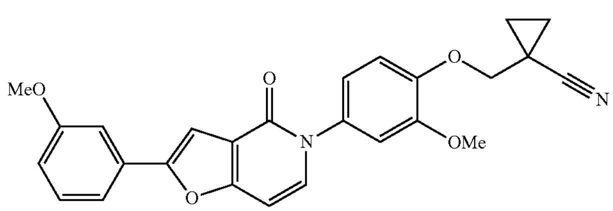 [SMILES: COc1cccc(-c2cc3c(=O)n(-c4ccc(OCC5(C#N)CC5)c(OC)c4)ccc3o2)c1] | 443.1 |

TABLE 1-continued

| Ex. | IUPAC name | Structure | MS |
|---|---|---|---|
| 18 | 1-((4-(2-(3,4-difluorophenyl)-4-oxofuro[3,2-c]pyridin-5(4H)-yl)-2-methoxyphenoxy)methyl)-cyclopropanecarbonitrile | 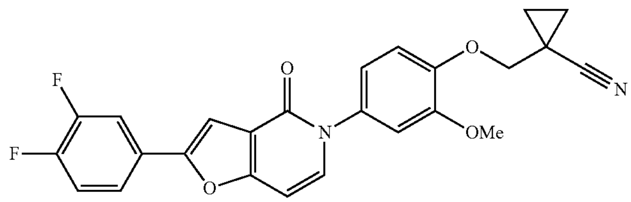 [SMILES: COc1cc(-n2ccc3oc(-c4ccc(F)c(F)c4)cc3c2=O)ccc1OCC1(C#N)CC1] | 449.1 |
| 19 | 1-((4-(2-(5-chloropyridin-2-yl)-4-oxofuro[3,2-c]pyridin-5(4H)-yl)-2-methoxyphenoxy)methyl)-cyclopropanecarbonitrile | 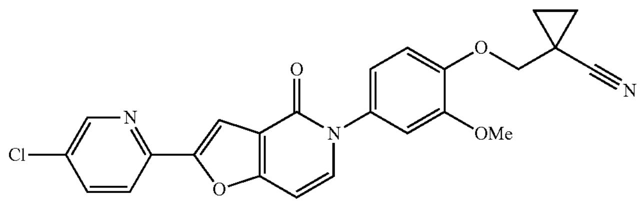 [SMILES: COc1cc(-n2ccc3oc(-c4ccc(Cl)cn4)cc3c2=O)ccc1OCC1(C#N)CC1] | 448.1 |
| 20 | 1-((2-methoxy-4-(4-oxo-2-phenylfuro[3,2-c]pyridin-5(4H)-yl)phenoxy)methyl)-cyclopropanecarbonitrile | 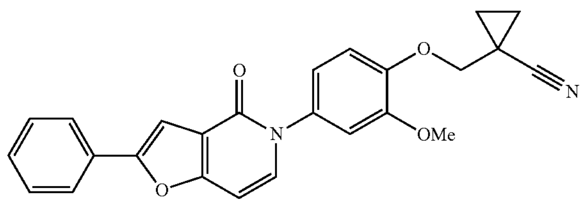 [SMILES: COc1cc(-n2ccc3oc(-c4ccccc4)cc3c2=O)ccc1OCC1(C#N)CC1] | 413.1 |
| 21 | 1-((4-(2-(5-fluoropyridin-2-yl)-4-oxofuro[3,2-c]pyridin-5(4H)-yl)-2-methoxyphenoxy)methyl)-cyclopropanecarbonitrile | 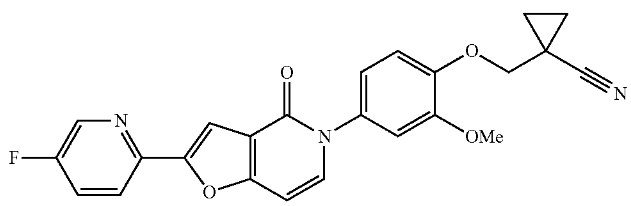 [SMILES: COc1cc(-n2ccc3oc(-c4ccc(F)cn4)cc3c2=O)ccc1OCC1(C#N)CC1] | 432.1 |
| 22 | 5-(4-bromo-3-methoxyphenyl)-2-(4-chlorophenyl)furo[3,2-c]pyridin-4(5H)-one | 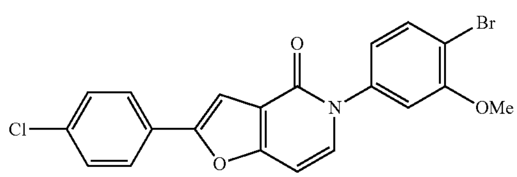 [SMILES: COc1cc(-n2ccc3oc(-c4ccc(Cl)cc4)cc3c2=O)ccc1Br] | 430 |
| 23 | 1-(((5-(2-(4-chlorophenyl)-4-oxofuro[3,2-c]pyridin-5(4H)-yl)-3-methoxypyridin-2-yl)oxy)methyl)-cyclopropanecarbonitrile | 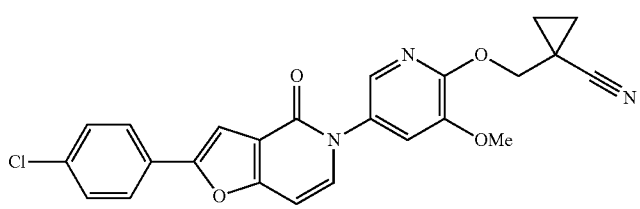 [SMILES: COc1cc(-n2ccc3oc(-c4ccc(Cl)cc4)cc3c2=O)cnc1OCC1(C#N)CC1] | 448.1 |
| 24 | methyl 4-(2-(4-chlorophenyl)-4-oxofuro[3,2-c]pyridin-5(4H)-yl)-2-methoxybenzoate | 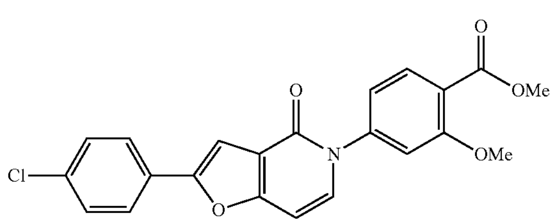 [SMILES: COC(=O)c1ccc(-n2ccc3oc(-c4ccc(Cl)cc4)cc3c2=O)cc1OC] | 410 |
| 25 | 2-(4-chlorophenyl)-5-(4-ethyl-3-methoxyphenyl)furo[3,2-c]pyridin-4(5H)-one | 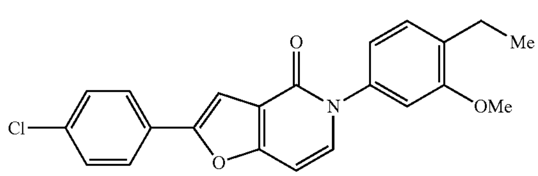 [SMILES: CCc1ccc(-n2ccc3oc(-c4ccc(Cl)cc4)cc3c2=O)cc1OC] | 380.1 |

TABLE 1-continued

| Ex. | IUPAC name | Structure | MS |
|---|---|---|---|
| 26 | 2-(4-chlorophenyl)-5-(4-hydroxyphenyl)furo[3,2-c]pyridin-4(5H)-one | 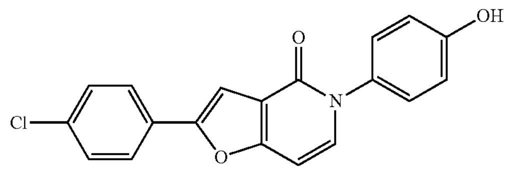 [SMILES: O=c1c2cc(-c3ccc(Cl)cc3)oc2ccn1-c1ccc(O)cc1] | 338 |
| 27 | 1-((2-methoxy-4-(4-oxo-2-(4-(trifluoromethyl)phenyl)furo[3,2-c]pyridin-5(4H)-yl)phenoxy)methyl)-cyclopropanecarbonitrile | 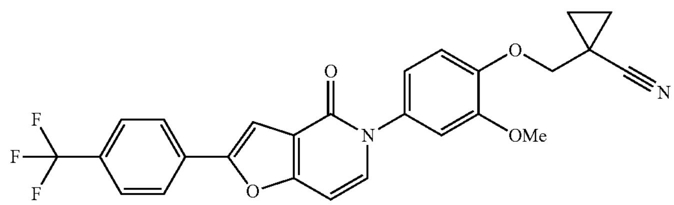 [SMILES: COc1cc(-n2ccc3oc(-c4ccc(C(F)(F)F)cc4)cc3c2=O)ccc1OCC1(C#N)CC1] | 481.1 |
| 28 | 1-((2-methoxy-4-(4-oxo-2-(4-(trifluoromethoxy)phenyl)furo[3,2-c]pyridin-5(4H)-yl)phenoxy)methyl)-cyclopropanecarbonitrile | 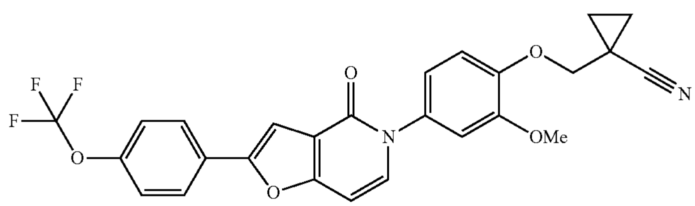 [SMILES: COc1cc(-n2ccc3oc(-c4ccc(OC(F)(F)F)cc4)cc3c2=O)ccc1OCC1(C#N)CC1] | 497.2 |
| 29 | 2-(4-chlorophenyl)-5-(4-cyclopentyl-3-methoxyphenyl)furo[3,2-c]pyridin-4(5H)-one | 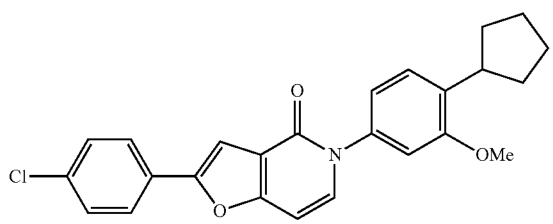 [SMILES: COc1cc(-n2ccc3oc(-c4ccc(Cl)cc4)cc3c2=O)ccc1C1CCCC1] | 420.1 |
| 30 | 2-(4-chlorophenyl)-5-(4-hydroxy-3-methoxyphenyl)furo[3,2-c]pyridin-4(5H)-one | 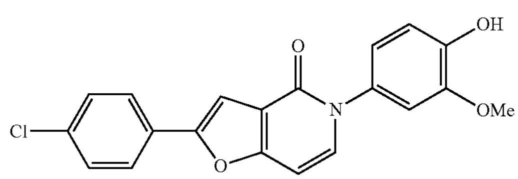 | 368.1 |
| 31 | 2-(4-chlorophenyl)-5-(3-hydroxyphenyl)furo[3,2-c]pyridin-4(5H)-one | 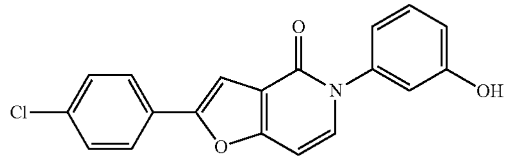 [SMILES: O=c1c2cc(-c3ccc(Cl)cc3)oc2ccn1-c1cccc(O)c1] | 338 |
| 32 | 2-(4-chlorophenyl)-5-(4-cyclohexyl-3-methoxyphenyl)furo[3,2-c]pyridin-4(5H)-one | 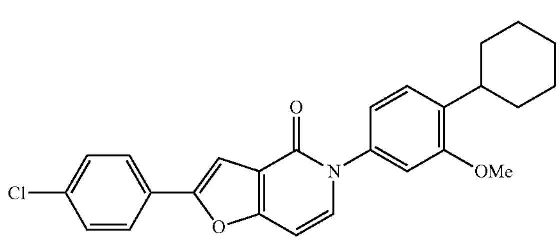 [SMILES: COc1cc(-n2ccc3oc(-c4ccc(Cl)cc4)cc3c2=O)ccc1C1CCCCC1] | 434.2 |

TABLE 1-continued

| Ex. | IUPAC name | Structure | MS |
|---|---|---|---|
| 33 | 1-((4-(2-(4-chlorophenyl)-4-oxofuro[3,2-c]pyridin-5(4H)-yl)-2-methylphenoxy)methyl)-cyclopropanecarbonitrile | 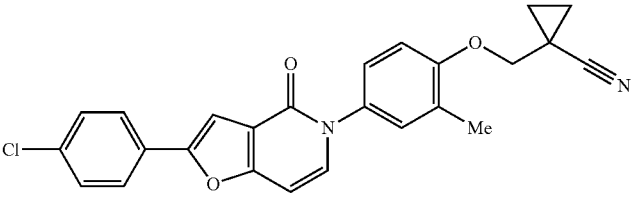 | 431.1 |
| 34 | 1-((3-(2-(4-chlorophenyl)-4-oxofuro[3,2-c]pyridin-5(4H)-yl)phenoxy)methyl)-cyclopropanecarbonitrile | 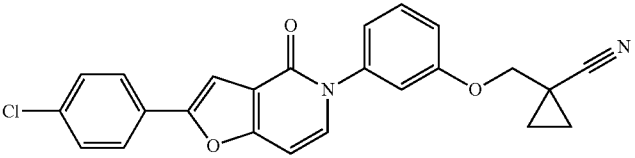 [SMILES: N#CC1(COc2cccc(-n3ccc4oc(-c5ccc(Cl)cc5)cc4c3=O)c2)CC1] | 417.1 |
| 35 | 2-(4-chlorophenyl)-5-(3-(3,3-dimethylbutoxy)phenyl)-furo[3,2-c]pyridin-4(5H)-one | 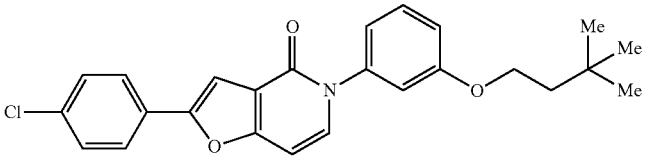 [SMILES: CC(C)(C)CCOc1cccc(-n2ccc3oc(-c4ccc(Cl)cc4)cc3c2=O)c1] | 422.1 |
| 36 | 2-(4-chlorophenyl)-5-(3-methoxy-4-(tetrahydrofuran-2-ylmethoxy)phenyl)furo[3,2-c]pyridin-4(5H)-one | 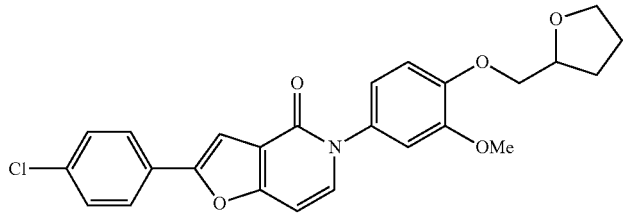 | 452.4 |
| 37 | 5-(6-bromo-1,2,3,4-tetrahydronaphthalen-2-yl)-2-(4-chlorophenyl)furo[3,2-c]pyridin-4(5H)-one | 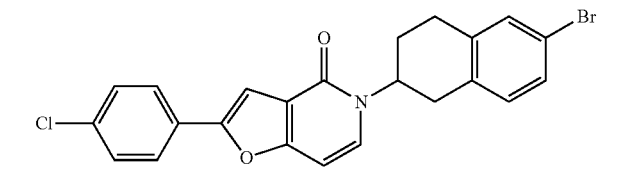 | 454 |
| 38 | 2-(4-chlorophenyl)-5-(4-(cyclopentylmethoxy)-3-methoxyphenyl)furo[3,2-c]pyridin-4(5H)-one | 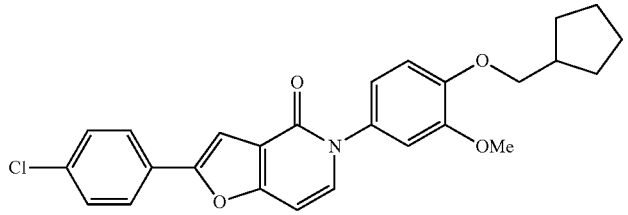 [SMILES: COc1cc(-n2ccc3oc(-c4ccc(Cl)cc4)cc3c2=O)ccc1OCC1CCCO1] | 450.1 |
| 39 | 2-(4-chlorophenyl)-5-(3-methoxy-4-(tetrahydrofuran-3-ylmethoxy)phenyl)-furo[3,2-c]pyridin-4(5H)-one | 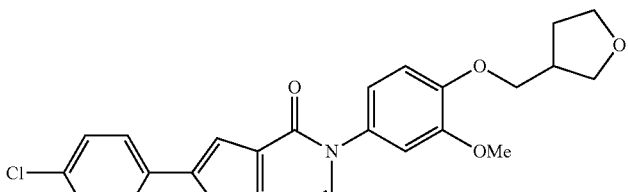 | 452.1 |

TABLE 1-continued

| Ex. | IUPAC name | Structure | MS |
|---|---|---|---|
| 40 | 2-(4-chlorophenyl)-5-(3-methoxy-4-(oxetan-3-ylmethoxy)phenyl)furo[3,2-c]pyridin-4(5H)-one | 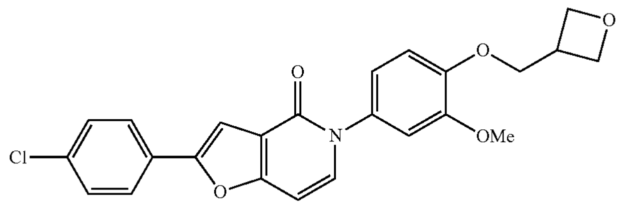 [SMILES: COc1cc(-n2ccc3oc(-c4ccc(Cl)cc4)cc3c2=O)ccc1OCC1COC1] | 438.1 |
| 41 | 2-(4-chlorophenyl)-5-(3-methoxy-4-((3-methyloxetan-3-yl)methoxy)phenyl)furo[3,2-c]pyridin-4(5H)-one | 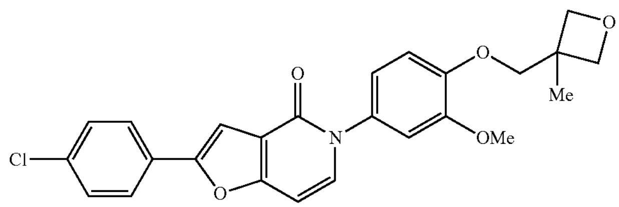 [SMILES: COc1cc(-n2ccc3oc(-c4ccc(Cl)cc4)cc3c2=O)ccc1OCC1(C)COC1] | 452.1 |
| 42 | 6-(2-(4-chlorophenyl)-4-oxofuro[3,2-c]pyridin-5(4H)-yl)-5,6,7,8-tetrahydronaphthalene-2-carbonitrile | 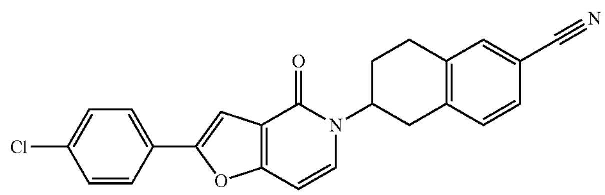 [SMILES: N#Cc1ccc2c(c1)CCC(n1ccc3oc(-c4ccc(Cl)cc4)cc3c1=O)C2] | 401.1 |
| 43 | 2-(4-chlorophenyl)-5-(3-methoxy-4-(oxetan-2-ylmethoxy)phenyl)furo[3,2-c]pyridin-4(5H)-one | 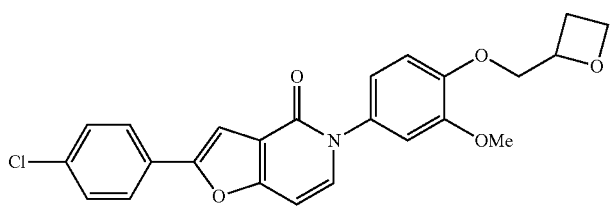 [SMILES: COc1cc(-n2ccc3oc(-c4ccc(Cl)cc4)cc3c2=O)ccc1OCC1CCO1] | 438.1 |
| 44 | 2-(4-chlorophenyl)-5-(4-((2,2-difluorocyclopropyl)methoxy)-3-methoxyphenyl)furo[3,2-c]pyridin-4(5H)-one | 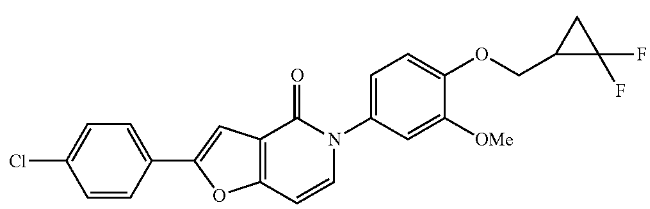 [SMILES: COc1cc(-n2ccc3oc(-c4ccc(Cl)cc4)cc3c2=O)ccc1OCC1CC1(F)F] | 458.1 |
| 45 | 4-(2-(4-chlorophenyl)-4-oxofuro[3,2-c]pyridin-5(4H)-yl)-N-(cyclopropylmethyl)-2-methoxybenzamide | 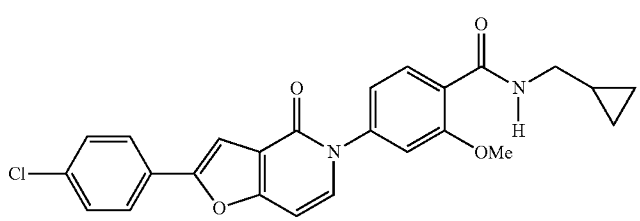 [SMILES: COc1cc(-n2ccc3oc(-c4ccc(Cl)cc4)cc3c2=O)ccc1C(=O)NCC1CC1] | 449 |
| 46 | 2-(4-chlorophenyl)-5-(4-(1-hydroxyethyl)-3-methoxyphenyl)furo[3,2-c]pyridin-4(5H)-one | 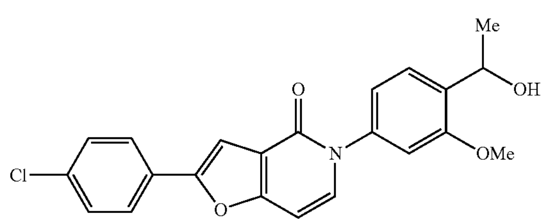 [SMILES: COc1cc(-n2ccc3oc(-c4ccc(Cl)cc4)cc3c2=O)ccc1C(C)O] | 396.2 |

TABLE 1-continued

| Ex. | IUPAC name | Structure | MS |
|---|---|---|---|
| 47 | 1-((4-(2-(4-chlorophenyl)-4-oxofuro[3,2-c]pyridin-5(4H)-yl)-2-ethylphenoxy)methyl)-cyclopropanecarbonitrile | 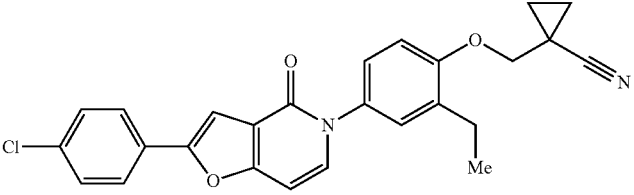 [SMILES: CCc1cc(-n2ccc3oc(-c4ccc(Cl)cc4)cc3c2=O)ccc1OCC1(C#N)CC1] | 445.2 |
| 48 | 2-(4-chlorophenyl)-5-(4-((3-ethyloxetan-3-yl)methoxy)-3-methoxyphenyl)furo[3,2-c]pyridin-4(5H)-one | 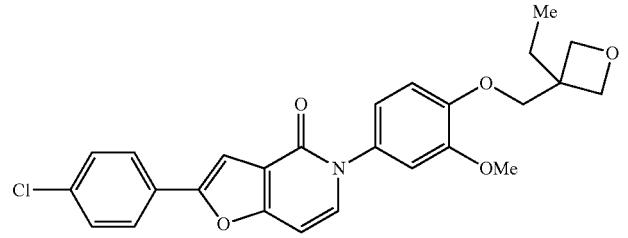 [SMILES: CCC1(COc2ccc(-n3ccc4oc(-c5ccc(Cl)cc5)cc4c3=O)cc2OC)COC1] | 466.1 |
| 49 | 5-(2-(4-bromophenyl)ethyl)-2-(4-chlorophenyl)furo[3,2-c]pyridin-4(5H)-one | 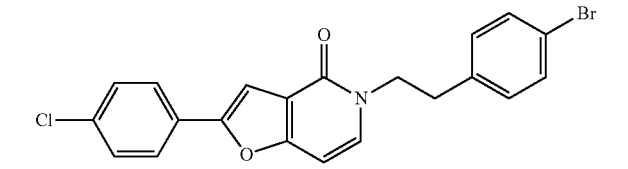 [SMILES: O=c1c2cc(-c3ccc(Cl)cc3)oc2ccn1CCc1ccc(Br)cc1] | 428 |
| 50 | 2-(4-(2-(4-chlorophenyl)-4-oxofuro[3,2-c]pyridin-5(4H)-yl)-2-methoxyphenoxy)acetamide | 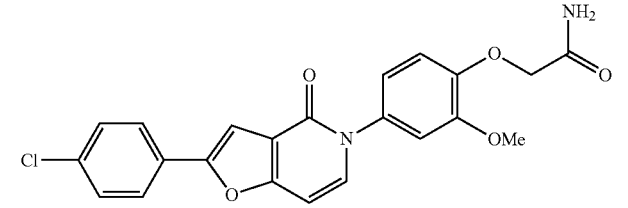 [SMILES: COc1cc(-n2ccc3oc(-c4ccc(Cl)cc4)cc3c2=O)ccc1OCC(N)=O] | 425 |
| 51 | 4-(4-(2-(4-chlorophenyl)-4-oxofuro[3,2-c]pyridin-5(4H)-yl)-2-methoxyphenoxy)-butanamide | 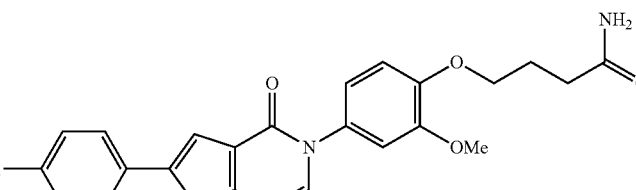 | 453.2 |
| 52 | 1-((4-(2-(4-chlorophenyl)-4-oxofuro[2,3-d]pyridazin-5(4H)-yl)-2-methoxyphenoxy)methyl)-cyclopropanecarbonitrile | 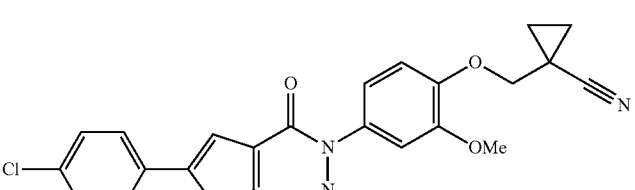 | |

$^1$H NMR (400 MHz, CHLOROFORM-d) δ 1.03-1.15 (2H, m), 1.29-1.41 (2H, m), 3.90 (3H, s), 4.01 (2H, s), 6.86-6.90 (1H, m), 6.92 (1H, s), 6.98 (1H, d, J = 8.7 Hz), 7.40 (2H, d, J = 8.5 Hz), 7.51-7.55 (1H, m), 7.63 (2H, d, J = 8.4 Hz), 8.03 (1H, s).

Preparation Example 1

| | | |
|---|---|---|
| (1) | Compound of Example 1 | 50 mg |
| (2) | Lactose | 34 mg |
| (3) | Cornstarch | 10.6 mg |
| (4) | Cornstarch (paste) | 5 mg |
| (5) | Magnesium stearate | 0.4 mg |
| (6) | Calcium carboxymethylcellulose | 20 mg |
| | Total | 120 mg |

The above-mentioned (1) to (6) are mixed according to a conventional method and the mixture is tableted by a tableting machine to give a tablet.

Preparation Example 2

Production of Capsule

| | | |
|---|---|---|
| (1) | Compound of Example 1 | 30 mg |
| (2) | Crystalline cellulose | 10 mg |
| (3) | Lactose | 19 mg |
| (4) | Magnesium stearate | 1 mg |
| | Total | 60 mg |

(1), (2), (3) and (4) are mixed and filled in a gelatin capsule.

Experimental Example 1

Determination of Human MCH Receptor 1 (MCHR1) Binding Inhibitory Activity of Test Compound Using Binding Assay 1. Preparation of Membrane Fraction Using human MCHR1(=SLC-1 receptor)-expressing CHO cell clone 57 described in WO01/82925, MCHR1-expressing CHO cellular membrane fractions were prepared by the following method.

In phosphate buffered saline (pH 7.4) supplemented with 5 mM EDTA (ethylenediaminetetraacetic acid) were respectively suspended human MCHR1-expressing CHO cells ($1\times10^8$ cells) and centrifuged. Homogenate buffer (10 mL, 10 mM $NaHCO_3$, 5 mM EDTA, pH 7.5, 0.5 mM PMSF (phenylmethylsulfonyl fluoride), 20 mg/L leupeptin, 4 mg/L E-64, 1 mg/L pepstatin A) was added to the pellets of the cells and, using Polytron Homogenizer, the mixture was homogenated. The supernatant obtained after centrifugation at 400×g for 10 min was further centrifuged at 100,000×g for 1 hr to give precipitate of the membrane fraction. The precipitate were suspended in 2 mL of assay buffer [20 mM Tris-HCl (pH 7.5), 5 mM EDTA, 0.5 mM PMSF, 20 mg/L leupeptin, 4 mg/L E-64, 1 mg/L pepstatin A]. The membrane fractions were suspended in assay buffer to a protein concentration of 2 mg/mL, and after dispensing, preserved at −80° C. and used upon thawing each time when in use.

2. Binding Assay

The MCHR1 ligand binding inhibitory activity of the test compound was determined as follows.

An MCHR1-expressing CHO cellular membrane fraction (173 μL) diluted with an assay buffer was dispensed to a 96 well polypropylene plate (3363, Corning). DMSO solution (2 μL), 33 μM cold MCH(1-19) diluted with DMSO solution (2 μL), or a test compound solution diluted with DMSO solution to various concentrations (2 μL) was added, and lastly, [$^{125}$I]-MCH(4-19) diluted with assay buffer (hereinafter, sometimes to be referred to as "hot MCH", 25 μL) was added to each well. The mixture was reacted with stirring at room temperature for 1 hr, and the plate was set on Filter-Mate Harvester (PerkinElmer). Using a treating glass filter plate (GF/C, PerkinElmer) with polyethyleneimine, which had been previously set, the plate was suction-filtered and washed three times with washing buffer (50 mM Tris-HCl buffer pH 7.5). The glass filter plate was dried, MicroScinti0 (PerkinElmer) was added at 25 μL/well, and the resulting radioactivity was measured by TopCount liquid scintillation counter (PerkinElmer). The binding inhibition rate of the test compound was calculated by the following formula.

Binding inhibition (%)=100−(radioactivity upon addition of test compound and hot MCH−radioactivity upon addition of cold MCH and hot MCH solution)/(radioactivity upon addition of DMSO solution and hot MCH−radioactivity upon addition of cold MCH and hot MCH solution)×100

The binding inhibition rates (%) of test compounds (0.1 μM) as measured using human MCHR1-expressing CHO cell are shown in Table 2.

TABLE 2

| compound No. | Binding inhibition rate % (0.1 μM) |
|---|---|
| Example 2 | 81 |
| Example 5 | 97 |
| Example 6 | 82 |
| Example 7 | 97 |
| Example 8 | 76 |
| Example 10 | 83 |
| Example 12 | 53 |
| Example 15 | 17 |
| Example 16 | 79 |
| Example 19 | 77 |
| Example 20 | 58 |
| Example 21 | 42 |
| Example 23 | 73 |
| Example 24 | 47 |
| Example 27 | 60 |
| Example 28 | 63 |
| Example 30 | 66 |
| Example 33 | 84 |
| Example 36 | 95 |
| Example 39 | 96 |
| Example 40 | 91 |
| Example 41 | 97 |
| Example 43 | 92 |
| Example 44 | 85 |
| Example 45 | 74 |
| Example 47 | 74 |
| Example 48 | 71 |
| Example 50 | 85 |
| Example 51 | 90 |

As is clear from Table 2, the compound of the present invention has a superior MCH receptor 1 binding inhibitory activity.

Experimental Example 2

Measurement of MCH Receptor 1 Antagonistic Activity of Test Compound Using $Ca^{2+}$ Mobilization Assay Using an expression vector plasmid introduced with human MCHR1 gene for expression in animal cells, human MCHR1 gene was introduced into CHO cells (CHO dhfr⁻) by Lipofectamine LTX (Invitrogen). The cells were cultured in selection MEMα medium [445 mL of MEMα medium without nucleic acid and added with 5 mL of Penicillin-Streptomycin (Invitrogen) and 50 mL of dialyzed fetal bovine serum]. Colony 24 clones grown in the selection medium, which were human MCHR1 gene-expressing CHO cell candidates, were selected. From these clones, clone #4 which showed the highest response to the change of $Ca^{2+}$ concentration on stimulation by the addition of 25 nM ligand MCH(4-19) was selected by $Ca^{2+}$ mobilization assay. In the following test, this human MCHR1-expressing CHO cell (clone #4) was used. An integrated dispensing function fluorometer (CellLux, PerkinElmer) was used for $Ca^2$ mobilization assay. The CHO cells were sown in a 96 well plate (type 3904, Corning) with a black wall and clear well bottom at a density of 20000 cells/well, and cultured in an incubator for about 24 hr at 5% $CO_2$, 37° C. The medium was removed, and the cells were washed with phosphate buffered saline (PBS). A $Ca^{2+}$ indicator dye reagent (DOJINDO LABORATORIES, Ca screening no-wash kit Fluo4) was added at 100 μL/well, and the dye was allowed to penetrate into the cell for 30 min in an incubator at 5% $CO_2$, 37° C. The plate was set on a plate reader. First, a test compound solution diluted with an assay buffer [10 mM HEPES (pH 7.4), 1× assay buffer containing 0.1% BSA (DOJINDO LABORATORIES, attached to Ca screening no-wash kit Fluo4)] or DMSO solution was added at 50 μL/well, and then ligand MCH (4-19) peptide (final concentration 2 nM) diluted with assay buffer or DMSO was added at 50 μL/well, during which changes in intracellular fluorescence were measured at 2 second intervals. The antagonistic activity of the test compound was calculated by the following formula and shown as an inhibition rate (%) wherein the intracellular fluorescence activity resulting from the stimulation by the addition of ligand MCH (4-19) peptide was 100% and that of the well added with DMSO solution alone was 0%.

inhibitory rate (%)=100−[fluorescence activity upon addition of test compound and MCH(4-19) peptide solution−fluorescence activity upon addition of DMSO solution only]/[fluorescence activity upon addition of DMSO solution and MCH(4-19) peptide solution−fluorescence activity upon addition of DMSO solution only]×100

The inhibition rates (%) of test compounds (0.1 μM) as antagonist activity measured using human MCHR1-expressing CHO cells (clone #4) are shown in the following Table 3.

TABLE 3

| compound No. | Inhibition rate % (0.1 μM) |
|---|---|
| Example 2 | 94 |
| Example 5 | 100 |
| Example 6 | 37 |
| Example 7 | 106 |
| Example 10 | 86 |
| Example 12 | 64 |
| Example 16 | 97 |
| Example 19 | 88 |
| Example 23 | 72 |
| Example 28 | 24 |
| Example 33 | 34 |
| Example 36 | 78 |
| Example 39 | 84 |
| Example 40 | 95 |
| Example 41 | 92 |
| Example 43 | 99 |
| Example 44 | 45 |

As is clear from Table 3, the compound of the present invention has a superior MCH receptor 1 antagonistic action.

INDUSTRIAL APPLICABILITY

Compound (I) has a melanin-concentrating hormone (MCH) receptor antagonistic action, and is low toxic. Therefore, the compound is highly useful as an anorexigenic agent and an agent for the prophylaxis or treatment of obesity and the like.

The present invention is based on U.S. patent application No. 61/645,167, the contents of which are incorporated by reference in full herein.

The invention claimed is:
1. A compound represented by the formula:

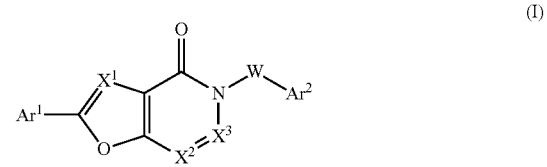

wherein
    $Ar^1$ is a phenyl group optionally substituted by 1 to 3 substituents selected from the group consisting of (1) a halogen atom, (2) a cyano group, (3) a nitro group, (4) an optionally substituted hydrocarbon group, (5) an optionally substituted nonaromatic heterocyclic group, (6) an optionally substituted hydroxy group, (7) an optionally substituted mercapto group, (8) an optionally substituted amino group, and (9) an acyl group;
    $Ar^2$ is a phenyl group substituted by 1 to 3 substituents selected from the group consisting of (1) a halogen atom, (2) a cyano group, (3) an optionally substituted hydrocarbon group, (4) an optionally substituted heterocyclic group, (5) an optionally substituted hydroxy group, (6) an optionally substituted mercapto group, (7) a substituted amino group, and (8) an acyl group;
    $X^1$, $X^2$ and $X^3$ are each CH;
    W is a bond, an optionally substituted $C_{1-6}$ alkylene group, or an optionally substituted $C_{2-6}$ alkenylene group;
wherein
    the "optionally substituted hydrocarbon group" is
        a $C_{1-6}$ alkyl group, a $C_{2-6}$ alkenyl group, or a $C_{2-6}$ alkynyl group, each optionally substituted by 1 to 7 substituents selected from the following Substituent Group A, or
        a $C_{7-13}$ aralkyl group, an aromatic hydrocarbon group, or a nonaromatic cyclic hydrocarbon group, each optionally substituted by 1 to 7 substituents selected from the following Substituent Group B;
    wherein Substituent Group A is selected from the group consisting of:
        (1) a $C_{3-10}$ cycloalkyl group optionally substituted by 1 to 3 substituents selected from the group consisting of a halogen atom and a cyano group;
        (2) a $C_{6-14}$ aryl group optionally substituted by 1 to 3 substituents selected from the group consisting of
            (a) a $C_{1-6}$ alkyl group optionally substituted by 1 to 3 halogen atoms, (b) a hydroxy group,
(c) a $C_{1-6}$ alkoxy group optionally substituted by 1 to 3 halogen atoms, and
(d) a halogen atom;
(3) an aromatic heterocyclic group optionally substituted by 1 to 3 substituents selected from the group consisting of
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(4) a nonaromatic heterocyclic group optionally substituted by 1 to 3 substituents selected from the group consisting of
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(5) an amino group optionally mono- or di-substituted by substituent(s) selected from the group consisting of
 (a) a $C_{1-6}$ alkyl group optionally substituted by 1 to 3 halogen atoms,
 (b) a $C_{1-6}$ alkyl-carbonyl group optionally substituted by 1 to 3 halogen atoms,
 (c) a $C_{1-6}$ alkoxy-carbonyl group optionally substituted by 1 to 3 halogen atoms,
 (d) a carbamoyl group optionally mono- or di-substituted by $C_{1-6}$ alkyl group(s) optionally substituted by 1 to 3 halogen atoms, and
 (e) a formyl group;
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from the group consisting of
 (a) a halogen atom, and
 (b) a $C_{1-6}$ alkoxy group;
(8) a $C_{1-6}$ alkylsulfonyl group optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from the group consisting of
 (a) a halogen atom,
 (b) a carboxy group,
 (c) a $C_{1-6}$ alkoxy group,
 (d) a $C_{1-6}$ alkoxy-carbonyl group,
 (e) an amino group optionally mono- or di-substituted by substituent(s) selected from the group consisting of a $C_{1-6}$ alkyl group and a $C_{1-6}$ alkoxy-carbonyl group,
 (f) a $C_{6-14}$ aryl group,
 (g) a $C_{3-10}$ cycloalkyl group,
 (h) an aromatic heterocyclic group, and
 (i) a hydroxy group;
(15) a $C_{2-6}$ alkenyloxy group optionally substituted by 1 to 3 halogen atoms;
(16) a $C_{6-14}$ aryloxy group;
(17) a $C_{1-6}$ alkyl-carbonyloxy group;
(18) a $C_{6-14}$ aryl-carbonyl group optionally substituted by 1 to 3 substituents selected from the group consisting of
 (a) a halogen atom, and
 (b) a $C_{1-6}$ alkyl group optionally substituted by 1 to 3 halogen atoms;
(19) a nonaromatic heterocyclylcarbonyl group optionally substituted by 1 to 3 $C_{1-6}$ alkyl groups optionally substituted by 1 to 3 halogen atoms;
(20) a mercapto group;
(21) a $C_{1-6}$ alkylthio group optionally substituted by 1 to 3 halogen atoms;
(22) a $C_{7-13}$ aralkylthio group;
(23) a $C_{6-14}$ arylthio group;
(24) a cyano group;
(25) a nitro group;
(26) a halogen atom;
(27) a $C_{1-3}$ alkylenedioxy group;
(28) an aromatic heterocyclylcarbonyl group optionally substituted by 1 to 3 $C_{1-6}$ alkyl groups optionally substituted by 1 to 3 halogen atoms; and
(29) a hydroxyimino group optionally substituted by a $C_{1-6}$ alkyl group optionally substituted by 1 to 3 $C_{6-14}$ aryl groups;
wherein Substituent Group B is selected from the group consisting of:
(1) Substituent Group A;
(2) a $C_{1-6}$ alkyl group optionally substituted by 1 to 3 substituents selected from the group consisting of
 (a) a halogen atom,
 (b) a carboxy group,
 (c) a hydroxy group,
 (d) a $C_{1-6}$ alkoxy-carbonyl group,
 (e) a $C_{1-6}$ alkoxy group,
 (f) an amino group optionally mono- or di-substituted by $C_{1-6}$ alkyl group(s), and
 (g) a $C_{3-10}$ cycloalkyloxy group;
(3) a $C_{2-6}$ alkenyl group optionally substituted by 1 to 3 substituents selected from the group consisting of
 (a) a halogen atom,
 (b) a carboxy group,
 (c) a hydroxy group,
 (d) a $C_{1-6}$ alkoxy-carbonyl group,
 (e) a $C_{1-6}$ alkoxy group,
 (f) an amino group optionally mono- or di-substituted by $C_{1-6}$ alkyl group(s), and
 (g) a $C_{3-10}$ cycloalkyl group;
(4) a $C_{2-6}$ alkynyl group optionally substituted by 1 to 3 $C_{3-10}$ cycloalkyl groups;
(5) a $C_{7-13}$ aralkyl group optionally substituted by 1 to 3 substituents selected from the group consisting of
 (a) a $C_{1-6}$ alkyl group optionally substituted by 1 to 3 halogen atoms,
 (b) a hydroxy group, (c) a $C_{1-6}$ alkoxy group, and
(d) a halogen atom; and
(6) an oxo group;
wherein
the "optionally substituted nonaromatic heterocyclic group" is a nonaromatic heterocyclic group optionally substituted by 1 to 5 substituents selected from the Substituent Group B;
the "optionally substituted heterocyclic group" is a heterocyclic group optionally substituted by 1 to 5 substituents selected from the Substituent Group B;
the "optionally substituted hydroxy group" is a hydroxy group, a $C_{1-6}$ alkoxy group optionally substituted by 1 to 3 substituents selected from the Substituent Group A, a $C_{2-6}$ alkenyloxy group optionally substituted by 1 to 3 substituents selected from the Substituent Group A, a $C_{2-6}$ alkynyloxy group optionally substituted by 1 to 3 substituents selected from the Substituent Group A, a $C_{6-14}$ aryloxy group optionally substituted by 1 to 3 substituents selected from the Substituent Group B, or a $C_{3-10}$ cycloalkyloxy group optionally substituted by 1 to 3 substituents selected from the Substituent Group B;
the "optionally substituted mercapto group" is a mercapto group, a $C_{1-6}$ alkylthio group optionally substituted by 1 to 3 substituents selected from the Substituent Group A, a $C_{2-6}$ alkenylthio group optionally substituted by 1 to 3 substituents selected from the Substituent Group A, a $C_{2-6}$ alkynylthio group optionally substituted by 1 to 3 substituents selected from the Substituent Group A, a $C_{6-14}$ arylthio group optionally substituted by 1 to 3 substituents selected from the Substituent Group B, a $C_{3-10}$ cycloalkylthio group optionally substituted by 1 to 3 substituents selected from the Substituent Group B;
the "optionally substituted amino group" is an amino group optionally substituted by 1 or 2 substituents selected from the group consisting of
(1) a $C_{3-10}$ cycloalkyl group optionally substituted by 1 to 3 substituents selected from the group consisting of a halogen atom and a cyano group;
(2) a $C_{6-14}$ aryl group optionally substituted by 1 to 3 substituents selected from the group consisting of
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group optionally substituted by 1 to 3 substituents selected from the group consisting of
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) a nonaromatic heterocyclic group optionally substituted by 1 to 3 substituents selected from the group consisting of
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(5) an amino group optionally mono- or di-substituted by substituent(s) selected from the group consisting of
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{1-6}$ alkoxy-carbonyl group optionally substituted by 1 to 3 halogen atoms,
  (d) a carbamoyl group optionally mono- or di-substituted by $C_{1-6}$ alkyl group(s) optionally substituted by 1 to 3 halogen atoms, and
  (e) a formyl group;
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from the group consisting of
  (a) a halogen atom, and
  (b) a $C_{1-6}$ alkoxy group;
(8) a $C_{1-6}$ alkylsulfonyl group optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a $C_{6-14}$ aryl-carbonyl group optionally substituted by 1 to 3 substituents selected from the group consisting of
  (a) a halogen atom, and
  (b) a $C_{1-6}$ alkyl group optionally substituted by 1 to 3 halogen atoms;
(14) a nonaromatic heterocyclylcarbonyl group optionally substituted by 1 to 3 $C_{1-6}$ alkyl groups optionally substituted by 1 to 3 halogen atoms;
(15) an aromatic heterocyclylcarbonyl group optionally substituted by 1 to 3 $C_{1-6}$ alkyl groups optionally substituted by 1 to 3 halogen atoms;
(16) a $C_{1-6}$ alkyl group optionally substituted by 1 to 3 substituents selected from the group consisting of
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by $C_{1-6}$ alkyl group(s), and
  (g) a $C_{3-10}$ cycloalkyloxy group;
(17) a $C_{2-6}$ alkenyl group optionally substituted by 1 to 3 substituents selected from the group consisting of
  (a) a halogen atom,
  (b) a carboxy group,
  (c) a hydroxy group,
  (d) a $C_{1-6}$ alkoxy-carbonyl group,
  (e) a $C_{1-6}$ alkoxy group, (f) an amino group optionally mono- or di-substituted by $C_{1-6}$ alkyl group(s), and
(g) a $C_{3-10}$ cycloalkyl group;
(18) a $C_{2-6}$ alkynyl group optionally substituted by 1 to 3 $C_{3-10}$ cycloalkyl groups;
(19) a $C_{7-13}$ aralkyl group optionally substituted by 1 to 3 substituents selected from the group consisting of
(a) a $C_{1-6}$ alkyl group optionally substituted by 1 to 3 halogen atoms,
(b) a hydroxy group,
(c) a $C_{1-6}$ alkoxy group, and
(d) a halogen atom;
the "substituted amino group" is an amino group substituted by 1 or 2 substituents selected from the group consisting of
(1) a $C_{3-10}$ cycloalkyl group optionally substituted by 1 to 3 substituents selected from the group consisting of a halogen atom and a cyano group;
(2) a $C_{6-14}$ aryl group optionally substituted by 1 to 3 substituents selected from the group consisting of
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom;
(3) an aromatic heterocyclic group optionally substituted by 1 to 3 substituents selected from the group consisting of
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom;
(4) a nonaromatic heterocyclic group optionally substituted by 1 to 3 substituents selected from the group consisting of
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom;
(5) an amino group optionally mono- or di-substituted by substituent(s) selected from the group consisting of
(a) a $C_{1-6}$ alkyl group optionally substituted by 1 to 3 halogen atoms,
(b) a $C_{1-6}$ alkyl-carbonyl group optionally substituted by 1 to 3 halogen atoms,
(c) a $C_{1-6}$ alkoxy-carbonyl group optionally substituted by 1 to 3 halogen atoms,
(d) a carbamoyl group optionally mono- or di-substituted by $C_{1-6}$ alkyl group(s) optionally substituted by 1 to 3 halogen atoms, and
(e) a formyl group;
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from the group consisting of
(a) a halogen atom, and
(b) a $C_{1-6}$ alkoxy group;
(8) a $C_{1-6}$ alkylsulfonyl group optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a $C_{6-14}$ aryl-carbonyl group optionally substituted by 1 to 3 substituents selected from the group consisting of
(a) a halogen atom, and
(b) a $C_{1-6}$ alkyl group optionally substituted by 1 to 3 halogen atoms;
(14) a nonaromatic heterocyclylcarbonyl group optionally substituted by 1 to 3 $C_{1-6}$ alkyl groups optionally substituted by 1 to 3 halogen atoms;
(15) an aromatic heterocyclylcarbonyl group optionally substituted by 1 to 3 $C_{1-6}$ alkyl groups optionally substituted by 1 to 3 halogen atoms;
(16) a $C_{1-6}$ alkyl group optionally substituted by 1 to 3 substituents selected from the group consisting of
(a) a halogen atom,
(b) a carboxy group,
(c) a hydroxy group,
(d) a $C_{1-6}$ alkoxy-carbonyl group,
(e) a $C_{1-6}$ alkoxy group,
(f) an amino group optionally mono- or di-substituted by $C_{1-6}$ alkyl group(s), and
(g) a $C_{3-10}$ cycloalkyloxy group;
(17) a $C_{2-6}$ alkenyl group optionally substituted by 1 to 3 substituents selected from the group consisting of
(a) a halogen atom,
(b) a carboxy group,
(c) a hydroxy group,
(d) a $C_{1-6}$ alkoxy-carbonyl group,
(e) a $C_{1-6}$ alkoxy group,
(f) an amino group optionally mono- or di-substituted by $C_{1-6}$ alkyl group(s), and
(g) a $C_{3-10}$ cycloalkyl group;
(18) a $C_{2-6}$ alkynyl group optionally substituted by 1 to 3 $C_{3-10}$ cycloalkyl groups;
(19) a $C_{7-13}$ aralkyl group optionally substituted by 1 to 3 substituents selected from the group consisting of
(a) a $C_{1-6}$ alkyl group optionally substituted by 1 to 3 halogen atoms,
(b) a hydroxy group,
(c) a $C_{1-6}$ alkoxy group, and
(d) a halogen atom;
the "optionally substituted $C_{1-6}$ alkylene group" is a $C_{1-6}$ alkylene group optionally substituted by 1 to 5 substituents selected from the following Substituent Group C;
wherein Substituent Group C is selected from the group consisting of:
(1) Substituent Group A, and
(2) an oxo group;

the "optionally substituted $C_{2-6}$ alkenylene group" is a $C_{2-6}$ alkenylene group optionally substituted by 1 to 5 substituents selected from the Substituent Group C;

the "optionally substituted 4- to 7-membered nonaromatic ring" is a 4- to 7-membered nonaromatic ring optionally substituted by 1 to 5 substituents selected from the Substituent Group B;

the "optionally substituted $C_{1-6}$ alkyl group" is a $C_{1-6}$ alkyl group optionally substituted by 1 to 5 substituents selected from the Substituent Group A;

the "optionally substituted $C_{3-10}$ cycloalkyl group" is a $C_{3-10}$ cycloalkyl group optionally substituted by 1 to 5 substituents selected from the Substituent Group B;

the "optionally substituted $C_{1-6}$ alkoxy group" is a $C_{1-6}$ alkoxy group optionally substituted by 1 to 5 substituents selected from the Substituent Group A;

or a salt thereof.

2. The compound according to claim 1, wherein $Ar^1$ is a phenyl group optionally substituted by 1 to 3 substituents selected from the group consisting of
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms,
or a salt thereof.

3. The compound according to claim 1, wherein $Ar^2$ is a phenyl group substituted by 1 to 3 substituents selected from the group consisting of
(1) a halogen atom,
(2) a cyano group,
(3) a $C_{1-6}$ alkyl group optionally substituted by 1 to 3 hydroxy groups,
(4) a $C_{3-10}$ cycloalkyl group,
(5) a hydroxy group,
(6) a $C_{1-6}$ alkoxy group optionally substituted by 1 to 3 substituents selected from the group consisting of
  (a) a hydroxy group,
  (b) a carbamoyl group,
  (c) a $C_{3-10}$ cycloalkyl group optionally substituted by 1 to 3 substituents selected from the group consisting of a halogen atom and a cyano group, and
  (d) a 4- to 6-membered saturated heterocyclic group optionally substituted by 1 to 3 $C_{1-6}$ alkyl groups,
(7) a $C_{1-6}$ alkoxy-carbonyl group, and
(8) a carbamoyl group optionally substituted by a $C_{3-10}$ cycloalkyl-$C_{1-6}$ alkyl group,
or a salt thereof.

4. The compound according to claim 1, wherein W is a bond or a $C_{1-6}$ alkylene group,
or a salt thereof.

5. The compound according to claim 1, wherein
$Ar^1$ is a phenyl group optionally substituted by 1 to 3 substituents selected from the group consisting of
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms;
$Ar^2$ is a phenyl group substituted by 1 to 3 substituents selected from the group consisting of
(1) a halogen atom,
(2) a cyano group,
(3) a $C_{1-6}$ alkyl group optionally substituted by 1 to 3 hydroxy groups,
(4) a $C_{3-10}$ cycloalkyl group,
(5) a hydroxy group,
(6) a $C_{1-6}$ alkoxy group optionally substituted by 1 to 3 substituents selected from the group consisting of
  (a) a hydroxy group,
  (b) a carbamoyl group,
  (c) a $C_{3-10}$ cycloalkyl group optionally substituted by 1 to 3 substituents selected from the group consisting of a halogen atom and a cyano group, and
  (d) a 4- to 6-membered saturated heterocyclic group optionally substituted by 1 to 3 $C_{1-6}$ alkyl groups,
(7) a $C_{1-6}$ alkoxy-carbonyl group, and
(8) a carbamoyl group optionally substituted by a $C_{3-10}$ cycloalkyl-$C_{1-6}$ alkyl group; and
W is a bond or a $C_{1-6}$ alkylene group;
or a salt thereof.

6. A pharmaceutical composition comprising the compound according to claim 1, or a salt thereof, and a pharmacologically acceptable carrier.

7. A method of antagonizing a melanin-concentrating hormone receptor in a mammal, comprising administering an effective amount of the compound according to claim 1 or a salt thereof to the mammal.

8. A method of suppressing food intake in a mammal, comprising administering an effective amount of the compound according to claim 1 or a salt thereof to the mammal.

9. A method for the prophylaxis or treatment of obesity in a mammal, comprising administering an effective amount of the compound according to claim 1 or a salt thereof to the mammal.

* * * * *